(12) United States Patent
Brown et al.

(10) Patent No.: US 10,632,101 B2
(45) Date of Patent: *Apr. 28, 2020

(54) METHODS AND COMPOSITIONS FOR SUPPORTING ENDOGENOUS SYSTEMS RELATED TO LIFE SPAN

(71) Applicant: USANA Health Sciences, Inc., Salt Lake City, UT (US)

(72) Inventors: Mark Brown, Salt Lake City, UT (US); John Cuomo, Salt Lake City, UT (US); Jeremy Tian, Salt Lake City, UT (US)

(73) Assignee: USANA Health Sciences, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/643,396

(22) Filed: Jul. 6, 2017

(65) Prior Publication Data

US 2018/0007945 A1 Jan. 11, 2018

Related U.S. Application Data

(60) Provisional application No. 62/359,106, filed on Jul. 6, 2016, provisional application No. 62/359,113, filed
(Continued)

(51) Int. Cl.

| | | |
|---|---|---|
| A23L 33/15 | (2016.01) |
| A23L 33/16 | (2016.01) |
| A61K 47/55 | (2017.01) |
| A61K 31/385 | (2006.01) |
| A61K 9/20 | (2006.01) |
| A61K 31/05 | (2006.01) |
| A61K 31/12 | (2006.01) |
| A61K 31/353 | (2006.01) |
| A61K 36/63 | (2006.01) |
| A61K 31/7048 | (2006.01) |
| A61K 31/015 | (2006.01) |
| A61K 31/232 | (2006.01) |
| A61K 31/375 | (2006.01) |
| A61K 31/355 | (2006.01) |
| A61K 31/593 | (2006.01) |
| A61K 31/122 | (2006.01) |
| A61K 31/4415 | (2006.01) |
| A61K 31/51 | (2006.01) |
| A61K 31/525 | (2006.01) |
| A61K 31/714 | (2006.01) |
| A61K 36/82 | (2006.01) |
| A61K 31/197 | (2006.01) |
| A61K 31/4188 | (2006.01) |
| A61K 31/455 | (2006.01) |
| A61K 31/519 | (2006.01) |
| A61K 31/01 | (2006.01) |
| A61K 31/047 | (2006.01) |
| A61K 31/14 | (2006.01) |
| A23L 33/00 | (2016.01) |
| A23L 33/155 | (2016.01) |
| A23L 33/10 | (2016.01) |
| A61K 45/06 | (2006.01) |
| A61K 31/382 | (2006.01) |

(Continued)

(52) U.S. Cl.
CPC ............ *A61K 31/385* (2013.01); *A23L 33/10* (2016.08); *A23L 33/15* (2016.08); *A23L 33/155* (2016.08); *A23L 33/16* (2016.08); *A23L 33/40* (2016.08); *A61K 9/20* (2013.01); *A61K 9/2054* (2013.01); *A61K 9/2059* (2013.01); *A61K 31/01* (2013.01); *A61K 31/015* (2013.01); *A61K 31/047* (2013.01); *A61K 31/05* (2013.01); *A61K 31/065* (2013.01); *A61K 31/12* (2013.01); *A61K 31/122* (2013.01); *A61K 31/14* (2013.01); *A61K 31/197* (2013.01); *A61K 31/232* (2013.01); *A61K 31/352* (2013.01); *A61K 31/353* (2013.01); *A61K 31/355* (2013.01); *A61K 31/375* (2013.01); *A61K 31/382* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/7048* (2013.01); *A61K 31/714* (2013.01); *A61K 36/63* (2013.01); *A61K 36/82* (2013.01); *A61K 45/06* (2013.01); *A61K 47/551* (2017.08); *A23V 2002/00* (2013.01)

(58) Field of Classification Search
None
See application file for complete search history.

(56) References Cited

U.S. PATENT DOCUMENTS 5,976,568 A * 11/1999 Riley
6,964,969 B2 * 11/2005 MCleary
(Continued)

*Primary Examiner* — Alma Pipic
(74) *Attorney, Agent, or Firm* — Kirton McConkie; Brian Tucker

(57) ABSTRACT

A composition for supporting endogenous systems related to life span, inhibiting mTOR, and reducing damage associated with oxidative phosphorylation. The composition comprises an upregulating compound mixture configured to upregulate an endogenous antioxidant system, an exogenous antioxidant mixture configured to inhibit oxidation of biomolecules by reactive oxygen species, and a mineral mixture configured to provide one or more cofactors to a endogenous antioxidant enzyme. The endogenous antioxidant system includes regulation of mitophagy through mTOR mediated regulation, and a Nrf2 transcription factors that promotes transcription of antioxidant genes.

17 Claims, 35 Drawing Sheets

Related U.S. Application Data on Jul. 6, 2016, provisional application No. 62/359,120, filed on Jul. 6, 2016.

(51) Int. Cl.
*A61K 31/352* (2006.01)
*A61K 31/065* (2006.01)

(56) References Cited

U.S. PATENT DOCUMENTS

| | | |
|---|---|---|
| 2008/0219964 A1* | 9/2008 | Keefe |
| 2009/0220477 A1* | 9/2009 | Brown |
| 2011/0038967 A1* | 2/2011 | Rabovsky |
| 2011/0293759 A1* | 12/2011 | Westerlund |
| 2014/0023701 A1* | 1/2014 | Montesinos |

* cited by examiner

METHODS AND COMPOSITIONS FOR SUPPORTING ENDOGENOUS SYSTEMS RELATED TO LIFE SPAN

RELATED APPLICATIONS

This application claims priority to U.S. Provisional Patent Application No. 62/359,106, filed Jul. 6, 2016, entitled "METHODS AND COMPOSITIONS FOR UPREGULATING ENDOGENEOUS ANTIOXIDANT SYSTEMS," and claims priority to U.S. Provisional Patent Application No. 62/359,113, filed Jul. 6, 2016, entitled "METHODS AND COMPOSITIONS FOR REDUCING DAMAGE ASSOCIATED WITH OXIDATIVE PHOSPHORYLATION," and claims the benefit of U.S. Provisional Patent Application No. 62/359,120, filed Jul. 6, 2016, and entitled "METHODS AND COMPOSITIONS FOR SUPPORTING ENDOGENOUS SYSTEMS RELATED TO LIFE SPAN," the entire disclosures of which are hereby incorporated by reference.

BACKGROUND

This disclosure pertains to methods and compositions for supporting endogenous systems related to life span. More particularly, it pertains to nutritional supplements configured to upregulate endogenous systems related to increasing life span. Additionally, it pertains to methods of manufacturing these nutritional supplements and methods of administering these nutritional supplements. The nutritional supplements can comprise various active ingredients including antioxidant compounds and compounds which upregulate endogenous antioxidant systems (e.g., compounds such as, but not limited to, alpha lipoic acid, resveratrol, curcumin, EGCG, Olivol®, rutin, quercetin, and hesperetin).

Conventional nutritional supplements often comprise nutrients such as vitamins, minerals, dietary elements, fatty acids, and other vital nutrients. These nutrients often include compounds such as vitamins that are vital for growth and development but cannot be produced by the body. Sometimes nutritional supplements can include exogenous antioxidants such as vitamin C, vitamin E, beta-carotene, and other carotenoids that provide the body protection against free radicals provided that the exogenous antioxidants are absorbed and retained by the body in sufficient concentrations. Because the body cannot produce some of these exogenous antioxidants and because they can be excreted by certain systems in the body, these exogenous antioxidants must be regularly consumed to provide ongoing protection against free radicals.

In addition to systems to utilize exogenous antioxidants, the body also comprises endogenous antioxidant systems that can help defend against free radical damage. These endogenous antioxidant systems include endogenous antioxidants such as glutathione and thioredoxin and antioxidant enzymes such as glutathione reductase, glutathione peroxidases, glutathione-S-transferases (GST), thioredoxin reductase, superoxide dismutase (SOD), NAD(P)H dehydrogenase, quinone 1 (NQO-1), heme oxygenase 1 (HO-1), and glutamate-cysteine ligase, catalytic subunit (GCL).

Although conventional nutritional supplements provide a variety of benefits, conventional nutritional supplements are not necessarily without their shortcomings. For example, while conventional nutritional supplements may provide exogenous antioxidants, conventional nutritional supplements do not spur the body to upregulate its own endogenous antioxidant systems. Also, while conventional nutritional supplements may provide exogenous antioxidants, the conventional nutritional supplements are not configured to provide the long-lasting benefit of an increase in endogenous antioxidants.

Thus, while some conventional nutritional supplements currently exist, challenges still persist, including those listed above. Accordingly, it would be an advancement in the art to improve or replace current techniques and/or formulations.

BRIEF SUMMARY

The present application discloses compositions and methods for upregulating endogenous systems for increasing life span, upregulating endogenous systems to reduce oxidative burden through mitophagy, and upregulating endogenous antioxidant systems. In some embodiments, the compositions include a nutritional supplement for reducing free radical damage that comprises an upregulating compound mixture configured to upregulate an endogenous antioxidant system, an exogenous antioxidant mixture; and a mineral mixture. The upregulating compound mixture may comprise one or more of alpha lipoic acid, resveratrol, curcumin, EGCG, Olivol®, rutin, quercetin, and hesperetin. The exogenous antioxidant mixture can comprise one or more of mixed carotenoids, beta carotene, retinyl acetate, vitamin C, vitamin D3, vitamin E, mixed tocopherols, vitamin K1, vitamin K2, vitamin B1, vitamin B2, niacin, niacinamide, vitamin B6, folic acid, vitamin B12, biotin, pantothenic acid, inositol, choline bitartrate, coenzyme Q-10, lutein, and lycopene.

In some embodiments, the nutritional supplement comprises a first vehicle comprising an upregulating compound mixture configured to upregulate an endogenous antioxidant system and an exogenous antioxidant mixture and a second vehicle comprising a mineral mixture. The first and second vehicle can comprise a single solid tablet. The upregulating compound mixture may comprise one or more, but is not limited to alpha lipoic acid, resveratrol, curcumin, EGCG, Olivol®, rutin, quercetin, and hesperetin. The exogenous antioxidant mixture can comprise one or more of mixed carotenoids, beta carotene, retinyl acetate, vitamin C, vitamin D3, vitamin E, mixed tocopherols, vitamin K1, vitamin K2, vitamin B1, vitamin B2, niacin, niacinamide, vitamin B6, folic acid, vitamin B12, biotin, pantothenic acid, inositol, choline bitartrate, coenzyme Q-10, lutein, and lycopene.

In some embodiments, the methods for increasing life span and reducing free radical damage comprise administering a first vehicle comprising an upregulating compound mixture configured to regulate oxidative stress through mitophagy, upregulate an endogenous antioxidant system and an exogenous antioxidant mixture and administering a second vehicle comprising a mineral mixture, in which the upregulating compound mixture is configured to upregulate an endogenous antioxidant system to reduce free radical damage and oxidative stress through mitophagy.

The endogenous antioxidant system may comprise regulation of mTOR, and a transcription factor (e.g., Nrf2). Mitophagy is the selective degradation of mitochondria by autophagy. It often occurs to defective mitochondria following damage or stress. Mitophagy is an important key in keeping the cell healthy. It promotes turnover of mitochondria and prevents accumulation of dysfunctional mitochondria, which can lead to cellular degeneration. It is mediated by Atg32 (in yeast) and NIP3-like protein X (NIX). Mitophagy is regulated by PINK1 and parkin protein. Mitophagy is not limited to damaged mitochondria, but is also critical to maintain the functional capacity of undamaged mitochondria, while reducing their production of free radicals. The transcription factor (e.g., Nrf2) can promote transcription of an antioxidant gene such as a Phase II gene, a NQO1 gene, a GCL gene, a sulfiredoxin 1 (SRXN1) gene, a thioredoxin reductase 1 (TXNRD1) gene, a HO-1 gene, a GST family gene, and an UDP-glucuronosyltransferase (UGT) family gene.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION

Figure 1A:
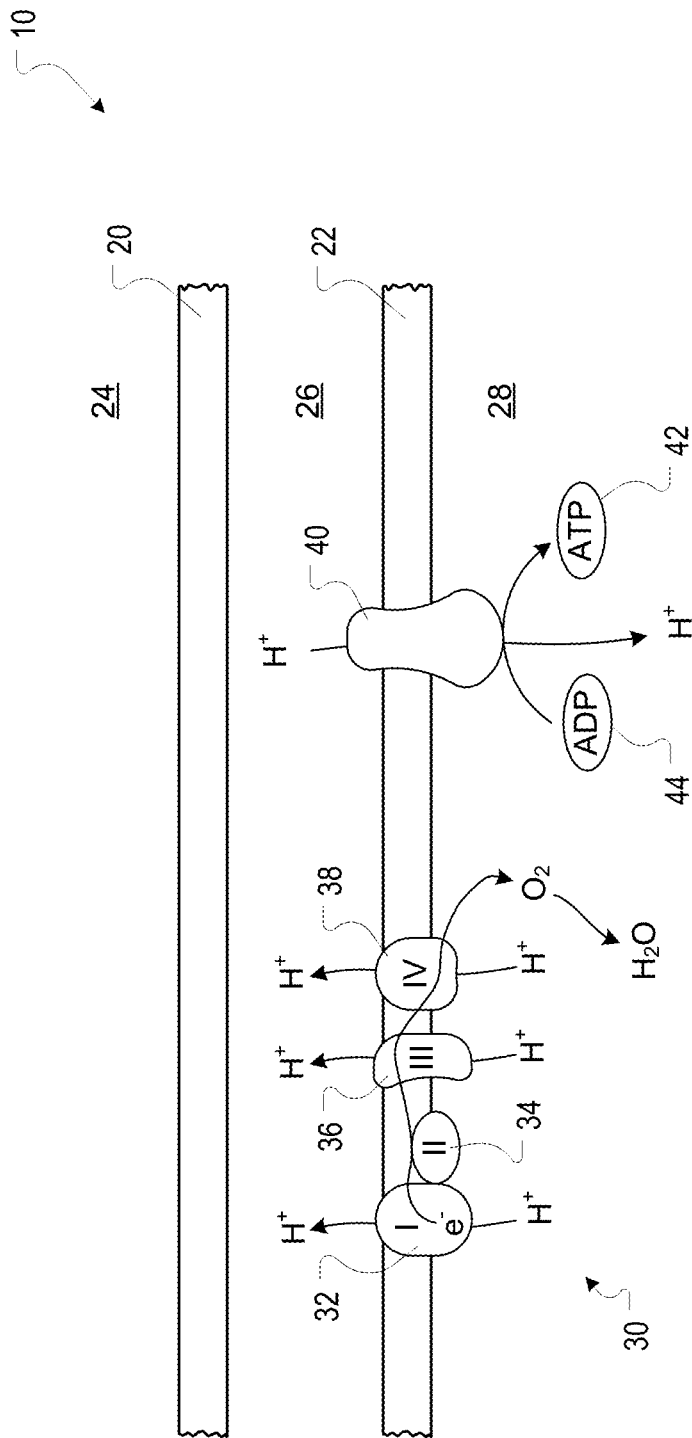
FIG. 1A illustrates a model of an oxidative phosphorylation system.

Described herein are nutritional supplement compositions configured to upregulating endogenous systems for increasing life span, upregulating endogenous systems to reduce oxidative burden through mitophagy, and upregulating endogenous antioxidant systems. In some embodiments, the methods and compositions disclosed in the present application include methods of preparing compositions of nutritional supplements that comprise one or more of an upregulating compound mixture, an exogenous antioxidant mixture, and a mineral mixture. In other embodiments, the methods of preparing nutritional supplements and compositions of nutritional supplements comprise preparing nutritional supplements that comprise an upregulating compound mixture and an exogenous antioxidant mixture in a first part and a mineral mixture in a second part.

The free radical theory of aging states that organisms age because cells accumulate free radical damage over time. Most biologically-relevant free radicals are highly reactive. For most biological structures, free radical damage is closely associated with oxidative damage. Antioxidants are reducing agents, and limit oxidative damage to biological structures by passivating them from free radicals. The free radical theory encompasses oxidative damage caused by free radicals such as superoxide (O2-), other reactive oxygen species such as hydrogen peroxide (H2O2) or peroxynitrite (OONO—), and mitochondrial production of reactive oxygen species. Reducing oxidative damage can extend lifespan. The free radical theory of aging relies on the underlying thesis that oxygen free radicals produced during normal respiration cause cumulative damage, which would eventually lead to organismal loss of functionality, and ultimately death.

The free radical theory includes not only aging, but also age-related diseases. Free radical damage within cells has been linked to a range of disorders including cancer, arthritis, atherosclerosis, Alzheimer's disease, and diabetes. Free radicals and some reactive nitrogen species trigger and increase cell death mechanisms within the body such as apoptosis and in extreme cases necrosis.

The free radical theory encompasses the mitochondrial theory of aging. The mitochondrial theory proposes that reactive oxygen species that are produced in the mitochondria, causes damage to certain macromolecules including lipids, proteins and most importantly mitochondrial DNA. This damage then causes mutations which lead to an increase of ROS production and greatly enhance the accumulation of free radicals within cells. The mitochondrial theory plays a major role in contributing to the aging process.

Numerous studies have demonstrated a role for free radicals in the aging process and thus support the free radical theory of aging. Studies have shown a significant increase in superoxide radical (SOR) formation and lipid peroxidation in aging rats. Studies suggest ROS production increases with age and indicated the conversion of XDH to XOD may be an important contributing factor. This was supported by a study that showed superoxide production by xanthine oxidase and NO synthase in mesenteric arteries was higher in older rats than young ones.

Referring now to FIG. 1A, a model of an oxidative phosphorylation system 10 is illustrated. While other arrangements of electron transport chains may occur in the cell, FIG. 1A illustrates that the oxidative phosphorylation system 10 can include an outer bilayer membrane 20 of the mitochondria and an inner bilayer membrane 22 of the mitochondria. The outer bilayer membrane 20 can separate the mitochondria from the cytosol 24. An intermembrane space 26 can exist between the outer bilayer membrane 20 and the inner bilayer membrane 22. The inner bilayer membrane 22 can divide the intermembrane space 26 from the mitochondrial matrix 28.

In some embodiments, the oxidative phosphorylation system 10 includes an electron transport chain 30. The electron transport chain 30 can include one or more complexes disposed within and/or traversing the inner bilayer membrane 22. In some cases the electron transport chain 30 can comprise a complex I 32, a complex II 34, a complex III 36, and a complex IV 38. Electrons can be transported from complex I 32 to complex II 34 to complex III 36 and then to complex IV 38. As the electrons are transported from complex to complex, one or more of the complexes can use the resultant energy to pump protons from the mitochondrial matrix 28 to the intermembrane space 26. Complex I 32 comprises a NADH-coenzyme Q oxidoreductase that binds an nicotinamide adenine dinucleotide (NADH), extracts two electrons, pumps four protons from the matrix 28 into the intermembrane space 26, and hands off the electrons to a ubiquinone molecule reducing it to a ubiquinol and taking up two protons from the matrix 28. Complex II 34 comprises a succinate-Q oxidoreductase that oxidizes a succinate in the matrix 28 to a fumarate and two protons and reduces ubiquinone. Complex III 36 comprises a Q-cytochrome c oxidoreductase that oxidizes one molecule of ubiquinol and reduces two molecules of cytochrome c while transferring four protons into the intermembrane space 26. Complex IV 38 comprises a cytochrome c oxidase that transfers electrons to oxygen as a terminal electron acceptor with the oxygen then reduced to water while pumping four protons into the intermembrane space 26. Although in most cases the electrons flow along the electron transport chain and are finally transferred to oxygen as the terminal electron acceptor, in some cases, the electrons can leak from the system and form ROS such as superoxides.

In some embodiments, the oxidative phosphorylation system 10 includes an ATP synthase 40 (i.e., complex V). The ATP synthase 40 can harness the proton gradient between the intermembrane space 26 and the matrix 28 to regenerate ATP 42 from ADP 44 (adenosine diphosphate) and phosphate. The ATP synthase 40 is a large protein complex that spans the inner bilayer membrane 22 with a channel that allows protons to flow across the proton gradient from the intermembrane space 26 to the matrix 28. The ATP synthase 40 utilizes this flow of protons across the proton gradient from the intermembrane space 26 to the matrix 28 to power a molecular motor that regenerates ATP 42 from ADP 44 and phosphate on the matrix facing side of the ATP synthase 40 to generate ATP 42 that can be used as an energy carrier to power the activities of the cell. In this manner, the cell can oxidize nutrients to drive electrons along the electron transport chain 30, harness the flow of electrons along the electron transport chain 30 to pump protons into the intermembrane space 26 to generate a proton gradient, and then harness the proton gradient with the ATP synthase 40 to regenerate ATP 42 that can be used as an energy carrier by the cell.

Figure 1B:
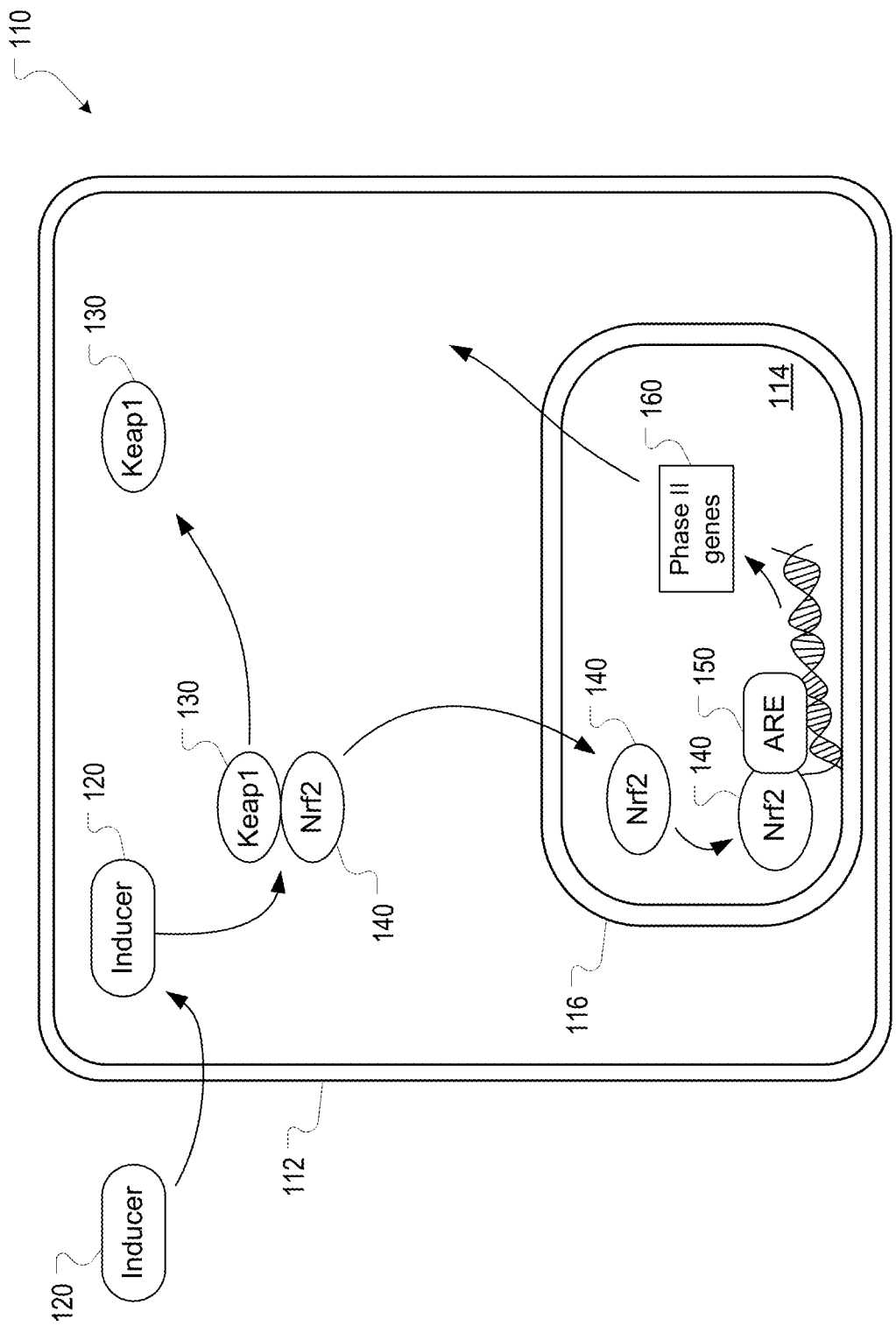
FIG. 1B illustrates a model of upregulation of endogenous antioxidant systems.
Figure 1C:
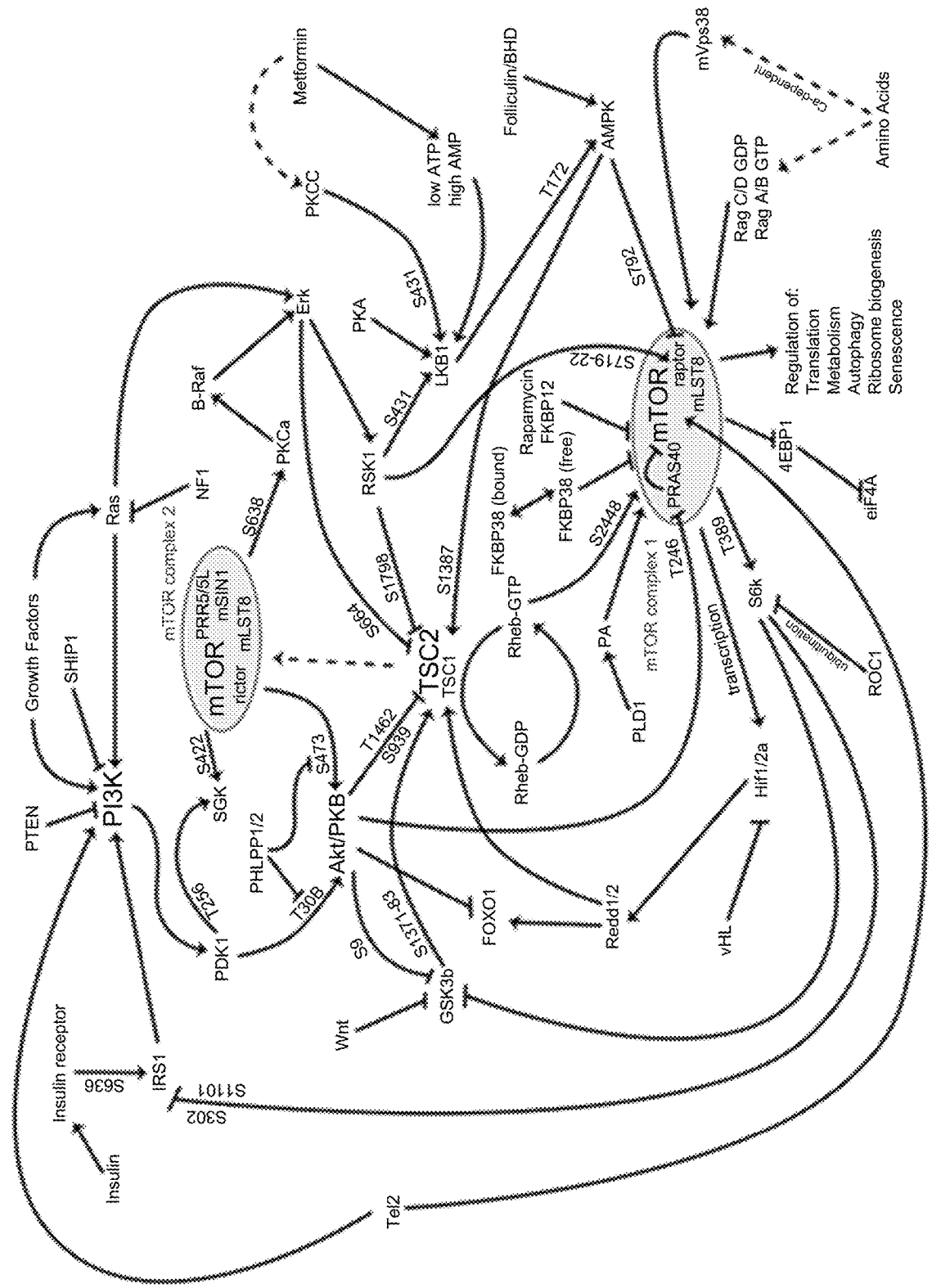
FIGS. 1C-1G illustrate that mTOR is the catalytic subunit of two structurally distinct complexes: mTORC1 and mTORC2.

As described above, the cell can employ endogenous antioxidant systems to counteract the effects oxidative stress caused by ROS and/or free radicals created during the process of oxidative phosphorylation. In some embodiments, these endogenous antioxidant systems can be upregulated to detoxify ROS and/or repair damage caused by ROS. Referring now to FIG. 1B, a model of upregulation of an endogenous antioxidant system is illustrated. While various endogenous antioxidant systems may be upregulated, FIG. 1B illustrates a possible model for upregulation of endogenous antioxidant Phase II genes through a transcription factor, nuclear factor erythroid 2-related factor (Nrf2). The model can include a living cell 110 that comprises an outer membrane 112. The cell 110 can also comprise an inner nucleus 114 that is bounded by a nuclear membrane 116. The model can also include an inducer 120 that can signal upregulation of an endogenous antioxidant system (e.g., Phase II genes). The inducer 120 can include any suitable molecule such as a signaling molecule or an upregulating compound that can upregulate an endogenous antioxidant system. In some cases, the inducer 120 can cross the outer membrane 112 to signal upregulation of an endogenous antioxidant system. In other cases, the inducer 120 can interact with a receptor at the outer membrane 112 to signal upregulation of an endogenous antioxidant system. In yet other cases, the inducer 120 can interact with one or more signaling molecules and/or signaling complexes to signal upregulation of an endogenous antioxidant system.

In some embodiments, after the inducer 120 crosses the outer membrane 112, it acts to disrupt a complex formed by an inhibitor 130 such as keap1 and a transcription factor 140 such as Nrf2. Now free of the inhibitor 130, the transcription factor 140 can cross over the nuclear membrane 116 to enter the nucleus 114. In other embodiments, the inducer 120 disrupts the complex formed by the inhibitor 130 and the transcription factor 140 by binding to the inhibitor 130 and allowing the transcription factor 140 to be freed. In some cases, once the transcription factor 140 enters the nucleus it can interact with and/or activate one or more response elements 150 such as an Antioxidant Response Element (ARE). The response elements 150 can then interact to promote transcription of endogenous antioxidant genes 160 (e.g., Phase II genes).

In some cases, damage by free radicals in cells of the body is linked to ageing and/or other acute and/or chronic diseases. Free radicals can include highly reactive atoms or molecules containing unpaired electrons. Free radicals can cause damage in biological systems when the free radical captures an electron from another molecule to pair with its unpaired electron. The molecule from which the electron was captured then becomes a free radical itself and seeks to capture another electron from another molecule, causing a chain reaction of free radical production. Often, when a biological molecule loses an electron, it becomes damaged and ceases to function properly, which can lead to damage within the cell. Free radicals can also cause cross-linking of biological structures such as cross-linking of DNA. DNA cross-linking may be damaging to the cell and may lead to ageing and diseases such as cancer. Free radical induced cross-linking may also be related to the formation of wrinkles, the formation of plaque in arteries leading to heart disease and stroke, and other chronic diseases.

In some cases, mitochondria are thought to be a main target of damage by free radicals. The production of energy through oxidative phosphorylation in the mitochondria provides the energy that, in some cases, animals (including humans) can use a metabolic process known as oxidative phosphorylation to oxidize nutrients to generate an energy carrier in the form of an adenosine triphosphate (ATP) molecule. Oxidative phosphorylation takes place in the mitochondria organelles within an individual cell and involves a process by which electrons are transferred from electron donors to electron acceptors by a series of protein complexes that work together as an electron transport chain.

The energy released by the transfer of electrons along the electron transport chain is used to pump protons across the inner mitochondrial membrane from a mitochondrial matrix to an intermembrane space to form a proton or pH gradient. In a process known as chemiosmosis, this proton gradient then powers a molecular complex known as an ATP synthase that regenerates ATP. The final reaction in the electron transport chain transfers electrons to oxygen as a terminal electron acceptor with the oxygen then reduced to water. While in most cases oxidative phosphorylation works effectively to transfer electrons to the terminal electron acceptor oxygen to be reduced harmlessly to water, in some cases, the transfer of electrons to oxygen can create dangerous intermediates.

In some cases, these dangerous intermediates can include reactive oxygen species (ROS) such as superoxide and/or peroxide anions. In other cases, reactive oxygen species (ROS) can include reaction products of superoxide and/or peroxide anions such as hydroxyl radicals. In yet other cases, reactive oxygen species (ROS) can also include hydrogen peroxide, organic hydroperoxides, alkoxy and peroxy radicals, hypochlorous acid, and/or peroxynitrites. While most of the ROS generated during oxidative phosphorylation is neutralized, it is possible in some cases that the reactive intermediates are not neutralized and can cause damage to the mitochondria and in particular to the mitochondrial DNA and mitochondrial proteins. This damage to the mitochondrial DNA and mitochondrial proteins can lead to decreased mitochondrial efficiency. In some instances, the reactive intermediates can also leak into the cell and cause oxidative damage to and/or death of the cell.

In some cases, the reactive intermediates can cause damage to biological systems in the cell. For example, the reactive intermediates can cause damage by capturing electrons from other biologically important molecules and by turning those molecules that have given up electrons into free radicals that seek to themselves capture electrons from other molecules, causing a chain reaction of free radical production. Many times, when a biological molecule loses electron(s) it ceases to function correctly, leading to malfunction and damage to systems of the cell. Free radicals can also lead to cross-linking of biomolecules such as cross-linking of DNA. DNA cross-linking may be damaging to the cell and can lead to a number of disease conditions such as cancer and other acute and chronic conditions.

Antioxidants are helpful in reducing and preventing damage from free radical reactions because of their ability to donate electrons which neutralize the radical without forming another. Ascorbic acid, for example, can lose an electron to a free radical and remain stable itself by passing its unstable electron around the antioxidant molecule. Appropriate amounts of antioxidants, with their ability to decrease the numbers of free radicals, lessen the radical damage causing chronic diseases, and even radical damage responsible for aging. Further, lower levels of endogenous ROS production is a factor in resistance to oxidative stress and long life, cellular dysfunction, inflammation and oxidative stress.

In some cases, the threat of ROS produced by oxidative phosphorylation is contained by cellular systems that detoxify ROS and/or repair damage caused by ROS. In other cases, these cellular systems can use exogenous antioxidants to inhibit the oxidation of biomolecules by ROS and effectively neutralize the oxidizing effects of ROS and/or free radicals. These exogenous antioxidants can include thiols or ascorbic acid (vitamin C), vitamin E, beta-carotene, and other carotenoids obtained through the animal's diet.

Additionally, the cell can also utilize various endogenous systems to detoxify ROS and/or repair damage caused by ROS. In some embodiments, these endogenous antioxidant systems generate endogenous antioxidants such as glutathione and thioredoxin that are configured to neutralize free radicals. In other embodiments, the endogenous antioxidant systems comprise endogenous antioxidant genes and/or enzymes that work to replenish or recharge the supply of endogenous antioxidants. In yet other embodiments, the endogenous antioxidant systems comprise endogenous antioxidant enzymes that themselves neutralize free radicals and/or reduce the damage caused by free radicals. These endogenous antioxidant genes and/or enzymes can include, but are not limited to, glutathione reductase, glutathione peroxidases, glutathione-S-transferases (GST), thioredoxin reductase, superoxide dismutase (SOD), NAD (P) H Dehydrogenase, Quinone 1 (NQO-1), Heme Oxygenase 1 (HO-1), and Glutamate-Cysteine Ligase, Catalytic Subunit (GCL), and proteins encoded by Phase II genes.

Generation of ATP by oxidative phosphorylation leads to the production of various reactive oxygen species (ROS) in the mitochondria, and submitochondrial particles. Formation of ROS as a mitochondrial waste product will eventually lead to cytotoxicity and cell death. Because of their role in metabolism, mitochondria are very susceptible to ROS damage.

Damaged mitochondria causes a depletion in ATP and a release of cytochrome c, which leads to activation of caspases and onset of apoptosis. Mitochondrial damage is not caused solely by oxidative stress or disease processes; normal mitochondria will eventually accumulate oxidative damage hallmarks overtime, which can be deleterious to mitochondria as well as to the cell. These faulty mitochondria can further deplete the cell from ATP, increase production of ROS, and release proapoptotic proteins such as caspases.

Because of the danger of having damaged mitochondria in the cell, the timely elimination of damaged and aged mitochondria is essential for maintaining the integrity of the cell. This turnover process consists of the sequestration and hydrolytic degradation of damaged and aged mitochondria by the lysosome, a process also known as mitophagy.

The endogenous antioxidant system may comprise regulation of mTOR mediated mitophagy, selectively endogenously upregulating the degradation of damaged and aged mitochondria by autophagy. The endogenous antioxidant system may comprise regulation of mTOR. Mitophagy often occurs to defective mitochondria following damage or stress. Mitophagy is an important key to keeping the cell healthy. It promotes turnover of mitochondria and prevents accumulation of dysfunctional mitochondria, which can lead to cellular degeneration. Mitophagy is mediated by Atg32 (in yeast) and NIP3-like protein X (NIX). Mitophagy is regulated by PINK1 and parkin protein. Mitophagy is not limited to damaged mitochondria but is also critical to maintain the functional capacity of undamaged mitochondria, while reducing their production of free radicals.

During mitophagy organelles, portions of cytoplasm are sequestered and targeted for degradation by the lysosome for hydrolytic digestion by a process known as autophagy. Because mitochondria metabolism leads to the creation of by-products that lead to DNA damage and mutations, a healthy population of mitochondria is critical for the well-being of cells.

The mitochondrial theory of aging is supported by studies that implicate mitochondria as the chief target of radical damage, since there is a known chemical mechanism by which mitochondria can produce ROS, mitochondrial components such as mtDNA are not as well protected as nuclear DNA, and by studies comparing damage to nuclear and mtDNA that demonstrate higher levels of radical damage on the mitochondrial molecules. Electrons may escape from metabolic processes in the mitochondria like the Electron transport chain, and these electrons may, in turn, react with water to form ROS such as the superoxide radical, or via an indirect route the hydroxyl radical. These radicals then damage the mitochondria's DNA and proteins, and these damaged components in turn are more liable to produce ROS byproducts. Thus a positive feedback loop of oxidative stress is established that, over time, can lead to the deterioration of cells and later organs and the entire body.

There are several ways that mitophagy is induced in mammalian cells. The PINK1 and Parkin pathway is, so far, the best characterized. This pathway starts in by deciphering the difference between healthy mitochondria and damaged mitochondria. A 64-kDa protein, PTEN-induced kinase 1 (PINK1), has been implicated to detect mitochondrial quality. PINK1 contains a mitochondrial targeting sequence (MTS) and is recruited to the mitochondria. In healthy mitochondria, PINK1 is imported through the outer membrane via the TOM complex, and partially through the inner mitochondrial membrane via the TIM complex, so it then spans the inner mitochondrial membrane. The process of import into the inner membrane is associated with the cleavage of PINK1 from 64-kDa into 60-kDa. Pink1 is then cleaved by PARL into 52-kDa. This new form of PINK1 is degraded by proteases within the mitochondria. This keeps the concentration of PINK1 in check in healthy mitochondria.

In unhealthy mitochondria, the interior mitochondrial membrane becomes depolarized. This membrane potential is necessary for the TIM-mediated protein import. In depolarized mitochondria, PINK1 is no longer imported into the inner membrane, is not cleaved by PARL and PINK1 concentration increases in the outer mitochondrial membrane. PINK1 can then recruit Parkin. It is thought that PINK1 phosphorylates Parkin ubiquitin at S65 which initiates Parkin recruitment at the mitochondria. Parkin is a cystolic E3 ubiquitin ligase 8. Once localized at the mitochondria, PINK1 phosphorylates Parkin at S65, homologous to the site where ubiquitin was phosphorylated, which activates Parkin by inducing dimerization and an active state. This allows for Parkin-mediated ubiquitination on other proteins.

Because of the PINK1 mediated recruitment to the mitochondrial surface, Parkin can ubiquitylate proteins in the outer mitochondrial membrane. Some of these proteins include Mfn1/Mfn2 and mitoNEET. The ubiquitylation of mitochondrial surface proteins brings in mitophagy initiating factors. Parkin promotes ubiquitin chain linkages on both K63 and K48. K48 Ubiquitination initiates degradation of the proteins, and could allow for passive mitochondrial degradation. K63 ubiquitination is thought to recruit autophagy adaptors LC3/GABARAP which will then lead to mitophagy. It is still unclear which proteins are necessary and sufficient for mitophagy, and how these proteins, once ubiquitylated, initiate mitophagy.

Other pathways that can induce mitophagy include mitophagy receptors on the outer mitochondrial membrane surface. These receptors include NIX1, BNIP3 and FUNDC1. All of these receptors contain LIR consensus sequences that bind LC3/GABARAP which can lead to the degradation of the mitochondria. In hypoxic conditions, BNIP3 is upregulated by HIF1. BNIP3 is then phosphorylated at its serine residues near the LIR sequence which promotes LC3 binding. FUNDCI is also hypoxia sensitive, although it is constitutively present at the outer mitochondrial membrane during normal conditions.

Research performed with yeast to identify genes that regulate longevity has disclosed that mitochondrial turnover is triggered by proteins. Additional studies have shown that in ΔUTH1 strains there was an inhibition of mitophagy, which occurred without affecting autophagy mechanisms. It also showed that Uth1p protein is necessary to move mitochondria to the vacuole. This suggested there is a specialized system for mitophagy. Other studies looked at AUP1, a mitochondrial phosphatase, and found Aup1 marks mitochondria for elimination. Another yeast protein associated with mitophagy is a mitochondrial inner membrane protein, Mdm38p/Mkh1p. This protein is part of the complex that exchanges K+/H+ ions across the inner membrane. Deletions to this protein cause swelling, a loss of membrane potential, and mitochondrial fragmentation. Further studies have shown that ATG32 (autophagy related gene 32) plays a crucial role in yeast mitophagy. It is localized to the mitochondria. Once mitophagy is initiated, Atg32 binds to Atg11 and the Atg32-associated mitochondria are transported to the vacuole. Atg32 silencing stops recruitment of autophagy machinery and mitochondrial degradation. Atg32 is not necessary for other forms of autophagy. All of these proteins likely play a role in maintaining healthy mitochondria, but mutations have shown that dysregulation can lead to a selective degradation of mitochondria.

For example, Parkinson's disease is a neurodegenerative disorder partially caused by the cell death of dopamine creating cells in the substantia nigra. There are several genetic mutations implicated in Parkinson's disease, including loss of function PINK1 and Parkin. Loss of function in these genes can lead to damaged mitochondrial accumulation and protein aggregates that can lead to cellular degeneration.

The mechanistic target of rapamycin (mTOR), also known as mammalian target of rapamycin or FK506-binding protein 12-rapamycin-associated protein 1 (FRAP1), is a protein that in humans is encoded by the MTOR gene. MTOR is a serine/threonine protein kinase that regulates cell growth, cell proliferation, cell motility, cell survival, protein synthesis, autophagy, transcription. MTOR belongs to the phosphatidylinositol 3-kinase-related kinase protein family and fibrosis.

Molecular genetic studies in yeast first identified FKBP12, TOR1, and TOR2 as the targets of rapamycin. These studies isolated rapamycin-resistant mutants of Saccharomyces cerevisiae and discovered that mutations in any of three genes can confer rapamycin resistance. Two of the genes were named TOR1 and TOR2 for targets of rapamycin (TOR). The third gene is FPR1, which encodes the yeast ortholog of FKBP12 binding protein in the TOR complexes. Loss of function mutations in FPR1 confer resistance to rapamycin, and also to FK506, providing genetic evidence the FKBP12-drug complexes are the active intracellular agents. Mutations in TOR1 or TOR2 that confer FKBP12-rapamycin resistance are a/the dominant gain of function mutations that alter single amino acid residues within the FRB domain and thereby block FKBP12-rapamycin binding. The mammalian target of rapamycin (mTOR) was identified and found to be the ortholog of the yeast Tor1/2 proteins and defined as the rapamycin target in mammals. mTOR was named based on the precedent that TOR was first discovered via genetic and molecular studies of rapamycin-resistant mutants of Saccharomyces cerevisiae that identified Tor1 and Tor2 as the targets of rapamycin.

mTOR integrates the input from upstream pathways, including insulin, growth factors (such as IGF-1 and IGF-2), and amino acids. mTOR also senses cellular nutrient, oxygen, and energy levels. The mTOR pathway is a central regulator of mammalian metabolism and physiology, with important roles in the function of tissues including liver, muscle, white and brown adipose tissue, and the brain, and is dysregulated in human diseases, such as diabetes, obesity, depression, and certain cancers. Rapamycin inhibits mTOR by associating with its intracellular receptor FKBP12. The FKBP12-rapamycin complex binds directly to the FKBP12-Rapamycin Binding (FRB) domain of mTOR, inhibiting its activity.

Figure 1D:
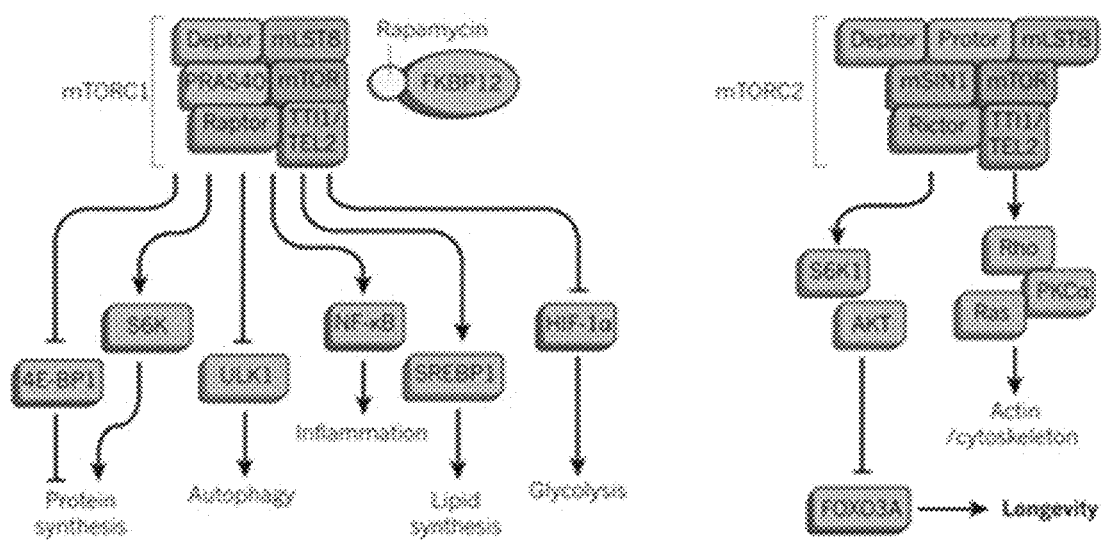
Figure 1E:
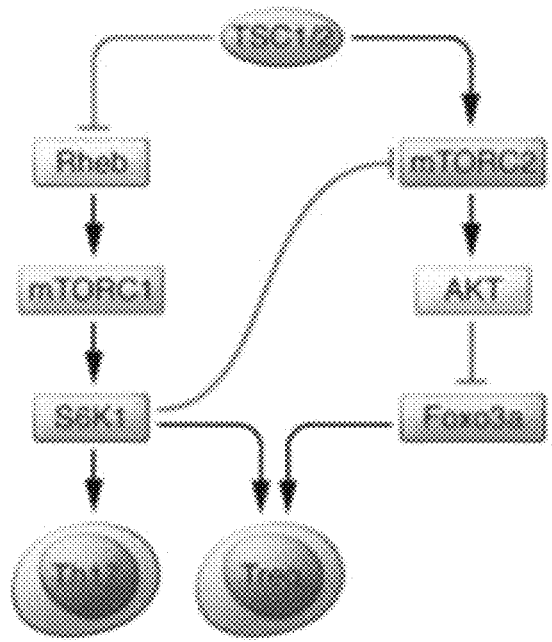
Figure 1F:
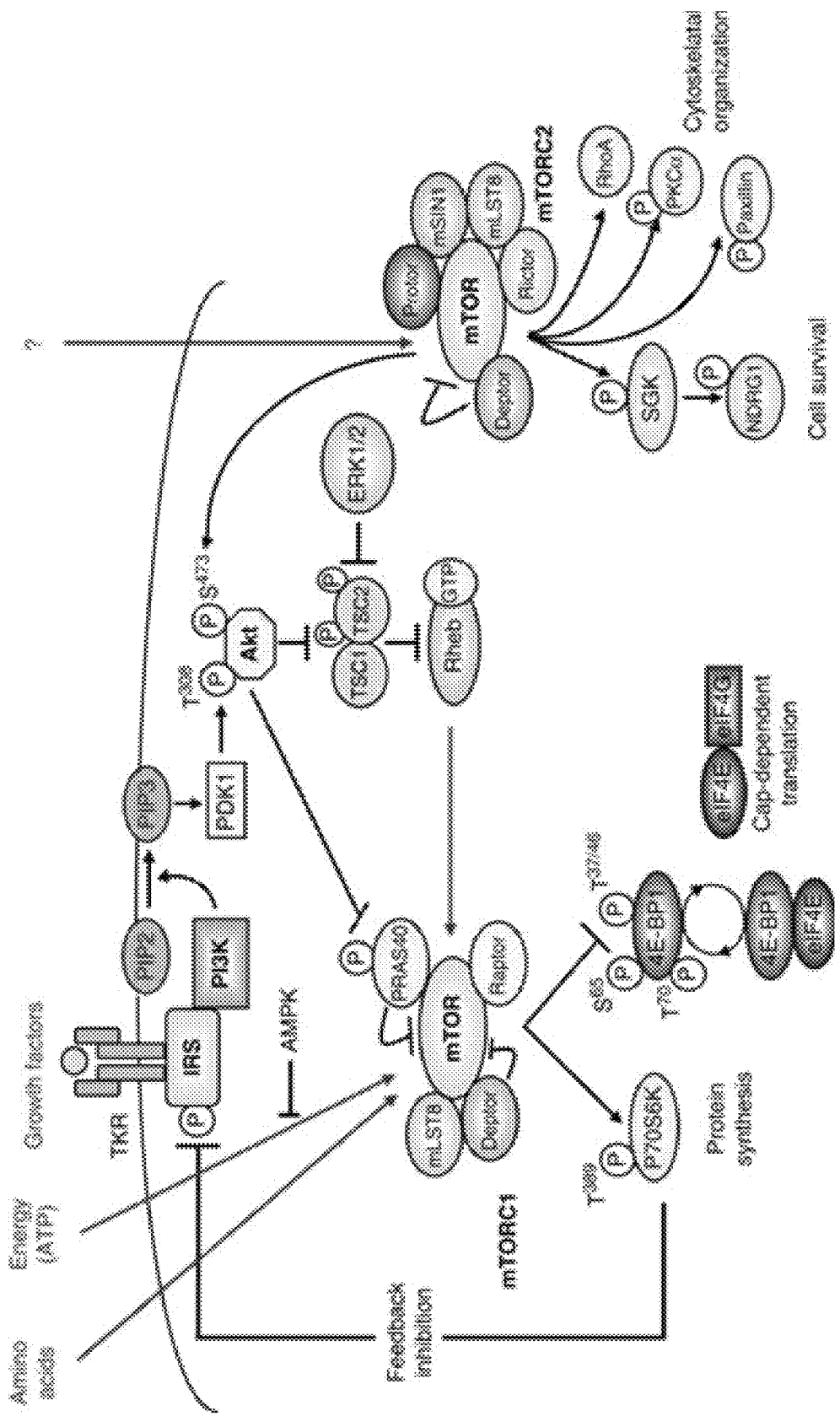

As shown in FIG. 1D-F, mTOR is the catalytic subunit of two structurally distinct complexes: mTORC1 and mTORC2. Both complexes localize to different subcellular compartments, thus affecting their activation and function.

mTOR Complex 1 (mTORC1) is composed of mTOR, regulatory-associated protein of MTOR (Raptor), mammalian lethal with SEC13 protein 8 (MLST8) and the non-core components PRAS40 and DEPTOR. This complex functions as a nutrient/energy/redox sensor and controls protein synthesis. The activity of mTORC1 is stimulated by insulin, growth factors, serum, phosphatidic acid, amino acids (particularly leucine), and oxidative stress.

mTOR Complex 2 (mTORC2) is composed of MTOR, rapamycin-insensitive companion of MTOR (RICTOR), MLST8, and mammalian stress-activated protein kinase interacting protein 1 (mSIN1). mTORC2 has been shown to function as an important regulator of the cytoskeleton through its stimulation of F-actin stress fibers, paxillin, RhoA, Rac1, Cdc42, and protein kinase C α (PKCα). mTORC2 also phosphorylates the serine/threonine protein kinase Akt/PKB at the serine residue S473, thus affecting metabolism and survival. Phosphorylation of the serine stimulates Akt phosphorylation at a threonine T308 residue by PDK1 and leads to full Akt activation.

Rapamycin inhibits mTORC1, and this appears to provide most of the beneficial effects of the drug (including life-span extension in animal studies). Rapamycin has a more complex effect on mTORC2, inhibiting it only in certain cell types under prolonged exposure. Disruption of mTORC2 produces the diabetic-like symptoms of decreased glucose tolerance and insensitivity to insulin.

Figure 1G:
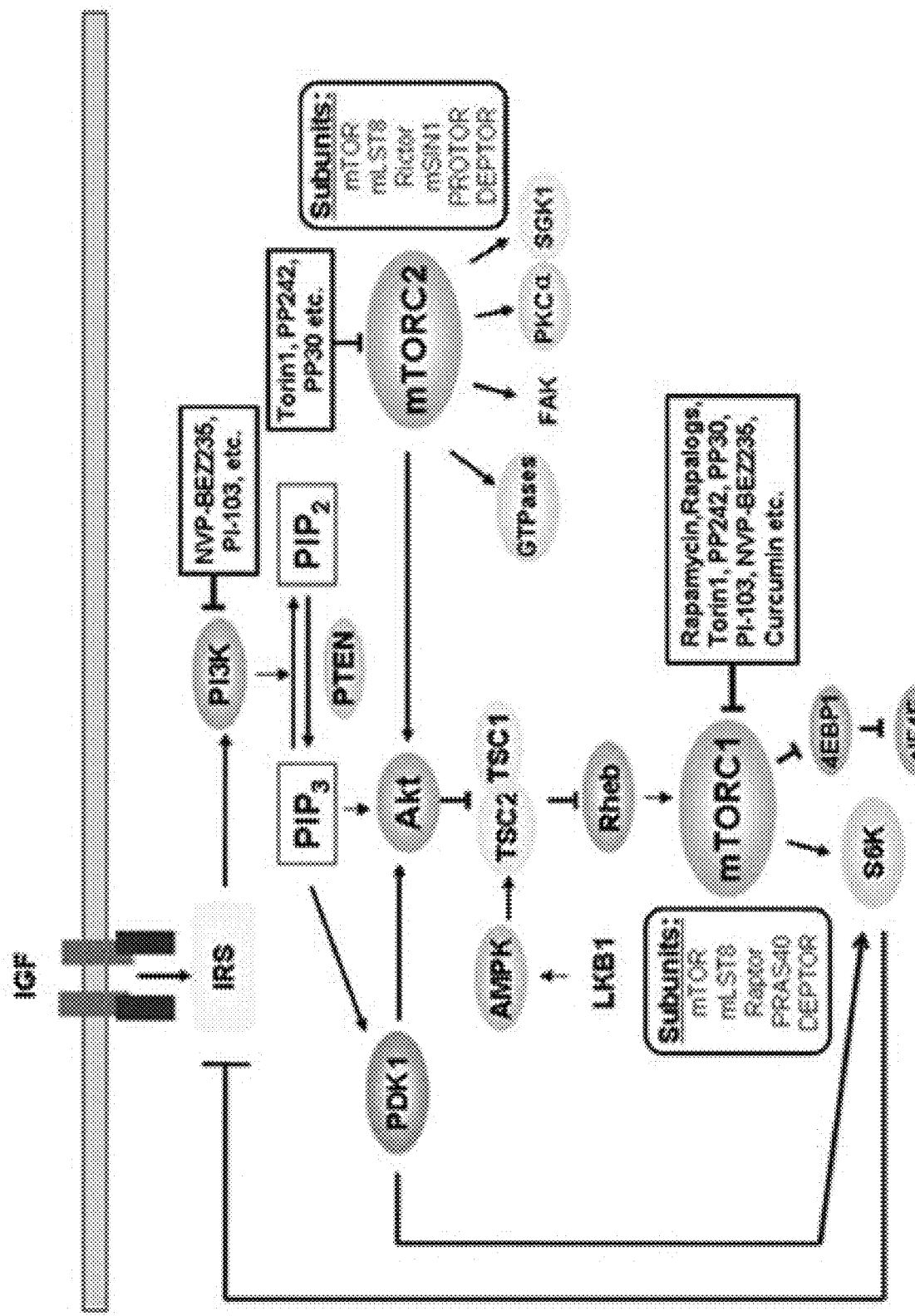

FIG. 1G illustrates the mTOR signaling pathway. Decreased TOR activity has been found to increase life span in S. cerevisiae, C. elegans, and D. melanogaster. The mTOR inhibitor rapamycin has been confirmed to increase lifespan in mice. Dietary regimes, like caloric restriction and methionine restriction, cause lifespan extension by decreasing mTOR activity. Some studies have suggested that mTOR signaling may increase during aging, at least in specific tissues like adipose tissue, and rapamycin may act in part by blocking this increase. An alternative theory is mTOR signaling is an example of antagonistic pleiotropy, and while high mTOR signaling is good during early life, it is maintained at an inappropriately high level in old age. CR and methionine restriction may act in part by limiting levels of essential amino acids including leucine and methionine, which are potent activators of mTOR. For example, the administration of leucine into the rat brain has been shown to decrease food intake and body weight via activation of the mTOR pathway.

According to the free radical theory of aging, reactive oxygen species cause damage of mitochondrial proteins and decrease of ATP production. Subsequently, via ATP sensitive AMPK, the mTOR pathway is inhibited and ATP consuming protein synthesis is downregulated, since mTORC1 initiates a phosphorylation cascade activating the ribosome. Hence, the proportion of damaged proteins is enhanced. Moreover, disruption of mTORC1 directly inhibits mitochondrial respiration. These positive feedbacks on the aging process are counteracted by protective mechanisms: Decreased mTOR activity (among other factors) upregulates glycolysis and removal of dysfunctional cellular components via autophagy.

mTOR signaling intersects with Alzheimer's disease (AD) pathology in several aspects, suggesting its potential role as a contributor to disease progression. In general, findings demonstrate mTOR signaling hyperactivity in AD brains. For example, postmortem studies of human AD brain reveal dysregulation in PTEN, Akt, S6K, and mTOR. mTOR signaling appears to be closely related to the presence of soluble amyloid beta (Aβ) and tau proteins, which aggregate and form two hallmarks of the disease, Aβ plaques and neurofibrillary tangles, respectively. In vitro studies have shown Aβ to be an activator of the PI3K/AKT pathway, which in turn activates mTOR. In addition, applying Aβ to N2K cells increases the expression of p70S6K, a downstream target of mTOR known to have higher expression in neurons that eventually develop neurofibrillary tangles. Chinese hamster ovary cells transfected with the 7PA2 familial AD mutation also exhibit increased mTOR activity compared to controls, and the hyperactivity is blocked using a gamma-secretase inhibitor. These in vitro studies suggest that increasing Aβ concentrations increases mTOR signaling; however, significantly large, cytotoxic Aβ concentrations are thought to decrease mTOR signaling.

Consistent with data observed in vitro, mTOR activity and activated p70S6K have been shown to be significantly increased in the cortex and hippocampus of animal models of AD compared to controls. Pharmacologic or genetic removal of the Aβ in animal models of AD eliminates the disruption in normal mTOR activity, pointing to the direct involvement of Aβ in mTOR signaling. In addition, by injecting Aβ oligomers into the hippocampi of normal mice, mTOR hyperactivity is observed. Cognitive impairments characteristic of AD appear to be mediated by the phosphorylation of PRAS-40, which detaches from and allows for the mTOR hyperactivity when it is phosphorylated; inhibiting PRAS-40 phosphorylation prevents Aβ-induced mTOR hyperactivity. Given these findings, the mTOR signaling pathway appears to be one mechanism of Aβ-induced toxicity in AD.

The hyperphosphorylation of tau proteins into neurofibrillary tangles is one hallmark of AD. p70S6K activation has been shown to promote tangle formation as well as mTOR hyperactivity through increased phosphorylation and reduced dephosphorylation. It has also been proposed that mTOR contributes to tau pathology by increasing the translation of tau and other proteins.

Synaptic plasticity is a key contributor to learning and memory, two processes that are severely impaired in AD patients. Translational control, or the maintenance of protein homeostasis, has been shown to be essential for neural plasticity and is regulated by mTOR. Both protein over- and under-production via mTOR activity seem to contribute to impaired learning and memory. Furthermore, given that deficits resulting from mTOR over activity can be alleviated through treatment with rapamycin, it is possible that mTOR plays an important role in affecting cognitive functioning through synaptic plasticity. Further evidence for mTOR activity in neurodegeneration comes from recent findings demonstrating that eIF2α-P, an upstream target of the mTOR pathway, mediates cell death in prion diseases through sustained translational inhibition.

Some evidence points to mTOR's role in reduced Aβ clearance as well. mTOR is a negative regulator of autophagy; therefore, hyperactivity in mTOR signaling should reduce Aβ clearance in the AD brain. Disruptions in autophagy may be a potential source of pathogenesis in protein misfolding diseases, including AD. Studies using mouse models of Huntington's disease demonstrate that treatment with rapamycin facilitates the clearance of huntingtin aggregates. Perhaps the same treatment may be useful in clearing Aβ deposits as well.

Over-activation of mTOR signaling significantly contributes to the initiation and development of tumors and mTOR activity was found to be deregulated in many types of cancer including breast, prostate, lung, melanoma, bladder, brain, and renal carcinomas. Reasons for constitutive activation are several. Among the most common are mutations in tumor suppressor PTEN gene. PTEN phosphatase negatively affects mTOR signaling through interfering with the effect of PI3K, an upstream effector of mTOR. Additionally, mTOR activity is deregulated in many cancers as a result of increased activity of PI3K or Akt. Similarly, overexpression of downstream mTOR effectors 4E-BP1, S6K and eIF4E leads to poor cancer prognosis. Also, mutations in TSC protein that inhibits the activity of mTOR may lead to a condition named tuberous sclerosis complex, which exhibits as benign lesions and increases the risk of renal cell carcinoma.

Increasing mTOR activity was shown to drive cell cycle progression and increase cell proliferation mainly thanks to its effect on protein synthesis. Moreover, active mTOR supports tumor growth also indirectly by inhibiting autophagy. Constitutively activated mTOR functions in supplying carcinoma cells with oxygen and nutrients by increasing the translation of HIF1A and supporting angiogenesis. mTOR also aids in another metabolic adaptation of cancerous cells to support their increased growth rate—activation of glycolytic metabolism. Akt2, a substrate of mTOR, specifically of mTORC2, upregulates expression of the glycolytic enzyme PKM2.

Natural promoters of mTOR include: protein, especially leucine; excess calories; excess carbs; exercise—activated in the brain, muscle and heart, but inhibited in liver and fat cells; orexin; IGF-1; insulin; testosterone; ghrelin in the hypothalamus; leptin in the hypothalamus; thyroid hormone in the hypothalamus and other cells; oxygen; ketamine, in the brain produces antidepressant effect; and IL-6 (R) in muscle and fat.

Natural Inhibitors of mTOR include: protein restriction; leucine restriction; glutamine restriction; methionine restriction; lysine restriction; arginine restriction; threonine restriction; isoleucine restriction; glutamine; calorie restriction; ketogenic diets; intermittent calorie restriction; exercise—inhibited in liver and fat cells, and activated in the brain, muscle and heart; cortisol/glucocorticoids; metformin by enhancing PRAS40's association with RAPTOR; NAC "profoundly reduced mTOR activity" in T cells in clinical trials; Resveratrol® increased the association between mTOR and its inhibitor, DEPTOR; Aspirin® colorectal cancer cells; cod liver/omega-3; extra virgin olive oil; EGCG/Tea– ATP-competitive inhibitor of both PI3K and mTOR; curcumin-separates raptor from mTOR, R-Lipoic Acid—also decreased p70S6 kinase; caffeine; fisetin-fat cells; apigenin (AMPK+, Akt−); quercetin (PI3K/Akt−, AMPK+, Hamartin+); genistein; DIM; ursolic acid; emodin found in Fo-Ti, resveratrol, rhubarb, and aloe; andrographis/andrographolide (PI3K/Akt−); pomegranate/ellagic acid; reishi; milk thistle/silymarin; oleanolic acid; anthocyanins/grape seed extract; astragalus (colon cancer); rhodiola; carnosine; plumbagin (black walnut hull); glucagon; and AICAR.

Diseases associated with mTOR activation include: Aging (R)—It is hypothesized that caloric restriction and methionine restriction, cause lifespan extension by decreasing mTOR activity; Cancer (R)—Breast (R); Autoimmune disease—increases Th1 and Th17; Depression (R); Diabetes (R), Obesity (R),—cause or effect; Alzheimer's (R); Macular degeneration (R); Kidney disease (R); Epilepsy (R); Autism (R)—mTOR prevents the 'pruning' or 'autophagy' of excitatory synapses in autism spectrum disorders; and Chronic pain (R); SLE (R).

But you can have scenarios where both AMPK is activated and mTOR is also activated because AMPK doesn't inhibit it directly; it inhibits another protein that directly increases mTOR. For example, Ghrelin, the hunger hormone, activates AMPK and mTOR in the hypothalamus. (R)

mTOR inhibitors, e.g. rapamycin, are already used to prevent transplant rejection. Rapamycin is also related to the therapy of glycogen storage disease (GSD). Some articles reported that rapamycin can inhibit mTORC1 so that the phosphorylation of GS (glycogen synthase) can be increased in skeletal muscle. This discovery represents a potential novel therapeutic approach for glycogen storage diseases that involve glycogen accumulation in muscle. Various natural compounds, including epigallocatechin gallate (EGCG), caffeine, curcumin, and resveratrol, have also been reported to inhibit mTOR when applied to isolated cells in culture.

Some mTOR inhibitors (e.g. temsirolimus, everolimus) are beginning to be used in the treatment of cancer. mTOR inhibitors may also be useful for treating several age-associated diseases including neurodegenerative diseases such as Alzheimer's disease and Parkinson's disease. Ridaforolimus is another mTOR inhibitor, currently in clinical development.

mTOR inhibitors may be used in a variety of therapies including protein synthesis and cell growth in the brain and skeletal muscle. Mitochondria are thought to be involved in Parkinson's disease. In spontaneous, usually aging related Parkinson's disease (non-genetically linked), the disease is commonly caused by dysfunctional mitochondria, cellular oxidative stress, autophagic alterations and the aggregation of proteins. These can lead to mitochondrial swelling and depolarization. It is important to keep the dysfunctional mitochondria regulated because all of these traits could be induced by mitochondrial dysfunction and can induce cell death. Disorders in energy creation by mitochondria can cause cellular degeneration, like those seen in the substantia nigra.

In some cases, cells can experience oxidative stress when there is an imbalance between ROS generated by oxidative phosphorylation and the cell's ability to detoxify ROS and/or repair damage caused by ROS. Oxidative stress can occur when there is an increase in production of ROS species or a decrease in a cell's ability to neutralize the excess ROS (e.g., by utilizing exogenous antioxidants and/or endogenous antioxidant systems). Oxidative stress can lead to damage of the mitochondria and/or other components of the cells. Oxidative stress can also lead to damage of proteins, lipids, and DNA, including DNA base damage and DNA strand breaks. Additionally, oxidative stress can lead to disruption of redox signaling and/or disruptions of normal mechanisms of cellular signaling. In other cases, oxidative stress has been linked to Asperger syndrome, attention deficit disorder, cancer, Parkinson's disease, Lafora disease, Alzheimer's disease, atherosclerosis, heart failure, myocardial infarction, fragile X syndrome, sickle cell disease, lichen planus, vitiligo, autism, infection, chronic fatigue syndrome, depression, neurodegenerative disease, Lou Gehrig's disease, Huntington's disease, and multiple sclerosis.

In some embodiments, various transcription factors are involved in upregulating one or more endogenous antioxidant systems. For example, transcription factors involved in upregulating one or more endogenous antioxidant systems can include Nrf2. Nrf2 is a transcription factor that is encoded in humans by the NFE2L2 gene and that regulates expression of antioxidants in response to oxidative damage caused by injury and inflammation. As described above, Nrf2 can be maintained in the cytoplasm of the cell under normal conditions and can be degraded fairly quickly. Under oxidative stress conditions, and/or through interaction with an inducer, Nrf2 can translocate to the nucleus to promote transcription of antioxidant genes. In some cases, Nrf2 can promote transcription of various antioxidant genes including Phase II genes, NQO1, GCL, sulfiredoxin 1 (SRXN1) and thioredoxin reductase 1 (TXNRD1), HO-1, GST family genes, and UDP-glucuronosyltransferase (UGT) family genes.

In some embodiments, transcription factors involved in upregulating one or more endogenous antioxidant systems can include an NF-κB complex. In other embodiments, NF-κB is involved in regulating other cellular processes such as inflammatory response, immune response, cell survival response, cellular proliferation, and in cellular response to stress, cytokines, ultraviolet radiation, oxidized LDL, and bacterial or viral antigens. In some cases, the NF-κB transcription factor is involved in cellular response to free radicals. NF-κB is often referred to as a rapid-acting primary transcription factor because of its ability to respond quickly to harmful cellular stimuli. NF-κB responds quickly to harmful cellular stimuli by being watchfully present in the cell in an inhibitor-bound inactive state. Once the cell detects harmful cellular stimuli, NF-κB can be quickly activated by degrading the bound inhibitor and freeing NF-κB to translocate to the nucleus to promote transcription of certain genes, including endogenous antioxidant system genes.

In some embodiments, transcription factors involved in upregulating one or more endogenous antioxidant systems can include the PPAR (peroxisome proliferator-activated receptors) family of transcription factors. In other embodiments, PPARs are involved in regulating other cellular processes such as regulation of cellular differentiation, development, metabolism, and tumorigenesis. The PPAR family includes at least the PPARα, PPARβ/δ, and PPARγ transcription factors. Members of the PPAR family are expressed in various tissues with PPARα expressed at least in liver, kidney, heart, muscle, and adipose tissue and with PPARβ/δ expressed at least in brain, adipose tissue, and skin. PPARγ can be expressed in three different forms, γ1, γ2, and γ3, with γ1 expressed in most tissues including heart, muscle, colon, kidney, pancreas, and spleen, with γ2 expressed mainly in adipose tissue, and with γ3 expressed in macrophages, large intestine, and white adipose tissue. In some cases, PPAR transcription factors can bind with certain receptors (e.g. retinoid X receptors) to promote transcription of certain genes, including endogenous antioxidant genes.

In some embodiments, upregulating compounds include any compound and/or mixture of compounds suitable for upregulating an endogenous antioxidant system. For example, upregulating compounds can include any compound and/or mixture of compounds that act as an inducer to upregulate an endogenous antioxidant system. In some cases, the upregulating compounds can include any compound that can translocate to the cytoplasm and/or nucleus to upregulate an endogenous antioxidant system. In other cases, the upregulating compounds can include any compound that can interact with one or more signaling molecules and/or signaling complexes to signal upregulation of an endogenous antioxidant system. In yet other cases, the upregulating compounds can include any compound that can directly interact with one or more signaling molecules and/or signaling complexes to signal upregulation of an endogenous antioxidant system. In some cases, the upregulating compounds can include any compound that can indirectly interact with one or more signaling molecules and/or signaling complexes to signal upregulation of an endogenous antioxidant system. In other cases, the upregulating compounds can include a nutrient, an herbal supplement, a plant extract, or any other similar compound. For example, the upregulating compounds can include one or more of bioflavonoid complex compounds, bromelain, choline bitartarate, coenzyme Q10, DHA, EPA, folic acid, grape seed extract, green tea extract, *Ginkgo biloba*, lycopene, lutein, milk thistle extract, omega-3 fatty acid, pantothenic acid, soy isoflavones, turmeric extract, soy extract, pea extract, potato extract, whey extract, phytoestrogens, and probiotics.

In some embodiments, the upregulating compounds include extracts derived from plants. Plant extracts and plant-based foods can comprise one or more upregulating compounds such as, but not limited to, phytochemicals. Phytochemicals can include chemical compounds that naturally occur in plants such as flavonoids or bioflavonoids. Bioflavonoids can comprise a 15-carbon skeleton with two phenyl rings and a heterocyclic ring. Bioflavonoids can include flavonoids, isoflavanoids, neoflavanoids, and anthoxanthins. Bioflavonoids can also include flavones (e.g., luteolin, apigenin, and tangeritin), flavonols (e.g., quercetin, kaempferol, myricetin, fisetin, galangin, isorhamnetin, pachypodol, rhamnazin, pyranoflavonols, and furanoflavonols), flavones (e.g., hesperetin, naringenin, eriodictyol, and homoeriodictyol), flavanonol (e.g., taxifolin and dihydrokamferol), and flavans (e.g., flavan-3-ols, anthocyanidins, and isoflavinoids). In other embodiments, upregulating compounds comprise extracts derived from edible plants. For example, upregulating compounds can comprise extracts derived from broccoli. Broccoli extract can include upregulating compounds such as glucoraphnin or sulforaphane. Grapes can contain bioflavonoids such as catechin, epicatachin, proanthocyanidins, and other related compounds. Berries can also contain different classes of upregulating compounds. In some cases, grape seed extract, milk thistle, and blueberries can contain upregulating compounds.

In some embodiments, the upregulating compounds include extracts and/or derivatives of the tea plant *Camellia sinensis*. The upregulating compounds can include extracts and/or derivatives of white tea, yellow tea, green tea, oolong tea, black tea, and post-fermented tea. Green tea extracts and derivatives can comprise upregulating compounds such as catechins (e.g., epicatechin (EC), epigallocatachin (EGC), epicatechin galate (ECG), and epigallocatechin gallate (EGCG)) and flavonols.

Figure 2A:
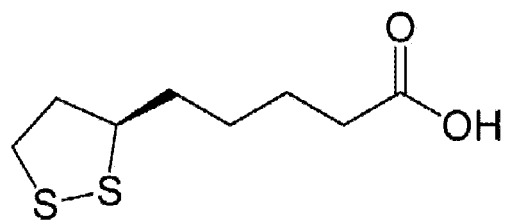
FIG. 2A illustrates a chemical structure of alpha lipoic acid.

In some embodiments, upregulating compounds comprise one or more of alpha lipoic acid, resveratrol, curcumin, EGCG, Olivol®, rutin, quercetin, and hesperetin. For example, the upregulating compounds can include lipoic acid. In some cases, lipoic acid can include one or more of alpha lipoic acid (ALA), racemic alpha lipoic acid, di-hydro alpha lipoic acid, R-(+) alpha lipoic acid, S-(−) alpha lipoic acid, R-(+) dihydro alpha lipoic acid, S-(−) dihydro alpha lipoic acid, metal salts thereof, esters thereof, or combinations thereof. FIG. 2A shows one chemical formula of alpha lipoic acid.

Figure 2B:
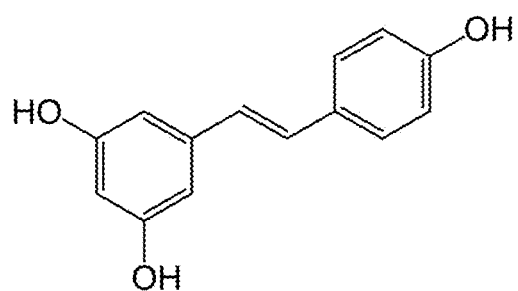
FIG. 2B illustrates a chemical structure of resveratrol.

In some embodiments, the upregulating compounds comprise resveratrol or a similar stilbenoid (e.g., pterostilbene). Resveratrol can include one or more of 3,5,4'-trihydroxy-trans-stilbene, 3,4',5-Stilbenetriol, trans-Resveratrol, (E)-5-(p-Hydroxystyryl)resorcinol, and (E)-5-(4-hydroxystyryl)benzene-1,3-diol. Resveratrol can include the cis-(Z) and/or trans-(E) isomers. Resveratrol can be derived from any suitable source including plant sources such as grapes or the skin of grapes, seeds of muscadine grapes, blueberries, raspberries, mulberries, bilberries, peanuts, Japanese knotweed, and cocoa powder. FIG. 2B shows one chemical formula of resveratrol.

Figure 2C:
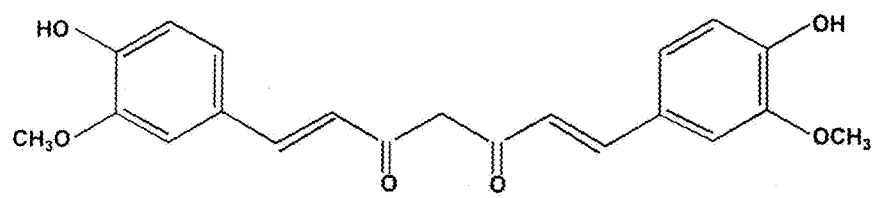
FIG. 2C illustrates a chemical structure of curcumin.

In some embodiments, the upregulating compounds comprise curcumin. In other embodiments, curcumin comprises one or more of curcumin and any other suitable curcuminoid. Curcumin can include any suitable tautomeric form of curcumin including, but not limited to, a 1,3-diketo form or an enol form. Curcumin can also include any suitable turmeric extract (e.g., desmethoxycurcumin and/or bis-desmethoxycurcumin. FIG. 2C shows one chemical formula of curcumin.

Figure 3A:
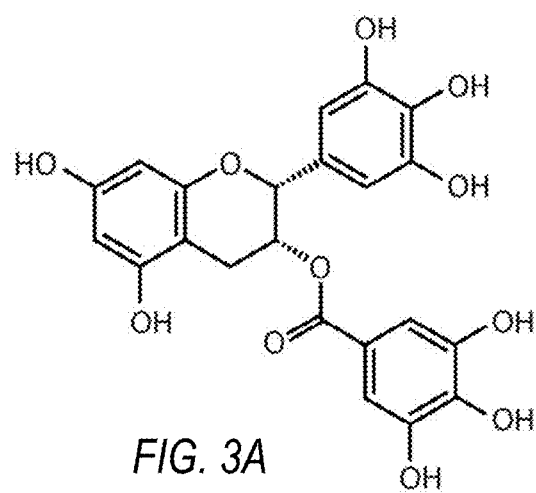
FIG. 3A epigallocatechin gallate (EGCG)

In some embodiments, the upregulating compounds comprise epigallocatechin gallate (EGCG). In other embodiments, the upregulating compounds comprise any suitable ester of epigallocatechin and gallic acid. EGCG can also include one or more of [(2R,3R)-5,7-dihydroxy-2-(3,4,5-trihydroxyphenyl)chroman-3-yl] 3,4,5-trihydroxybenzoate, (2R,3R)-5,7-dihydroxy-2-(3,4,5-trihydroxyphenyl)-3,4-dihydro-2H-1-benzopyran-3-yl 3,4,5-trihydroxybenzoate, and (−)-Epigallocatechin gallate. EGCG can be derived from any suitable source, include plant sources such as the leaves of white tea, the leaves of green tea, the leaves of black tea, apple skin, plums, onions, hazelnut, pecans, and carob. FIG. 3A shows one chemical formula of EGCG.

Figure 3B:
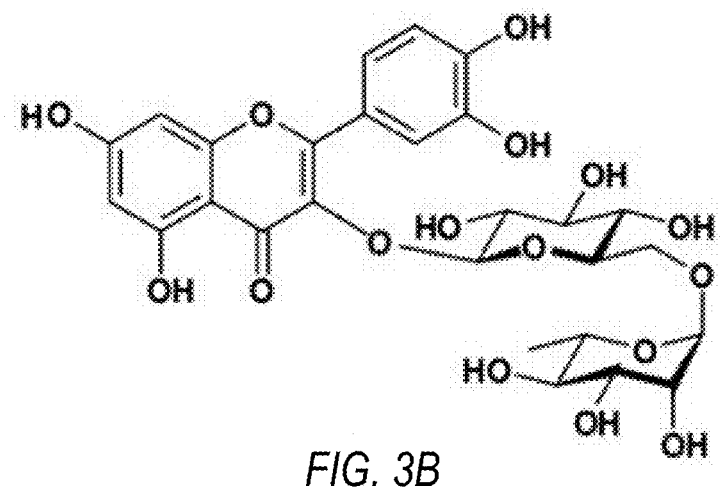
FIG. 3B illustrates a chemical structure of rutin.

In some embodiments, the upregulating compounds comprise rutin. In other embodiments, rutin comprises one or more of rutoside, quercetin-3-O-rutinoside, phytomelin, birutan, Eldrin, birutan forte, rutin trihydrate, globularicitrin, violaquercetin, and sophorin. Rutin can also include 2-(3,4-dihydroxyphenyl)-5,7-dihydroxy-3-{[(2S,3R,4 S,5S,6R)-3,4,5-trihydroxy-6-({[(2R,3R,4R,5R,6S)-3,4,5-trihydroxy-6-methyloxan-2-yl]oxy}methyl)oxan-2-yl]oxy}-4H-chromen-4-one and 2-(3,4-dihydroxyphenyl)-5,7-dihydroxy-3-[α-L-rhamnopyranosyl-(1→6)-β-D-glucopyranosyloxy]-4H-chromen-4-one. Rutin can be derived from any suitable source, include plant sources such as *Carpobrotus edulis, Ruta graveolens*, buckwheat, asparagus, fruit of the fava d'anata tree, fruits and flowers of the pagoda tree, oranges, grapefruits, lemons, limes, mulberry fruit, ash tree fruits, aronia berries, cranberries, and peaches. FIG. 3B shows one chemical formula of rutin.

In some embodiments, the upregulating compounds comprise Olivol®. In some cases, Olivol® can comprise any prepared extract of olive fruit. In other cases, Olivol® can comprise an extract of olive fruit prepared by methods disclosed in U.S. Pat. Nos. 6,358,542 and/or 6,361,803, the disclosures of which are hereby incorporated by reference. In yet other cases, Olivol® can be prepared by providing olive pulp by-product of olive oil production, extracting the pulp with a polar aqueous solvent to form an aqueous phase, passing the aqueous phase through a polymeric resin to trap antioxidants on the resin, washing the polymeric resin with polar organic solvent to release antioxidants from the resin to produce a solution of antioxidants in the polar organic solvent. Olivol® can comprise a phenolic antioxidant mixture of tyrosol, hydroxytyrosol, verbacoside, and other related compounds.

In some embodiments, the method of preparing Olivol® comprises providing an olive-based starting material such olive fruit, including green olives, black (ripe) olives, olives in intermediate stages of ripeness, olives that are over-ripe, whole olives, crushed or ground olive material, fresh olives, or partially or completely dried olives, or mixtures thereof. The starting material can also be the pulp from olive oil manufacturing that is prepared as a slurry and/or olive oil, regardless of purity or grade.

This starting material can be extracted with a polar aqueous solvent to form an aqueous phase containing antioxidant components extracted from the starting material. The extraction step can be carried out in any convenient fashion known to those skilled in the art. The starting material is then mixed with the polar aqueous solvent, whereby at least a portion of the antioxidant components contained in the starting material will be partitioned in the aqueous phase. The polar aqueous solvent can be water, or a mixture of water and any polar solvent that is water miscible, such as a water-miscible polar organic solvent. Suitable water-miscible polar organic solvents include $C_1$ to $C_4$ alcohols, esters, amides, ethers, nitrites and ketones. Preferred water-miscible organic solvents include $C_1$ to $C_4$ alcohols, particularly methanol, ethanol, propanol and isopropanol; acetone; dimethyl sulfoxide; dioxane; acetonitrile; DMF; and mixtures thereof. Most preferably, the polar aqueous solvent is a mixture of water and methanol, ethanol, acetonitrile, or acetone.

After the extraction is finished, the mixture will separate into at least two phases. Thus, when the starting material includes solid material, the mixture will separate at least into a solid phase and an aqueous phase, and generally into a solid phase, an oil phase, and an aqueous phase. When the starting material is olive oil, the mixture will separate into an oil phase and an aqueous phase. In either case, the aqueous phase is removed, such as by simple decantation, and the remaining phases discarded. Alternatively, the oil and/or solid phases can be extracted again with the same or a different polar aqueous solvent, and the aqueous phase from this second extraction also treated in accordance with the present method, preferably by combining with the aqueous phase from the first extraction. It should be appreciated that still further extractions of the solid and/or oil phases can be used, if desired.

The polar aqueous solvent can further include an acid that is soluble in the polar aqueous solvent and present in an amount such that the polar aqueous solvent has an acidic pH to improve extraction efficiency. Then, the antioxidant components in the aqueous phase are concentrated to form a solid antioxidant composition. The aqueous phase can be concentrated by allowing the polar aqueous solvent to evaporate, or by extracting the polar aqueous solvent with an organic solvent, such as ethyl acetate.

In some cases, a solid matrix can be used to separate the antioxidant components of the aqueous phase from the aqueous phase. The solid matrix can preferably be composed of a plurality of small particles having a large surface area, such as chromatographic beads such as a solid phase resin disposed in a bed or a chromatographic column. The solid matrix can include polymeric adsorbent material marketed under the trademark AMBERLITE® (e.g., macroreticulated crosslinked copolymer). The aqueous phase can be passed over the solid matrix material, such that at least a portion of the antioxidant components in the aqueous phase preferentially adheres to the solid matrix material. The adsorbed antioxidant components can be removed from the solid matrix material by washing the matrix with a solvent such as polar organic solvents, or aqueous mixtures of polar organic solvents, particularly $C_1$ to $C_4$ alcohols, acetone, ethyl acetate, acetonitrile, dioxane, and mixtures thereof. The eluted solution is a solution of the antioxidant composition in the polar organic solvent.

In some cases, the antioxidant composition solution is concentrated by removing at least a portion of the polar organic solvent to form a liquid concentrate. In other cases, the antioxidant composition solution is concentrated by removing most of the polar organic solvent to form a solid concentrate.

Figure 3C:
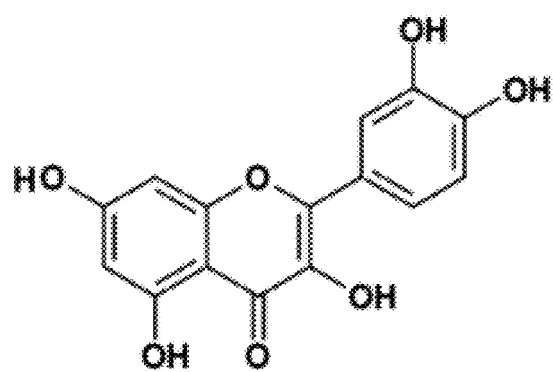
FIG. 3C illustrates a chemical structure of quercetin.

In some embodiments, the upregulating compounds comprise quercetin. In some cases quercetin can include 2-(3, 4-dihydroxyphenyl)-3,5,7-trihydroxy-4H-chromen-4-one. Quercetin can also include sophoretin, meletin, quercetine, xanthaurine, quercetol, quercetin, quertine, and flavin meletin. Quercetin can be derived from any suitable source including plant sources such as capers, radish leaves, carob fiber, dill, cilantro, Hungarian wax pepper, fennel leaves, red onion, radicchio, watercress, buckwheat, kale, chokeberry, cranberry, lingonberry, black plums, cow peas, sweet potato, blueberry, sea buckthorn berry, rowanberry, crowberry, prickly pear cactus fruits, red delicious apples, broccoli, bilberry, black tea, and green tea. FIG. 3C shows one chemical formula of quercetin.

Figure 4:
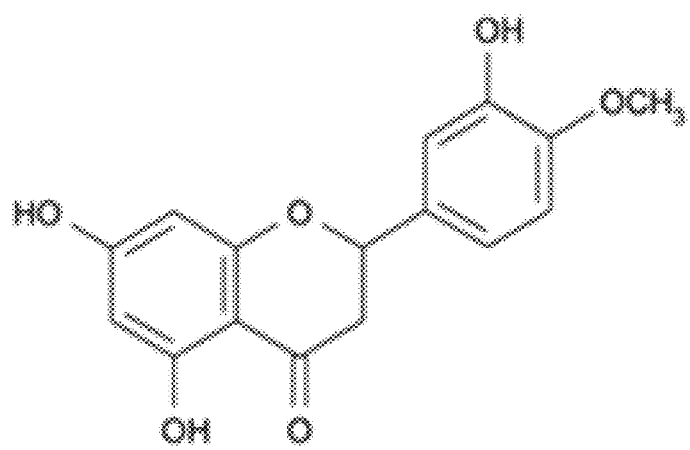
FIG. 4 illustrates a chemical structure of hesperetin.

In some embodiments, the upregulating compounds comprise hesperetin. In some cases, hesperetin can include (S)-2,3-Dihydro-5,7-dihydroxy-2-(3-hydroxy-4-methoxyphenyl)-4H-1-benzopyran-4-one. In other cases, hesperetin can include one or more of hesperidin, hesperetin 7-rutinoside, neohesperidin, 7-neohesperidoside, and hesperetin 7-rhamnoside. Hesperidin can be derived from any suitable source, including plant sources such as citrus fruits. FIG. 4 shows one chemical formula of hesperetin.

In some embodiments, the methods include methods for preparing composition(s) for reducing damage associated with oxidative phosphorylation. Without being bound by theory, it is thought that damage from oxidative phosphorylation, and in particular, damage from ROS generated as a by-product of oxidative phosphorylation, can be reduced by a composition comprising a mixture of an upregulating compound mixture, an exogenous antioxidant mixture, and a mineral mixture. In other embodiments, a composition comprising a mixture of an upregulating compound mixture, an exogenous antioxidant mixture, and a mineral mixture can work in conjunction to neutralize ROS and repair damage caused by ROS. For example, the composition comprising a mixture of an upregulating compound mixture, an exogenous antioxidant mixture can work in conjunction by: 1) allowing the cell to use its own defenses to neutralize ROS and/or repair damage caused by ROS by upregulating endogenous antioxidant systems with the upregulating compound mixture; 2) allowing the cell to use an exogenous source of antioxidants provided by the exogenous antioxidant mixture to neutralize ROS and/or repair damage caused by ROS; and 3) providing metal ions in the mineral mixture to act as cofactors for an antioxidant enzyme and/or one or more endogenous antioxidant systems. In yet other embodiments, the composition comprising a mixture of an upregulating compound mixture, an exogenous antioxidant mixture, and a mineral mixture can work synergistically to neutralize ROS and repair damage caused by ROS. For example, the composition comprising a mixture of an upregulating compound mixture, an exogenous antioxidant mixture can work synergistically by: 1) allowing the cell to use its own defenses to neutralize ROS and/or repair damage caused by ROS by upregulating endogenous antioxidant systems with the upregulating compound mixture; 2) allowing the cell to use an exogenous source of antioxidants provided by the exogenous antioxidant mixture to neutralize ROS and/or repair damage caused by ROS; and 3) providing metal ions in the mineral mixture to act as cofactors for an antioxidant enzyme and/or one or more endogenous antioxidant systems.

In some embodiments, the methods include methods of preparing nutritional supplements and compositions of nutritional supplements that comprise one or more of an upregulating compound mixture, an exogenous antioxidant mixture, and a mineral mixture. In other embodiments, the methods of preparing nutritional supplements and compositions of nutritional supplements comprise preparing nutritional supplements that comprise an upregulating compound mixture and an exogenous antioxidant mixture in a first part and a mineral mixture in a second part. In yet other embodiments, the methods of preparing nutritional supplements and compositions of nutritional supplements comprise preparing nutritional supplements that comprise an upregulating compound mixture in a first part, an exogenous antioxidant mixture in a second part, and a mineral mixture in a third part. In some embodiments, the upregulating compound mixture in a first part and the exogenous antioxidant mixture in a second part is combined in a single first vehicle and the mineral mixture in a third part is prepared as a single second vehicle.

In some embodiments, the upregulating compound mixture, the exogenous antioxidant mixture, and the mineral mixture are combined in the form of a single bilayer tablet or capsule. In these embodiments, the upregulating compound mixture and the exogenous antioxidant mixture are contained within a first part of the tablet or capsule and the mineral mixture is contained in a second part of the tablet or capsule. The first part and the second part can be maintained partially or completely separated from each other using any known separation technique. For example, these separation techniques can include forming the first part as a homogeneous first layer in the tablet and the second part as a homogeneous second layer in the table. The contact between the first layer and the second layer is minimized because they only contact each other at the interface between the first and second layers. In other embodiments, the separation technique includes using one or more of a coating, a film, and an inert layer to separate the first layer and second layers.

In some embodiments, a typical tablet shape comprises a caplet which has about the shape of a rectangular box. A bi-layer tablet in these configurations can comprise two or more of these boxes sandwiched together, with each box comprising a layer. An amount of material that is in contact at an interface between the layers can be estimated from an amount of material required to coat the entire tablet. The estimation is carried out by determining the amount of material required to coat the entire tablet and approximating that about half of this amount is an amount needed for the interface between the layers. Because the amount of material required to coat the entire tablet can range from about 1 to about 5% of the mass of the entire tablet, half of this amount can be approximated to range between about 0.5% and about 2.5% of the mass of the entire tablet. Therefore, about 0.5% and about 2.5% of the mass of the entire tablet can be approximated as the amount of material that is in contact at an interface between the layers.

In some embodiments, this separation technique includes forming the first part as a first layer in the tablet and the second part as a second layer in the tablet. Both the first and second layers are formed with a concentration gradient where one or more of the active ingredients in the bi-layer tablet is concentrated at an exterior of the tablet and minimized at the location at the interface where the two layers contact each other. In these embodiments, contact between the first layer and the second layer is limited to the interface between the first and second layers.

In some embodiments, this separation technique includes forming the first part as a first layer in the tablet and the second part as a second layer in the tablet. In these embodiments, the contact between the first layer and the second layer is reduced by providing a barrier between the two layers. In some configurations, the barrier can comprise a physical barrier, such as a film of the same material as the capsule that dissolves on contacting saliva. The physical barrier can have any thickness sufficient to prevent and/or reduce any contact between the two layers. In other configurations, the physical barrier can comprise a chemical component that prevents the two layers from reacting with each other. Examples of such chemical components include magnesium carbonate, potassium carbonate and sodium carbonate.

In other embodiments, the first layer is prepared as a first powder and the second layer is prepared as a second powder. In some cases, the first powder and the second powder can be combined. While the first and second portions can be mixed, the contact between the two ingredients can be minimized or eliminated by coating the first and/or second powders with a non-reactive layer having a thickness sufficient to prevent any substantial contact and/or reaction between the two ingredients. Examples of non-reactive layers include one or more of cellulose and food grade wax.

In some embodiments, the first layer is prepared as a first liquid and the second layer is prepared as a second liquid. A capsule can be prepared that contains a first, inner capsule containing one of these two liquids. The first capsule can be completely contained within a second, outer capsule that contains the other liquid. Thus, the two liquids are kept separated from each other by the inner capsule.

In some embodiments, the upregulating compound mixture and the exogenous antioxidant mixture are formulated as a single vehicle (e.g., a single tablet, dosage, or aliquot). While, the upregulating compound mixture can include any suitable upregulating compound, in some embodiments, the upregulating compound mixture includes one or more of the upregulating compounds described above (e.g., alpha lipoic acid, resveratrol, curcumin, EGCG, Olivol®, rutin, quercetin, and hesperetin). In other embodiments, the upregulating compound mixture includes one or more of bioflavonoids (e.g., sulforaphane precursors found in broccoli extracts, sulforaphane, glucoraffnin, and other suitable bioflavonoids). In yet other embodiments, the upregulating compound mixture comprises the compounds at the concentrations (e.g., mg of active ingredient (AI) and % by weight in mixture) as described in Table 1A.

TABLE 1A

| Ingredient | mg of AI | % by weight in mixture |
|---|---|---|
| Alpha Lipoic Acid | 25 | 22 |
| Resveratrol | 10 | 9 |
| Curcumin Phytosome Complex (Meriva- Bioavailable curcuminoids containing 3.25 mg curcuminoids) | 18 | 16 |
| Green Tea Extract (standardized to EGCG) | 17.5 | 15 |
| Olivol ® (Olive Fruit Extract) | 7.5 | 7 |
| Rutin | 10 | 9 |
| Quercetin | 15 | 13 |
| Hesperidin | 10 | 9 |

In some embodiments, one or more individual upregulating compounds comprise an overage amount above the minimum AI needed for the upregulating compound mixture. In some cases, the overage amount above the minimum AI needed for the mixture is configured to provide stability over time. For example, a certain overage amount, such as 10%, may be added to a minimum amount of an upregulating compound to maintain an amount equivalent to or above and AI amount in the event that there is a slight degradation of the upregulating compound over time. Any appropriated overage amount may be used from about 1% to about 100% and any subrange thereof. In other embodiments, the upregulating compound mixture comprises the compounds at the concentrations (e.g., mg of active ingredient (AI) and % by weight in mixture) and overage amounts as described in Table 1B.

TABLE 1B

| Nutrient/Ingredient | Minimum AI (mg/tablet) | Overage (%) | % AI in table | Total mg/tablet |
|---|---|---|---|---|
| Alpha Lipoic Acid | 25 | 35% | 100% | 33.750 |
| Resveratrol | 10 | 5% | 98% | 10.714 |
| Curcumin Phytosome Complex (Meriva- Bioavailable curcuminoids containing 3.25 mg curcuminoids) | 18 | 0% | 100% | 18.056 |
| Green Tea Extract (standardized to EGCG) | 17.5 | 0% | 100% | 17.500 |
| Olivol ® (Olive Fruit Extract) | 7.5 | 0% | 100% | 7.500 |
| Rutin | 10 | 0% | 95% | 10.526 |
| Quercetin Dihydrate | 15 | 0% | 95% | 15.789 |
| Hesperidin | 10 | 0% | 35% | 28.571 |

In some embodiments, alpha lipoic acid comprises between about 15 mg to about 35 mg of AI of the upregulating compound mixture. In other embodiments, alpha lipoic acid comprises between about 20 mg to about 30 mg of AI, or any intermediary value thereof, of the upregulating compound mixture. In yet other embodiments, alpha lipoic acid comprises up to about 5 mg, about 10 mg, about 15 mg, about 20 mg, about 25 mg, about 30 mg, about 35 mg of AI, or any intermediary value thereof, of the regulating compound mixture.

In some embodiments, alpha lipoic acid comprises between about 15% to about 35% by weight, or any intermediary value thereof, of the upregulating compound mixture. In other embodiments, alpha lipoic acid comprises between about 20% to about 25% by weight of the upregulating compound mixture. In yet other embodiments, alpha lipoic acid comprises up to about 5%, about 10%, about 15%, about 20%, about 25%, about 30%, about 35% by weight of the upregulating mixture, or any intermediary value thereof of the regulating compound mixture.

In some embodiments, resveratrol comprises between about 1 mg to about 25 mg of AI, or any intermediary value thereof, of the upregulating compound mixture. In other embodiments, resveratrol comprises between about 5 mg to about 15 mg, or any intermediary value thereof, of AI of the upregulating compound mixture. In yet other embodiments, resveratrol comprises up to about 1 mg, about 2 mg, about 5 mg, about 8 mg, about 9 mg, about 10 mg, about 12 mg, about 15 mg, or any intermediary value thereof of AI of the regulating compound mixture.

In some embodiments, resveratrol comprises between about 1% to about 25% by weight, or any intermediary value thereof, of the upregulating compound mixture. In other embodiments, resveratrol comprises between about 5% to about 15% by weight, or any intermediary value thereof, of the upregulating compound mixture. In yet other embodiments, resveratrol comprises up to about 1%, about 2%, about 5%, about 9%, about 10%, about 12%, about 15% by weight, or any intermediary value thereof, of the regulating compound mixture.

In some embodiments, curcumin comprises between about 2 mg to about 35 mg of AI of the upregulating compound mixture. In other embodiments, curcumin comprises between about 3 mg to about 15 mg, or any intermediary value thereof, of AI of the upregulating compound mixture. In yet other embodiments, curcumin comprises up to about 5 mg, about 10 mg, about 15 mg, about 18 mg, about 20 mg, about 22 mg, about 35 mg, about 30 mg, or any intermediary value thereof of AI of the regulating compound mixture.

In some embodiments, curcumin comprises between about 3% to about 35% by weight, or any intermediary value thereof, of the upregulating compound mixture. In other embodiments, curcumin comprises between about 5% to about 15% by weight, or any intermediary value thereof, of the upregulating compound mixture. In yet other embodiments, curcumin comprises up to about 1%, about 2%, about 3%, about 4%, about 5%, about 10%, about 15%, about 16%, about 20%, about 22%, about 25%, about 30%, about 35% by weight or any intermediary value thereof, of the regulating compound mixture.

In some embodiments, EGCG comprises between about 10 mg to about 35 mg of AI, or any intermediary value thereof, of the upregulating compound mixture. In other embodiments, EGCG comprises between about 15 mg to about 25 mg, or any intermediary value thereof, of AI of the upregulating compound mixture. In yet other embodiments, EGCG comprises up to about 5 mg, about 10 mg, about 15 mg, about 18 mg, about 20 mg, about 22 mg, about 35 mg, about 30 mg, or any intermediary value thereof of AI of the regulating compound mixture.

In some embodiments, EGCG comprises between about 10% to about 35% by weight, or any intermediary value thereof, of the upregulating compound mixture. In other embodiments, EGCG comprises between about 15% to about 25% by weight, or any intermediary value thereof, of the upregulating compound mixture. In yet other embodiments, EGCG comprises up to about 5%, about 10%, about 15%, about 16%, about 20%, about 22%, about 25%, about 30%, about 35% by weight or any intermediary value thereof, of the regulating compound mixture.

In some embodiments, Olivol® comprises between about 1 mg to about 20 mg, or any intermediary value thereof, of AI of the upregulating compound mixture. In other embodiments, Olivol® comprises between about 5 mg to about 15 mg, or any intermediary value thereof, of AI of the upregulating compound mixture. In yet other embodiments, Olivol® comprises up to about 1 mg, about 2 mg, about 5 mg, about 7.5 mg, about 10 mg, about 12 mg, about 15 mg, about 18 mg, about 20 mg, or any intermediary value thereof, of AI of the regulating compound mixture.

In some embodiments, Olivol® comprises between about 1% to about 15% by weight, or any intermediary value thereof, of the upregulating compound mixture. In other embodiments, Olivol® comprises between about 5% to about 12% by weight, or any intermediary value thereof, of the upregulating compound mixture. In yet other embodiments, Olivol® comprises up to about 1%, about 2%, about 5%, about 7%, about 8%, about 10%, about 12%, about 15%, about 18% by weight or any intermediary value thereof, of the regulating compound mixture.

In some embodiments, rutin comprises between about 1 mg to about 30 mg, or any intermediary value thereof, of AI of the upregulating compound mixture. In other embodiments, rutin comprises between about 5 mg to about 15 mg, or any intermediary value thereof, of AI of the upregulating compound mixture. In yet other embodiments, rutin comprises up to about 1 mg, about 2 mg, about 5 mg, about 8 mg, about 10 mg, about 12 mg, about 15 mg, about 20 mg, about 25 mg, about 30 mg, or any intermediary value thereof, of AI of the regulating compound mixture.

In some embodiments, rutin comprises between about 1% to about 30% by weight, or any intermediary value thereof, of the upregulating compound mixture. In other embodiments, rutin comprises between about 5% to about 25% by weight of the upregulating compound mixture. In yet other embodiments, rutin comprises up to about 5%, about 10%, about 13%, about 15%, about 18%, about 20%, about 22%, about 25%, about 30% by weight or any intermediary value thereof, of the regulating compound mixture.

In some embodiments, quercetin comprises between about 1 mg to about 30 mg, or any intermediary value thereof, of AI of the upregulating compound mixture. In other embodiments, quercetin comprises between about 10 mg to about 20 mg, or any intermediary value thereof, of AI of the upregulating compound mixture. In yet other embodiments, quercetin comprises up to about 1 mg, about 5 mg, about 10 mg, about 12 mg, about 15 mg, about 18 mg, about 20 mg, about 22 mg, about 25 mg, about 30 mg, or any intermediary value thereof, of AI of the regulating compound mixture.

In some embodiments, quercetin comprises between about 1% to about 30% by weight, or any intermediary value thereof, of the upregulating compound mixture. In other embodiments, quercetin comprises between about 5% to about 25% by weight, or any intermediary value thereof, of the upregulating compound mixture. In yet other embodiments, quercetin comprises up to about 5%, about 10%, about 13%, about 15%, about 18%, about 20%, about 22%, about 25%, about 30% by weight or any intermediary value thereof, of the regulating compound mixture.

While the exogenous antioxidant mixture can comprise any suitable exogenous antioxidant, at least in some embodiments the exogenous antioxidant mixture comprises one or more of mixed carotenoids, beta carotene, retinyl acetate, vitamin C, vitamin D3, vitamin E, mixed tocopherols, vitamin K1, vitamin K2, vitamin B1, vitamin B2, niacin, niacinamide, vitamin B6, folic acid, vitamin B12, biotin, pantothenic acid, inositol, choline bitartrate, coenzyme Q-10, lutein, and lycopene. In yet other embodiments, the exogenous antioxidant mixture comprises the compounds at the concentrations (e.g., mg of active ingredient (AI) and international unit (IU)) as described in Table 2A.

TABLE 2A

| Ingredient | mg of AI | IU |
|---|---|---|
| Mixed Carotenoids * | 0.1 | 100 IU |
| Beta carotene | 1.29 | 2150 IU |
| Retinyl Acetate | 0.258 | 750 IU |
| Vitamin C (Poly C) ** | 100 | |
| Vitamin D3 (Cholecalciferol) | 0.0125 | 500 IU |
| Vitamin E (d-alpha-tocopheryl succ.) | 41.3 | 50 IU |
| Mixed Tocopherols | 20 | |
| Vitamin K1 | 0.12 | |
| Vitamin K2 (menaquinone, MK-7) | 0.015 | |
| Vitamin B1 (thiamin HCL) | 7.5 | |
| Vitamin B2 (riboflavin) | 7.5 | |
| Niacin | 2.5 | |
| Niacinamide | 7.5 | |
| Vitamin B6 (pyridoxine HCL) | 8 | |
| Folic Acid | 0.15 | |
| Vitamin B12 (methylcobalamin) | 0.05 | |
| Biotin | 0.075 | |
| Pantothenic Acid | 22.5 | |
| Inositol | 32 | |
| Choline bitartrate | 62.5 | |
| Coenzyme Q-10 | 3 | |
| Lutein | 0.15 | |
| Lycopene | 0.25 | |

* Mixed carotenoids comprises a mixture of alpha-carotene, beta-carotene, gamma-carotene, and lycopene
** Vitamin (Poly C) was a mixture of calcium ascorbate, potassium ascorbate, magnesium ascorbate, and zinc ascorbate.

In some embodiments, one or more individual exogenous antioxidant compounds comprise an overage amount above the minimum AI needed for the exogenous antioxidant mixture. In some cases, the overage amount above the minimum AI needed for the mixture is configured to provide stability over time. For example, a certain overage amount, such as 10%, may be added to a minimum amount of an exogenous antioxidant compound to maintain an amount equivalent to or above and AI amount in the event that there is a slight degradation of the exogenous antioxidant compound over time. Any appropriated overage amount may be used from about 1% to about 100% and any subrange thereof. In other embodiments, the exogenous antioxidant compound mixture comprises the compounds at the concentrations (e.g., mg of active ingredient (AI) and % by weight in mixture) and overage amounts as described in Table 2B.

TABLE 2B

| Nutrient/Ingredient | Minimum AI (mg/tablet) | Overage (%) | % AI in table | Total mg/tablet |
|---|---|---|---|---|
| Mixed Carotenoids | 0.1 | 0% | 3.0% | 3.333 |
| alpha-carotene | | | | |
| Betacarotene | | | | |
| Gamma Carotene | | | | |
| lycopene | | | | |
| equivalent vitamin A from beta carotene (100 IU) | 116.6666667 | IU | | |
| Beta carotene (2150 IU tab) | 1.29 | 15% | 20.0% | 7.418 |
| Retinyl Acetate (750 IU) | 0.258 | 30% | 11% | 3.049 |
| Vitamin C (Poly C) | 100 | 5% | 80% | 131.250 |
| Calcium ascorbate equ Ca | 6.17 | | | |
| Potassium Ascorbate equiv. K | 6.96 | | | |
| Magnesium Ascorbate equiv. Mg | 1.22 | | | |
| Zinc Ascorbate equiv. Zn | 0.20 | | | |
| Vitamin D3 (Cholecalciferol) [500 IU/tab] | 0.0125 | 30% | 0.25% | 6.500 |

TABLE 2B-continued

| Nutrient/Ingredient | Minimum AI (mg/tablet) | Overage (%) | % AI in table | Total mg/tablet |
|---|---|---|---|---|
| Vitamin E (d-alpha-tocopheryl succ. 50 IU) | 41.3 | 4% | 98% | 43.829 |
| Mixed Tocopherols | 20 | 5% | 30% | 70.000 |
| Vitamin K1 | 0.12 | 40% | 1% | 16.800 |
| Vitamin K2 (menaquinone, MK-7) | 0.015 | 40% | 1.00% | 2.100 |
| Vitamin B1 (thiamin HCL) | 7.5 | 14% | 99% | 8.636 |
| Vitamin B2 (riboflavin) | 7.5 | 5% | 98% | 8.000 |
| Niacin | 2.5 | 8% | 99.8% | 2.705 |
| Niacinamide | 7.5 | 20% | 99.6% | 9.036 |
| Vitamin B6 (pyridoxine HCL) | 8 | 5% | 99% | 8.485 |
| Folic Acid | 0.15 | 20% | 10.0% | 1.800 |
| Vitamin B12 (cyanocobalamin) | 0.05 | 20% | 1.0% | 6.000 |
| Biotin | 0.075 | 10% | 1% | 8.250 |
| Pantothenic Acid | 22.5 | 5% | 90% | 26.250 |
| Inositol | 32 | 0% | 97% | 32.990 |
| Choline bitartrate | 62.5 | 0% | 98.7% | 63.323 |
| Coenzyme Q-10 | 3 | 10% | 100% | 3.300 |
| Lutein | 0.15 | 0% | 5% | 3.000 |
| Lycopene | 0.25 | 0% | 10% | 2.500 |

In some embodiments, the exogenous antioxidant mixture comprises individual exogenous antioxidant compounds at any suitable concentration. For example, mixed carotenoids can comprise between about 0.01 and 1 mg of AI or between 1 and about 200 IU, beta carotene can comprise between about 0.01 and 3 mg of AI or between 1000 and about 3000 IU, retinyl acetate can comprise between about 0.01 and 1 mg of AI or between 100 and about 1500 IU, vitamin C can comprise between about 10 and 200 mg of AI, vitamin D3 can comprise between about 0.001 and 1 mg of AI or between 100 and about 1000 IU, vitamin E can comprise between about 10 and 100 mg of AI or between 10 and about 150 IU, mixed tocopherols can comprise between about 1 and 50 mg of AI, vitamin K1 can comprise between about 0.01 and 1 mg of AI, vitamin K2 can comprise between about 0.0001 and 1 mg of AI, vitamin B1 can comprise between about 1 and 20 mg of AI, vitamin B2 can comprise between about 1 and 20 mg of AI, niacin can comprise between about 1 and 20 mg of AI, niacinamide can comprise between about 1 and 20 mg of AI, vitamin B6 can comprise between about 1 and 20 mg of AI, folic acid can comprise between about 0.01 and 2 mg of AI, vitamin B12 can comprise between about 0.001 and 2 mg of AI, biotin can comprise between about 0.001 and 2 mg of AI, pantothenic acid can comprise between about 1 and 50 mg of AI, inositol can comprise between about 1 and 100 mg of AI, choline bitartrate can comprise between about 1 and 200 mg of AI, coenzyme Q-10 can comprise between about 0.1 and 20 mg of AI, lutein can comprise between about 0.01 and 2 mg of AI, and lycopene can comprise between about 0.01 and 2 mg of AI.

In some embodiments, the mineral mixture comprises any suitable mineral, dietary mineral, metal ion, and/or mineral nutrient. In other embodiments, the mineral mixture comprises any suitable chemical entity that functions as a cofactor for a biomolecule, including biomolecules that comprise endogenous antioxidant systems. In some cases, cofactors can include chemical entities that are required for a protein's biological activity. In other cases, cofactors can include chemical entities that are required by endogenous antioxidant enzymes to function to reduce damage associated with oxidative phosphorylation. For example, an endogenous antioxidant enzyme, superoxide dismutase uses metal ion cofactors including copper, zinc, manganese, and/or iron.

While the mineral mixture can comprise any suitable mineral, at least in some embodiments the mineral mixture comprises one or more of calcium, calcium citrate, calcium ascorbate, magnesium, magnesium citrate, magnesium ascorbate, iodine, potassium iodine, zinc, zinc citrate, selenium, L-selenomethionine, sodium selenite, copper, copper gluconate, manganese, manganese gluconate, chromium, chromium polynicotinate, molybdenum, molybdenum citrate, boron, boron citrate, silicon, calcium silicate, vanadium, vanadium citrate, ultra-trace minerals, and N-acetyl-L-cysteine. In other embodiments, the mineral mixture comprises one or more of boron, calcium, chromium, copper, iodide, iron, magnesium, manganese, molybdenum, niacin, selenium, silicon, vanadium, zinc. In yet other embodiments, the mineral mixture comprises one or more of lithium, sodium, magnesium, potassium, calcium, vanadium, chromium, manganese, iron, cobalt, nickel, copper, zinc, molybdenum, boron, fluorine, silicon, selenium, sulfur, strontium, bromine, phosphorous, and iodine. In yet other embodiments, the mineral mixture comprises individual mineral compounds at the concentrations (e.g., mg of active ingredient (AI)) as described in Table 3A.

TABLE 3A

| Ingredient | mg of AI |
|---|---|
| Total Calcium | 56.25 |
| Calcium Citrate | 48.25 |
| Calcium Ascorbate[1,3] | 8 |
| Magnesium (citrate)[4] | 50.13 |
| Magnesium Ascorbate[2,3,4] | 6.12 |
| Iodine (potassium iodide) | 0.125 |
| Zinc (citrate) | 5.0 |
| Selenium (L-selenomethionine) | 0.0275 |
| Selenium (sodium selenite) | 0.0225 |
| Copper (gluconate) | 0.5 |
| Manganese (gluconate) | 0.5 |
| Chromium (polynicotinate) | 0.075 |
| Molybdenum (citrate) | 0.0125 |
| Boron (citrate) | 0.75 |
| Silicon (calcium silicate) | 1 |
| Vanadium (citrate) | 0.01 |
| Ultra-trace Minerals | 0.75 |
| N-acetyl-L-cysteine | 45 |

[1]Adds an equivalent of 70.9 mg of AI of vitamin C from calcium ascorbate
[2]Adds an equivalent of 79.1 mg of AI of vitamin C from magnesium ascorbate
[3]Total vitamin C equivalent equals 150 mg of AI
[4]Total magnesium content equals 56.25 mg of AI In other embodiments, the mineral mixture comprises individual mineral compounds at any suitable concentration. For example total calcium can comprise between about 10 and about 200 mg of AI, calcium citrate can comprise between about 1 and about 200 mg of AI, calcium ascorbate can comprise between about 1 and about 200 mg of AI, magnesium citrate can comprise between about 1 and about 200 mg of AI, magnesium ascorbate can comprise between about 0.1 and about 20 mg of AI, potassium iodide can comprise between about 0.001 and about 10 mg of AI, zinc citrate can comprise between about 0.1 and about 50 mg of AI, L-selenomethionine can comprise between about 0.001 and about 1 mg of AI, sodium selenite can comprise between about 0.001 and about 1 mg of AI, copper gluconate can comprise between about 0.01 and about 10 mg of AI, manganese gluconate can comprise between about 0.01 and about 10 mg of AI, chromium polynicotinate can comprise between about 0.001 and about 1 mg of AI, molybdenum citrate can comprise between about 0.001 and about 1 mg of AI, boron citrate can comprise between about 0.01 and about 10 mg of AI, calcium silicate can comprise between about 0.1 and about 10 mg of AI, vanadium citrate can comprise between about 0.001 and about 1 mg of AI, ultra-trace minerals can comprise between about 0.01 and about 10 mg of AI, and N-acetyl-L-cysteine can comprise between about 1 and about 100 mg of AI.

In some embodiments, one or more of the upregulating compound mixture, the exogenous antioxidant compound mixtures, and the mineral mixture is prepared as a solid formulation. For example, the upregulating compound mixture and the exogenous antioxidant mixture can be formulated as a single solid vehicle (e.g., a solid tablet) and the mineral mixture can be formulated as a separate single solid vehicle (e.g., a solid tablet). In other embodiments, one or more of the upregulating compound mixture, the exogenous antioxidant compound mixtures, and the mineral mixture is prepared as a liquid formulation (e.g., a liquid capsule). In some cases, the upregulating compound mixture and the exogenous antioxidant mixture are formulated as a single liquid vehicle (e.g., a liquid capsule) and the mineral mixture is formulated as a separate single liquid vehicle (e.g., a liquid capsule). In yet other embodiments, one or more of the upregulating compound mixture, the exogenous antioxidant compound mixtures and the mineral mixture is prepared as a solid granular formulation. For example, the upregulating compound mixture and the exogenous antioxidant mixture are formulated as a solid granular vehicle (e.g., a granular filled capsule) and the mineral mixture is formulated as a separate solid granular vehicle (e.g., a granular filled capsule).

In some embodiments, one or more of the upregulating compound mixture, the exogenous antioxidant compound mixtures, and the mineral mixture comprise any suitable additive. For example, a suitable additive can include binders, disintegrants, lubricants, flowing agents, flavorings, coatings, and any combination thereof. In some cases, binders can include microcrystalline cellulose, modified cellulose (e.g., Klucel), pre-gelatinized starch, or combinations thereof. In other cases, disintegrants can include croscarmellose sodium. Lubricant can include ascorbyl palmitate, vegetable fatty acid, or combinations thereof. Flowing agents can include silicon dioxide. Flavorings can include vanilla extract. In other embodiments, the/an additive includes one or more of maltodextrin, organic maltodextrin, lecithin, sunflower lecithin, palm olein, organic palm olein, guar gum, and organic guar gum. In yet other embodiments, additives comprise any suitable amount of the nutritional supplement.

In some embodiments, an additive mixture includes one or more of the excipients listed in Table 3B. In other embodiments, the additive mixture includes one or more of the excipients listed in Table 3B at the concentrations listed in Table 3B.

TABLE 3B

| Excipient | mg/tablet |
| --- | --- |
| Microcrystalline cellulose G | 303.288 |
| Modified Starch | 37.500 |
| Croscarmellose sodium | 28.500 |
| Ascorbyl palmitate | 9.750 |
| Silicon Dioxide | 10.000 |
| Clear film coating | 10.000 |
| Vanilla Extract | 1.300 |

In some embodiments, the nutritional supplement comprises the upregulating compounds listed in Table 1A and the exogenous antioxidant compounds listed in Table 2A. In other embodiments, the nutritional supplement comprises the upregulating compounds listed in Table 1A, the exogenous antioxidant compounds listed in Table 2A, and the minerals listed in Table 3A. In yet other embodiments, the nutritional supplement comprises the upregulating compounds listed in Table 1A, the exogenous antioxidant compounds listed in Table 2A, the minerals listed in Table 3A, and the excipients listed in Table 3B.

In some embodiments, the nutritional supplement comprises the upregulating compounds listed in Table 1B and the exogenous antioxidant compounds listed in Table 2B. In other embodiments, the nutritional supplement comprises the upregulating compounds listed in Table 1B, the exogenous antioxidant compounds listed in Table 2B, and the minerals listed in Table 3A. In yet other embodiments, the nutritional supplement comprises the upregulating compounds listed in Table 1B, the exogenous antioxidant compounds listed in Table 2B, the minerals listed in Table 3A, and the excipients listed in Table 3B.

The nutritional supplement can be prepared in any suitable form, including but not limited to, tablets, capsules, and powders. Solid diluents or carriers for the solid forms can be lipids, carbohydrates, proteins, mineral solids (e.g., starch, sucrose, kaolin, dicalcium phosphate, gelatin, acacia, corn syrup, corn starch, talc, and their combinations), and combinations thereof. Capsules can be formulated with known diluents and excipients, for example, edible oils, talc, calcium carbonate, calcium stearate, magnesium stearate, and combinations thereof. Liquid preparations for oral administration may be prepared in water or aqueous solutions which advantageously contain suspending agents, such as for example, sodium carboxymethylcellulose, methylcellulose, acacia, polyvinyl pyrrolidone, polyvinyl alcohol and combinations thereof.

In some embodiments, the nutritional supplements comprise preservatives in the nature of bactericidal and fungicidal agents including, but not limited to, parabens, chlorobutanol, benzyl alcohol, phenol, thimerosal, and the like. In some cases, the nutritional supplements can comprise isotonic agents such as sugars or sodium chloride. Carriers and vehicles include vegetable oils, water, ethanol, and polyols, for example, glycerol, propylene glycol, liquid polyethylene glycol, and the like.

The nutritional supplements can be prepared using any known method that will manufacture the desired form with the components in the desired concentrations. In some embodiments, the ingredients for one of the upregulating compound mixture, the exogenous antioxidant mixture, or mineral mixture are first weighed out and then transferred to a blender to be mixed. After the respective ingredients have been mixed in the blender, they are transferred to a hopper that feeds a tablet press that forms compressed tablets. The compressed tablets can be transferred to a coating pan where the coating solution is applied and the tablets are dried. The same process can be repeated for the remaining mixtures. Any other suitable additive as described above can be added to any of the mixtures. In other embodiments, any of the mixtures may be placed in a liquid carrier (e.g., mineral oil) to form a slurry for containment in a gel capsule.

In some embodiments, the nutritional supplement is administered to a human or an animal. While the nutritional supplement can be administered in any suitable manner, at least in some embodiments, the nutritional supplement is configured to be ingested by the human or the animal. In other embodiments, the method of administration can be adapted to the form of the nutritional supplement. For example, the nutritional supplement can be configured in the form of a tablet and/or capsule that can be swallowed by a human or an animal. In some cases, the nutritional supplement can be configured as a powder and/or a granular solid that can be added to a food or a beverage that can be consumed by the human or the animal. In other cases, the nutritional supplement can be configured as a liquid that is encapsulated in a gel capsule that can be swallowed or otherwise ingested. In yet other cases, the nutritional supplement can be configured as a liquid that is swallowed or otherwise ingested. In some cases, the nutritional supplement can be configured in a chewable form, such as a gelatin-based chewable dose.

In some embodiments, the nutritional supplement is administered in any suitable dosage. In other embodiments, the dosage of the nutritional supplement is modified based on one or more of an individual's weight, height, age, gender, pregnancy status, breastfeeding status, metabolism, health status, ethnicity, genetics, environment, diet, fitness level, cardiac health, body mass index, and/or lifestyle.

In some embodiments, the dosage of the upregulating compound mixture is a daily dose of between about 1 and 6 times the amount listed in Table 1. In other embodiments, the dosage of the upregulating compound mixture is a daily dosage of about 1, 2, 3, 4, 5, or 6 times the amount listed in Table 1. In yet other embodiments, the dosage of the upregulating compound mixture is about 4 times the amount listed in Table 1 for an adult. In some embodiments, the dosage of the upregulating compound mixture is about 2-3 times the amount listed in Table 1 for an adolescent. In other embodiments, the dosage of the upregulating compound mixture is about 0.5 to 1 times the amount listed in Table 1 for a child.

In some embodiments, the dosage of the endogenous antioxidant compound mixture is a daily dose of between about 1 and 6 times the amount listed in Table 2. In other embodiments, the dosage of the endogenous antioxidant compound mixture is a daily dosage of about 1, 2, 3, 4, 5, or 6 times the amount listed in Table 2. In yet other embodiments, the dosage of the endogenous antioxidant compound mixture is about 4 times the amount listed in Table 2 for an adult. In some embodiments, the dosage of the endogenous antioxidant compound mixture is about 2-3 times the amount listed in Table 2 for an adolescent. In other embodiments, the dosage of the endogenous antioxidant compound mixture is about 0.5 to 1 times the amount listed in Table 2 for a child.

In some embodiments, the dosage of the mineral compound mixture is a daily dose of between about 1 and 6 times the amount listed in Table 3. In other embodiments, the dosage of the mineral compound mixture is a daily dosage of about 1, 2, 3, 4, 5, or 6 times the amount listed in Table 3. In yet other embodiments, the dosage of the mineral compound mixture is about 4 times the amount listed in Table 3 for an adult. In some embodiments, the dosage of the mineral compound mixture is about 2-3 times the amount listed in Table 3 for an adolescent. In other embodiments, the dosage of the mineral compound mixture is about 0.5 to 1 times the amount listed in Table 3 for a child.

In some embodiments, the nutritional supplement is administered as a single daily dose. In other embodiments, the nutritional supplement is administered as multiple doses within a set period of time (e.g., a 24 hour period of time). In yet other embodiments, a single dose is divided into aliquots that are administered within a set period of time (e.g., a 24 hour period of time). In some embodiments, the nutritional supplement is administered as a single weekly dose. In other embodiments, the nutritional supplement is administered as a single monthly dose.

In some embodiments, the nutritional supplement is daily administered over a period of days. In other embodiments, the nutritional supplement is administered daily over a period of weeks. In yet other embodiments, the nutritional supplement is administered daily over a period of years.

In some embodiments, the nutritional supplement is administered to a human or an animal to reduce and/or prevent damage associated with oxidative phosphorylation by synergistically upregulating endogenous antioxidant systems, providing exogenous antioxidants, and providing minerals. In other embodiments, the nutritional supplement is administered to a human or an animal to upregulate endogenous antioxidant systems within the human or animal. In yet other embodiments, the nutritional supplement is administered to a human or an animal to upregulate endogenous antioxidant systems within the human or animal to reduce and/or prevent free radical damage. In some embodiments, the nutritional supplement is administered to a human or an animal to reduce and/or prevent damage by free radicals generated during oxidative phosphorylation. For example, the nutritional supplements can be administered to upregulate Phase II genes to reduce and/or prevent free radical damage. The nutritional supplements can also be administered to activate a transcription factor such as Nrf2, NF-κB, PPARα, PPARβ/δ, and/or PPARγ. The nutritional supplements can also be administered to promote transcription of endogenous antioxidant genes such as NQO1, GCL, sulfiredoxin 1 (SRXN1) and thioredoxin reductase 1 (TXNRD1), HO-1, GST family genes, and UDP-glucuronosyltransferase (UGT) family genes.

Example 1

Various receptor assays were carried out for test compounds corresponding to ingredients of the nutritional supplement composition. In general, the receptor assays utilized reporter cells that either expressed a native receptor or a receptor hybrid. The receptor hybrids were engineered so that the native N-terminal DNA binding domain (DBD) was replaced with a yeast Gal4 DBD. The reporter cells expressed a hybrid receptor comprising either the native receptor (Nrf2 and NF-κB) or the N-terminal Gal4 DNA binding domain fused to the ligand binding domain of the specific human nuclear receptor (PPARα, PPARδ, and PPARγ). The reporter gene (e.g., firefly luciferase) was functionally linked to either upstream receptor-specific response elements (GRE) or the Gal4 upstream activation sequence (UAS). A summary of the receptors, the reporter cells used for each particular receptor assay, and the reference compounds used to confirm performance of the receptor assays are indicated below in Table 4.

TABLE 4

| Receptor (gene symbol) | Receptor form | Reporter Vector | Host Cell Line | Reference Agonist | Reference Antagonist |
|---|---|---|---|---|---|
| PPARα (NR1C1) | Gal4 DBD hybrid receptor | Gal4 UAS-Luciferase | CHO | GW590735 | np |
| PPARδ (NR1C2) | Gal4 DBD hybrid receptor | Gal4 UAS-Luciferase | CHO | GW0742 | np |
| PPARγ (NR1C3) | Gal4 DBD hybrid receptor | Gal4 UAS-Luciferase | CHO | Rosiglitazone | np |
| Nrf2 | Native Receptor | ARE-Luciferase | CV1 | L-Sulforophane | np |
| NF-κB | Native NF-κB | NF-κB GRE-Luciferase | HEK293 | Phorbol ester (PMA) | na | np = assay not performed
na = not available
CHO = Chinese hamster ovary cell line
HEK293 = human embryonic kidney 293 cell line
CV1 = mammalian CV1 cell line The test compounds included alpha lipoic acid, resveratrol, curcumin, EGCG, Olivol®, rutin, quercetin, hesperetin, and a mixture of the all of the test compounds. A summary of the test compounds is shown below in Table 5.

TABLE 5

| Test Compound | Raw Material | Purity | Actual mass concentration | MW | Actual molar concentration | Effective molar concentration |
|---|---|---|---|---|---|---|
| Alpha lipoic acid | 155 mg/ml | 74% | 114.8 mg/ml | 206.32 | 550 mM | 550 μM |
| Resveratrol | 16 mg/ml | 47.6% | 7.6 mg/ml | 228.25 | 33.3 mM | 3.7 μM |
| Curcumin | 2.5 | 100% | 2.5 mg/ml | 368.69 | 6.79 mM | n/a |
| EGCG | 20 | 40% | 8 mg/ml | 458.372 | 17.5 mM | n/a |
| Olivol ® | 20 | 100% | 20 mg/ml | 154 | 129 mM | n/a |
| Rutin | 30 | 100% | 30 mg/ml | 610.50 | 49.1 mM | n/a |
| Quercetin | 68 | 100% | 68 mg/ml | 302.2 | 22.5 mM | 7.5 μM |
| Hesperetin | 2.5 | 35% | 0.875 mg/ml | 610.50 | 1.43 mM | n/a |
| Mixture | 7.41 | n/a | n/a | n/a | n/a | n/a |

The test compounds were assayed for activity against human PPARα, PPARδ, PPARγ, and Nrf2 in agonist mode. For the agonist assays, separate suspensions of each of the PPARα, PPARδ, PPARγ, Nrf2 reporter cells were prepared in cell recovery medium containing 10% charcoal stripped fetal bovine serum. Next, 100 μL aliquots of the PPARα reporter cells were dispensed into each test well of a white 96-well assay plate. Assay plates with PPARδ, PPARγ, and Nrf2 reporter cells were prepared in similar fashion. Dilutions of the test compounds were serially diluted using compound screening medium containing 10% charcoal stripped fetal bovine serum to generate 2x-concentration test compound samples. Control solutions of known agonists of the each of the PPARα, PPARδ, PPARγ, and Nrf2 receptors were prepared along with a vehicle control. 100 μL aliquots of the 2x-concentration test compound samples, control solutions, and vehicle control were dispensed into separate test wells of each white 96-well assay plate in triplicate. The assay plates were incubated at 37° C. for 24 h. After incubation, media was removed from each test well while leaving behind the receptor cells and 100 μL of luciferase detection reagent was added to each test well and emitted light from each test well of the assay plates was detected. The emitted light from each test well was recorded as relative light units (RLU).

The test compounds were assayed for activity against human NF-κB in antagonist mode. For the agonist assays, a suspension of NF-κB reporter cells were prepared in a cell recovery medium containing 10% charcoal stripped fetal bovine serum. Next, 100 μL aliquots of the NF-κB reporter cells were dispensed into each test well of a white 96-well assay plate. Dilutions of the test compounds were serially diluted using compound screening medium containing 10% charcoal stripped fetal bovine serum to generate 2x-concentration test compound samples. A vehicle control was prepared. 100 μL aliquots of the 2x-concentration test compound samples and vehicle control were dispensed into separate test wells of the white 96-well assay plate in triplicate. The assay plate was incubated at 37° C. for 24 h. After incubation, media was removed from each test well while leaving behind the receptor cells. The receptor cells were rinsed once with live cell multiplex buffer, live cell multiplex substrate added, and the plate incubated at 37° C. for 30 minutes. After incubation, fluorescence was measured to determine a relative number of live cells per test well. The live cell multiplex substrate was then removed and discarded and 100 μL luciferase detection reagent was added to each test well and emitted light from each test well of the assay plate was detected. The emitted light from each test well was recorded as relative light units (RLU).

The recorded RLU for each test well was correlated to the respective nuclear receptor activities by using the RLU of each dilution of each test compound, the RLU of the control solutions of known agonists, and the RLU of the vehicle controls. The fold-activation was determined for the agonist assays and the percent inhibition and percent live cells were determined for the antagonist assays. The fold-activation for the agonist assays for each serial dilution of each test compound is shown below in Table 6.

TABLE 6

| Test Compound | Active Ingredient concentration in µg/ml | PPARα Fold-Activation | PPARδ Fold-Activation | PPARγ Fold-Activation | Nrf2 Fold-Activation |
|---|---|---|---|---|---|
| Vehicle (DMSO) | 0.10% | 1.0 | 1.0 | 1.0 | 1.0 |
| Alpha lipoic acid | 0.47 | 1.2 | 1.4 | 0.85 | 1.0 |
|  | 1.42 | 1.4 | 1.5 | 1.1 | 1.4 |
|  | 4.25 | 1.3 | 1.1 | 1.1 | 1.4 |
|  | 12.7 | 1.2 | 0.80 | 1.3 | 1.5 |
|  | 38.23 | 1.5 | 0.52 | 1.4 | 1.5 |
|  | 114.70 | 2.3 | 0.29 | 3.4 | 2.4 |
| Resveratrol | 0.031 | 1.3 | 1.6 | 1.1 | 1.5 |
|  | 0.094 | 1.3 | 1.1 | 1.0 | 1.2 |
|  | 0.28 | 1.2 | 1.4 | 0.95 | 1.2 |
|  | 0.85 | 1.7 | 1.5 | 1.3 | 4.9 |
|  | 2.5 | 1.8 | 2.1 | 3.1 | 4.0 |
|  | 7.62 | 1.3 | 1.5 | 7.3 | 3.3 |
| Curcumin | 0.007 | 1.3 | 1.2 | 1.0 | 1.6 |
|  | 0.022 | 1.3 | 1.2 | 1.0 | 1.7 |
|  | 0.067 | 1.3 | 1.0 | 0.95 | 1.4 |
|  | 0.20 | 1.1 | 1.2 | 0.96 | 0.96 |
|  | 0.60 | 1.0 | 1.3 | 0.90 | 1.0 |
|  | 1.81 | 0.86 | 1.0 | 1.1 | 1.6 |
| EGCG | 0.033 | 1.4 | 1.3 | 1.1 | 1.4 |
|  | 0.098 | 1.3 | 1.4 | 1.0 | 1.3 |
|  | 0.30 | 1.4 | 1.2 | 1.0 | 1.2 |
|  | 0.89 | 1.2 | 1.3 | 0.95 | 1.2 |
|  | 2.67 | 1.1 | 1.1 | 0.85 | 1.3 |
|  | 8 | 0.85 | 0.48 | 0.53 | 0.74 |
| Olivol ® | 0.8 | 1.4 | 0.90 | 0.78 | 1.0 |
|  | 0.25 | 1.5 | 1.6 | 1.0 | 1.4 |
|  | 0.74 | 1.3 | 1.1 | 1.1 | 1.4 |
|  | 2.2 | 1.5 | 1.6 | 1.1 | 1.4 |
|  | 6.7 | 1.4 | 1.5 | 1.0 | 1.4 |
|  | 20 | 1.0 | 0.84 | 1.0 | 1.3 |
| Rutin | 0.12 | 1.1 | 0.95 | 0.91 | 1.4 |
|  | 0.37 | 1.1 | 1.0 | 0.78 | 1.1 |
|  | 1.11 | 0.94 | 1.3 | 0.86 | 0.85 |
|  | 3.3 | 0.99 | 1.1 | 1.0 | 1.4 |
|  | 10.0 | 1.0 | 1.3 | 1.2 | 1.4 |
|  | 30 | 1.0 | 1.2 | 1.3 | 1.5 |
| Quercetin | 0.28 | 1.5 | 1.1 | 1.1 | 1.5 |
|  | 0.84 | 1.2 | 1.0 | 1.0 | 1.4 |
|  | 2.5 | 1.3 | 1.2 | 1.0 | 1.8 |
|  | 7.6 | 1.1 | 0.76 | 1.0 | 0.87 |
|  | 23 | 1.2 | 0.51 | 1.5 | 3.2* |
|  | 68 | 0.89 | 0.26 | 1.4 | 4.6* |
| Hesperetin | 0.014 | 1.0 | 1.0 | 1.1 | 1.6 |
|  | 0.043 | 1.4 | 1.1 | 1.0 | 1.4 |
|  | 0.130 | 1.1 | 1.1 | 1.1 | 1.6 |
|  | 0.389 | 1.2 | 1.0 | 1.1 | 1.3 |
|  | 1.167 | 1.0 | 1.1 | 1.1 | 1.5 |
|  | 3.5 | 0.79 | 0.89 | 0.55 | 0.94 |

*Greater than 2-fold activation deemed to be statistically significant

The fold-activation for the agonist assays for each serial dilution of the mixture is shown below in Table 7. The undiluted mixture comprised 1.22 mg/ml of alpha lipoic acid, 0.49 mg/ml of resveratrol, 0.079 mg/ml of curcumin, 0.34 mg/ml of EGCG, 0.37 mg/ml of Olivol®, 0.49 mg/ml of rutin, 7.36 mg/ml of quercetin, and 0.49 mg/ml of hesperetin.

TABLE 7

| Test Compound | Fold Dilution | PPARα Fold-Activation | PPARδ Fold-Activation | PPARγ Fold-Activation | Nrf2 Fold-Activation |
|---|---|---|---|---|---|
| Mixture | 243,000 | 1.2 | 1.3 | 0.91 | 1.0 |
|  | 81,000 | 1.1 | 1.1 | 1.0 | 1.4 |
|  | 27,000 | 1.3 | 1.3 | 1.0 | 1.4 |
|  | 9,000 | 1.2 | 1.4 | 1.1 | 2.0* |
|  | 3,000 | 1.5 | 1.2 | 1.2 | 3.5* |
|  | 1,000 | 1.5 | 1.2 | 2.0* | 2.7* |

*Greater than 2-fold activation deemed to be statistically significant

The percent inhibition and percent live cell for the antagonist assays for each serial dilution of each test compound are shown below in Table 8.

TABLE 8

| Test Compound | Active Ingredient concentration in µg/ml | NF-κB % Inhibition | NF-κB % Live Cell |
|---|---|---|---|
| Vehicle (DMSO) | 0.10% | 0.0 | 0.0 |
| Alpha lipoic acid | 0.47 | 4.4 | 100 |
| | 1.42 | 3.1 | 100 |
| | 4.25 | −0.70 | 104 |
| | 12.7 | −6.1 | 102 |
| | 38.23 | 5.9 | 104 |
| | 114.70 | −14 | 105 |
| Resveratrol | 0.031 | −9.7 | 107 |
| | 0.09 | 24 | 105 |
| | 0.28 | 1.7 | 100 |
| | 0.85 | −2.6 | 100 |
| | 2.54 | −50 | 102 |
| | 1.81 | −28 | 99 |
| Curcumin | 0.007 | −10 | 105 |
| | 0.022 | −3.4 | 105 |
| | 0.067 | −0.29 | 106 |
| | 0.20 | 22 | 105 |
| | 0.60 | 30 | 99 |
| | 1.81 | 51** | 97 |
| EGCG | 0.033 | 10 | 102 |
| | 0.098 | 18 | 101 |
| | 0.30 | 0.10 | 105 |
| | 0.89 | 8.4 | 104 |
| | 2.67 | −15 | 106 |
| | 8 | −29 | 107 |
| Olivol® | 0.8 | 27 | 99 |
| | 0.25 | −3.8 | 98 |
| | 0.74 | −2.2 | 100 |
| | 2.2 | 13 | 97 |
| | 6.7 | 13 | 99 |
| | 20 | 16 | 98 |
| Rutin | 0.12 | −3.4 | 102 |
| | 0.37 | 2.7 | 102 |
| | 1.11 | 10 | 99 |
| | 3.3 | −2.3 | 98 |
| | 10.0 | −11 | 101 |
| | 30 | −15 | 97 |
| Quercetin | 0.28 | −12 | 103 |
| | 0.84 | −6 | 99 |
| | 2.5 | −12 | 103 |
| | 7.6 | 18 | 99 |
| | 23 | 58** | 97 |
| | 68 | 85** | 77*** |
| Hesperetin | 0.014 | −6.8 | 101 |
| | 0.043 | −11 | 98 |
| | 0.13 | −2.5 | 100 |
| | 0.389 | −2.1 | 99 |
| | 1.167 | 14 | 98 |
| | 3.5 | 39 | 96 |

**Greater than 2-fold inhibition deemed to be statistically significant
***Possible cytotoxicity The fold-activation for the antagonist assays for each serial dilution of the mixture is shown below in Table 9A. The undiluted mixture comprised 1.22 mg/ml of alpha lipoic acid, 0.49 mg/ml of resveratrol, 0.079 mg/ml of curcumin, 0.34 mg/ml of EGCG, 0.37 mg/ml of Olivol®, 0.49 mg/ml of rutin, 7.36 mg/ml of quercetin, and 0.49 mg/ml of Hesperetin.

TABLE 9A

| Test Compound | Fold Dilution | NF-κB % Inhibition | NF-κB % Live Cell |
|---|---|---|---|
| Mixture | 243,000 | 20 | 96 |
| | 81,000 | 11 | 98 |
| | 27,000 | 11 | 98 |
| | 9,000 | −4.7 | 96 |
| | 3,000 | −40 | 97 |
| | 1,000 | 1.9 | 97 |

Figure 5:
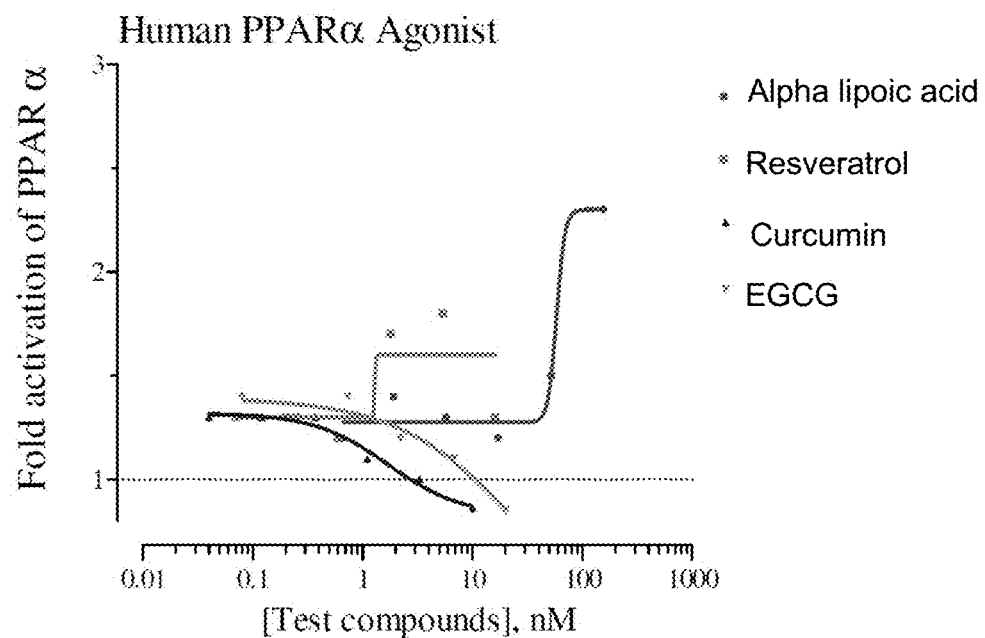
FIG. 5 illustrates fold-activation of PPARα for alpha lipoic acid, resveratrol, curcumin, and EGCG.
Figure 6:
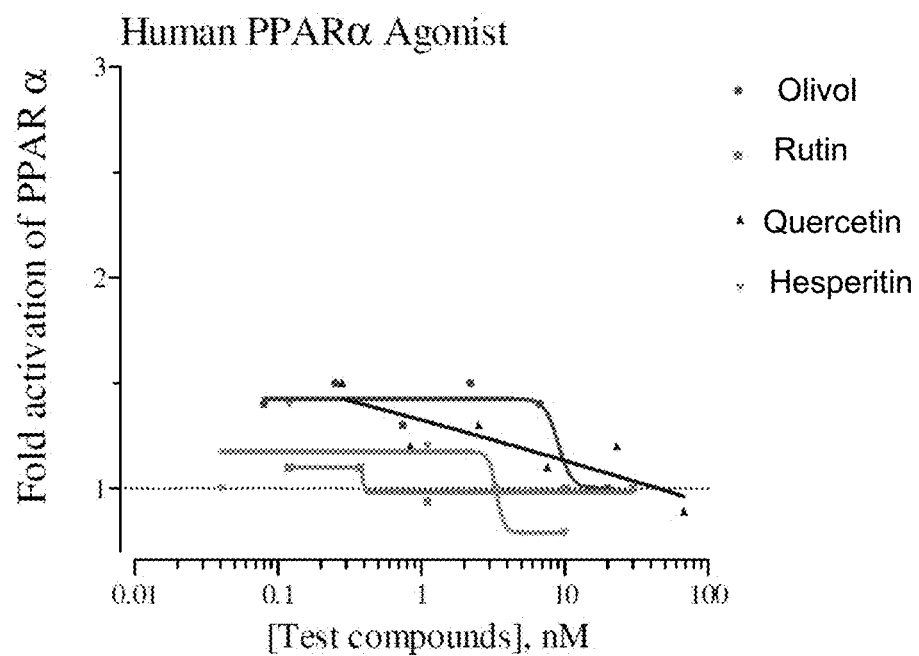
FIG. 6 illustrates fold-activation of PPARα for Olivol®, rutin, quercetin, and hesperetin.
Figure 7:
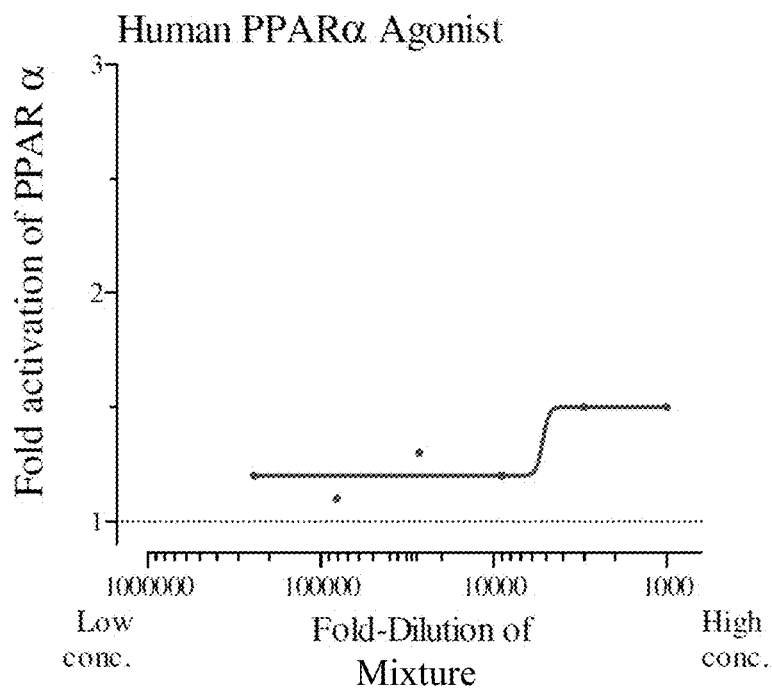
FIG. 7 illustrates fold-activation of PPARα for a mixture of alpha lipoic acid, resveratrol, curcumin, EGCG, Olivol®, rutin, quercetin, and hesperetin.
Figure 8:
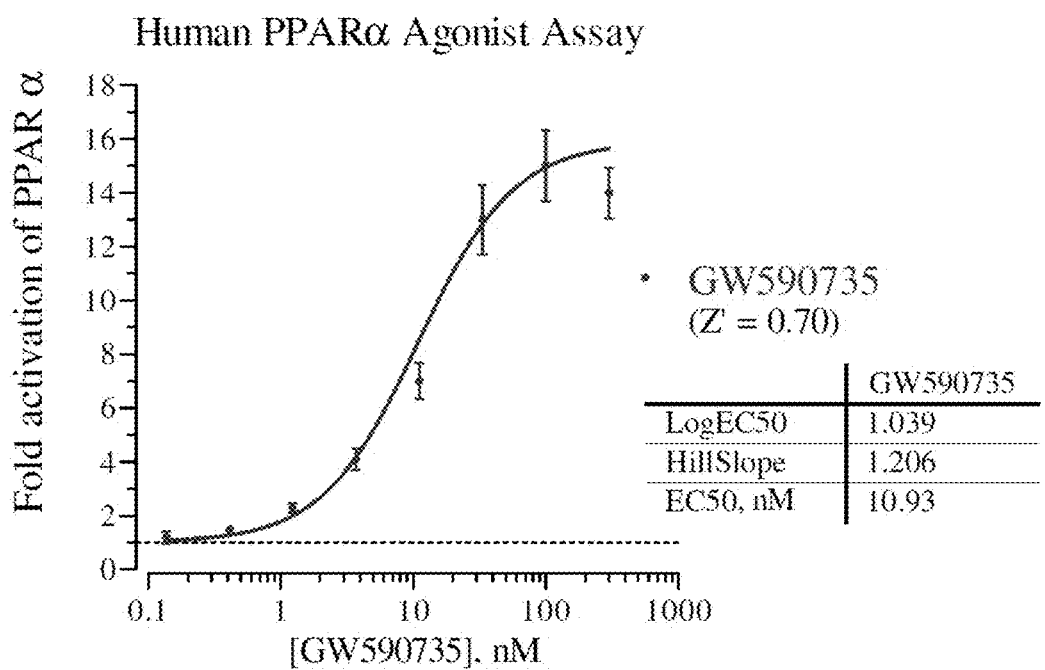
FIG. 8 illustrates fold-activation for a known PPARα agonist, GW590735.

The results for the receptor assays for human PPARα, PPARδ, PPARγ, and Nrf2 in agonist mode, human NF-κB in antagonist mode, and known agonists were analyzed and are presented graphically as FIGS. 5-23. FIG. 5 shows the fold-activation of PPARα for alpha lipoic acid, resveratrol, curcumin, and EGCG. FIG. 6 shows the fold-activation of PPARα for Olivol®, rutin, quercetin, and Hesperetin. FIG. 7 shows the fold-activation of PPARα for the mixture. FIG. 8 shows the fold-activation for a known PPARα agonist, GW590735.

Figure 9:
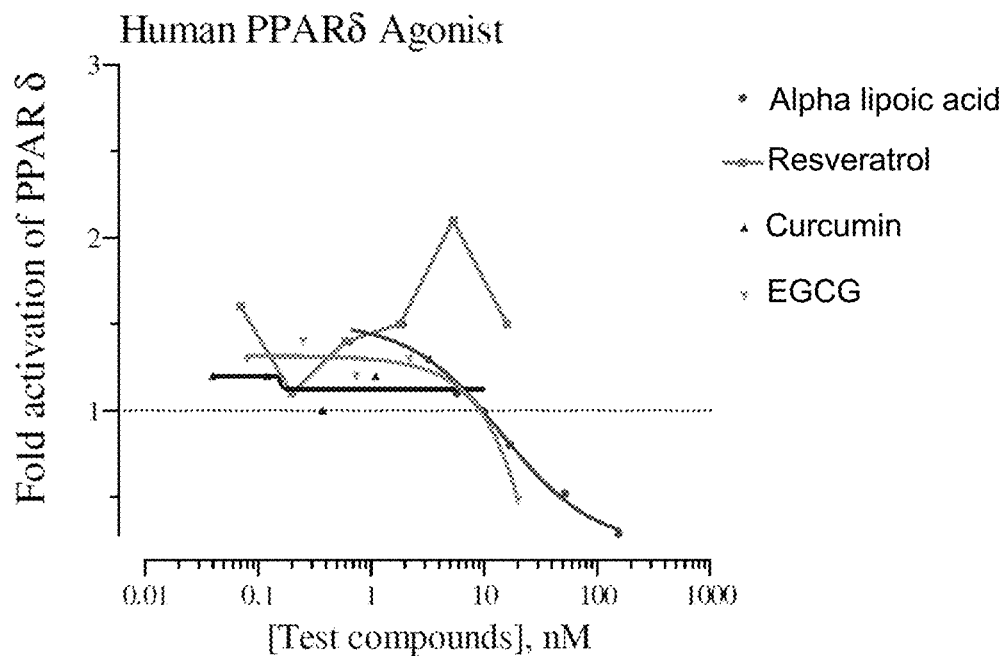
FIG. 9 illustrates fold-activation of PPARδ for alpha lipoic acid, resveratrol, curcumin, and EGCG.
Figure 10:
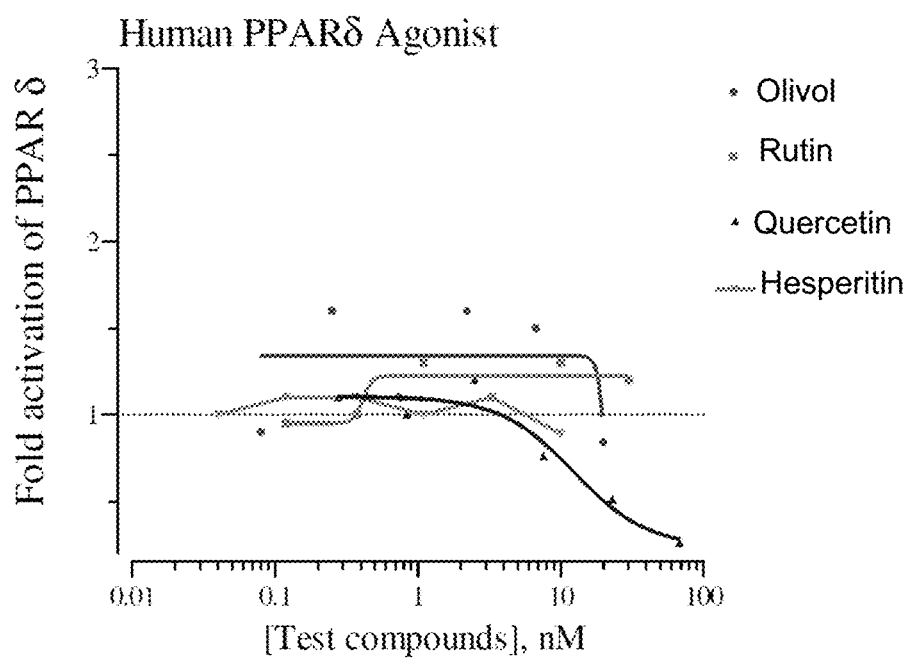
FIG. 10 illustrates fold-activation of PPARδ for Olivol®, rutin, quercetin, and hesperetin.
Figure 11:
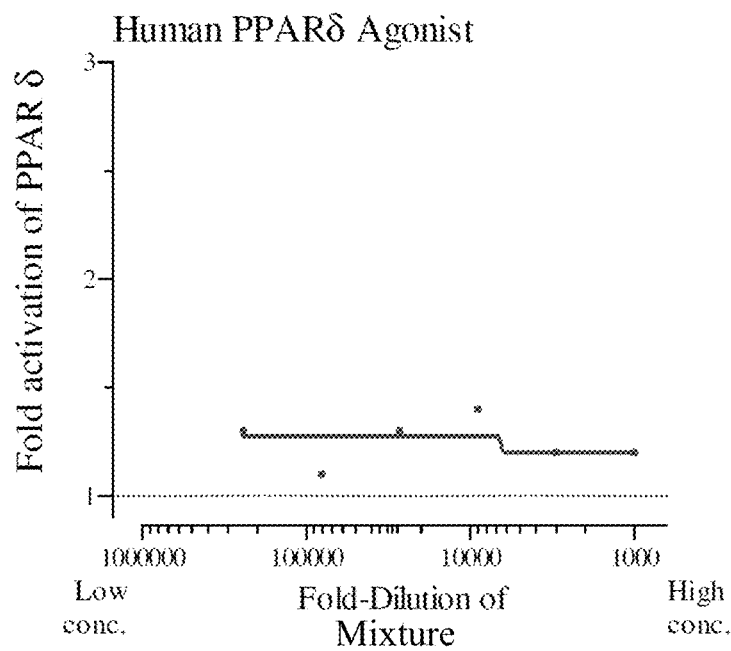
FIG. 11 illustrates fold-activation of PPARδ for a mixture of alpha lipoic acid, resveratrol, curcumin, EGCG, Olivol®, rutin, quercetin, and hesperetin.
Figure 12:
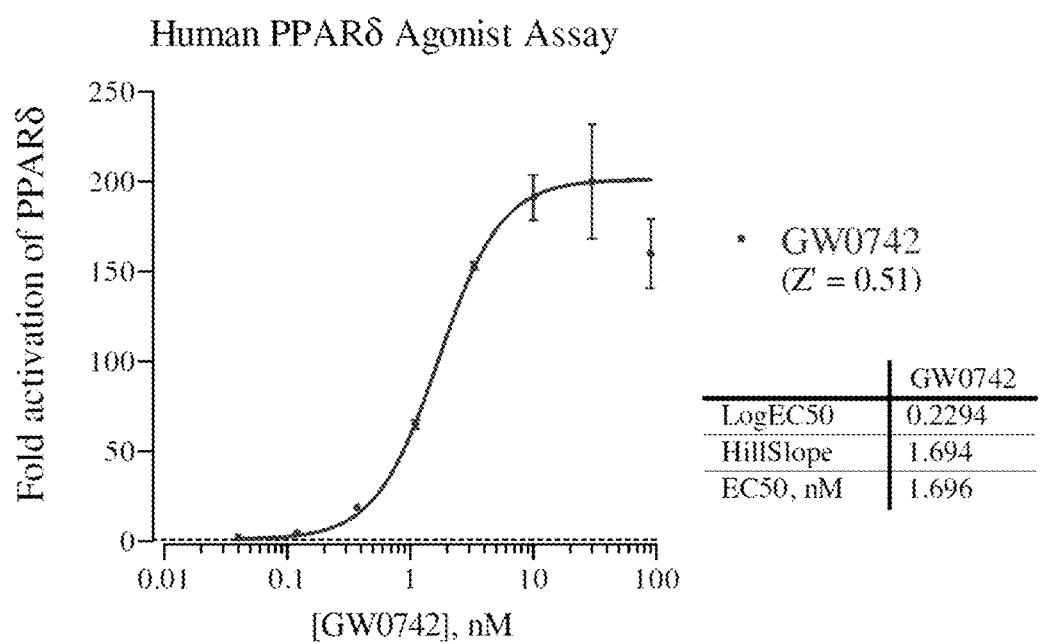
FIG. 12 illustrates fold-activation for a known PPARδ agonist, GW0742.

FIG. 9 shows the fold-activation of PPARδ for alpha lipoic acid, resveratrol, curcumin, and EGCG. FIG. 10 shows the fold-activation of PPARδ for Olivol®, rutin, quercetin, and Hesperetin. FIG. 11 shows the fold-activation of PPARδ for the mixture. FIG. 12 shows the fold-activation for a known PPARδ agonist, GW0742.

Figure 13:
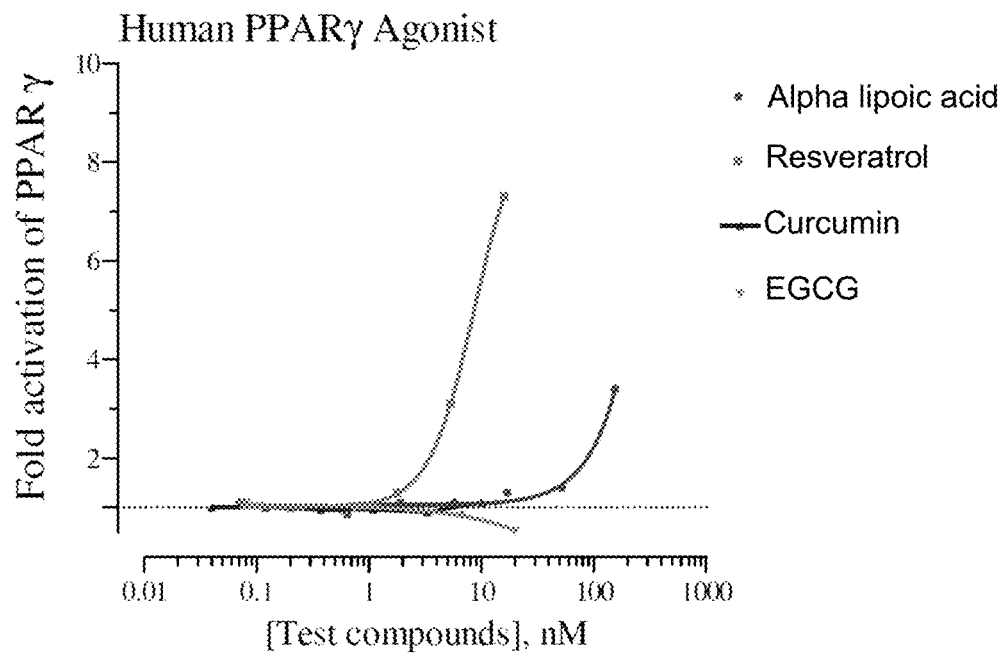
FIG. 13 illustrates fold-activation of PPARγ for alpha lipoic acid, resveratrol, curcumin, and EGCG.
Figure 14:
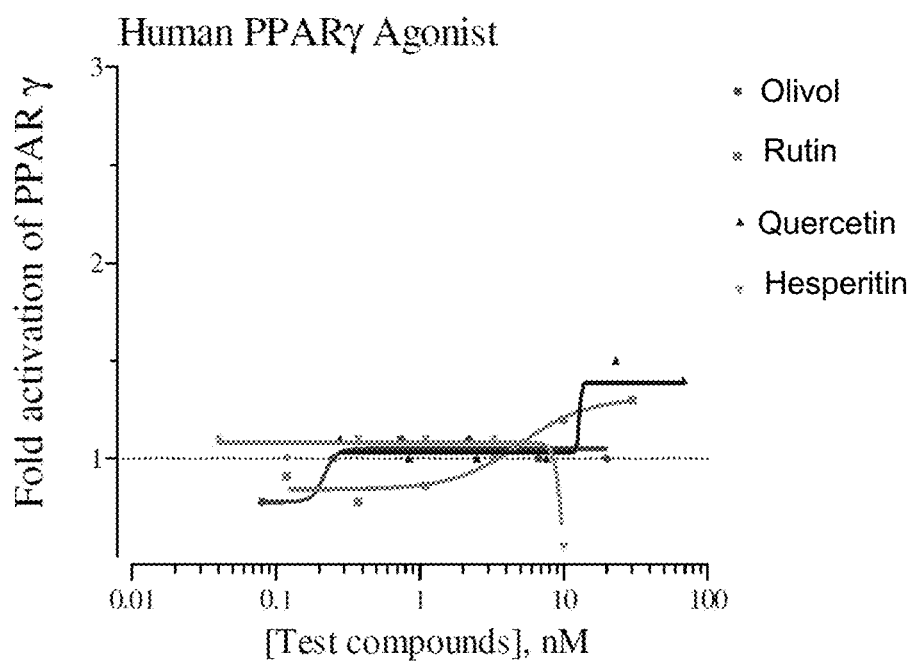
FIG. 14 illustrates fold-activation of PPARγ for Olivol®, rutin, quercetin, and hesperetin.
Figure 15:
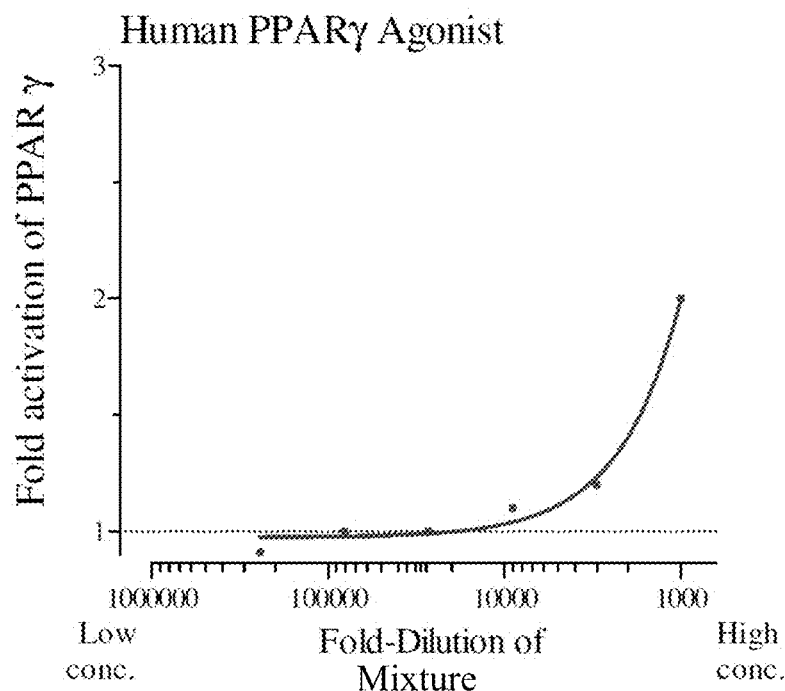
FIG. 15 illustrates fold-activation of PPARγ for a mixture of alpha lipoic acid, resveratrol, curcumin, EGCG, Olivol®, rutin, quercetin, and hesperetin.
Figure 16:
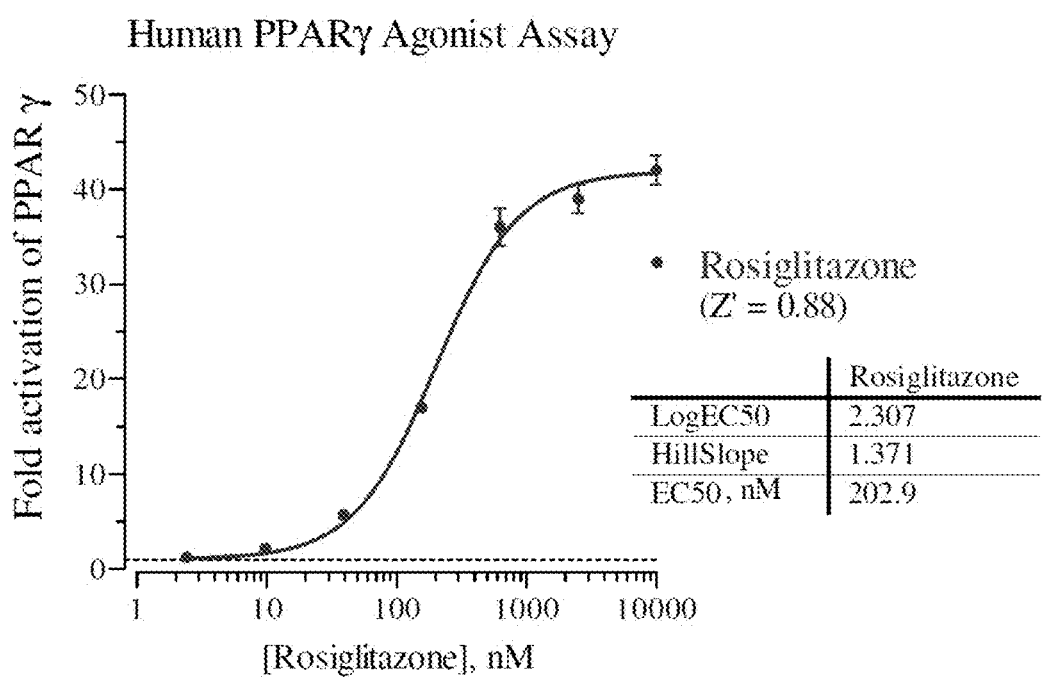
FIG. 16 illustrates fold-activation for a known PPARγ agonist, rosiglitazone.

FIG. 13 shows the fold-activation of PPARγ for alpha lipoic acid, resveratrol, curcumin, and EGCG. FIG. 14 shows the fold-activation of PPARγ for Olivol®, rutin, quercetin, and Hesperetin. FIG. 15 shows the fold-activation of PPARγ for the mixture. The induction concentration of alpha lipoic acid and resveratrol was 114.8 µg/mL and 2.54 µg/mL respectively when they are used alone, but was 1.22 µg/mL and 0.49 µg/mL respectively in the mixture, indicating the synergistic effect of the mixture. FIG. 16 shows the fold-activation for a known PPARγ agonist, rosiglitazone, as the positive control. As shown in the above-described figures, a strong activity was observed, particularly for PPARγ compared with PPARγ and PPARγ, either by the ingredients alone or the mixture. PPARγ is known to be a potent regulator of lipid and glucose metabolism, and synthetic PPARγ activators such as TZDs were once used as anti-diabetic drugs. Therefore, such findings have clinical relevance in improving metabolic health.

Figure 17:
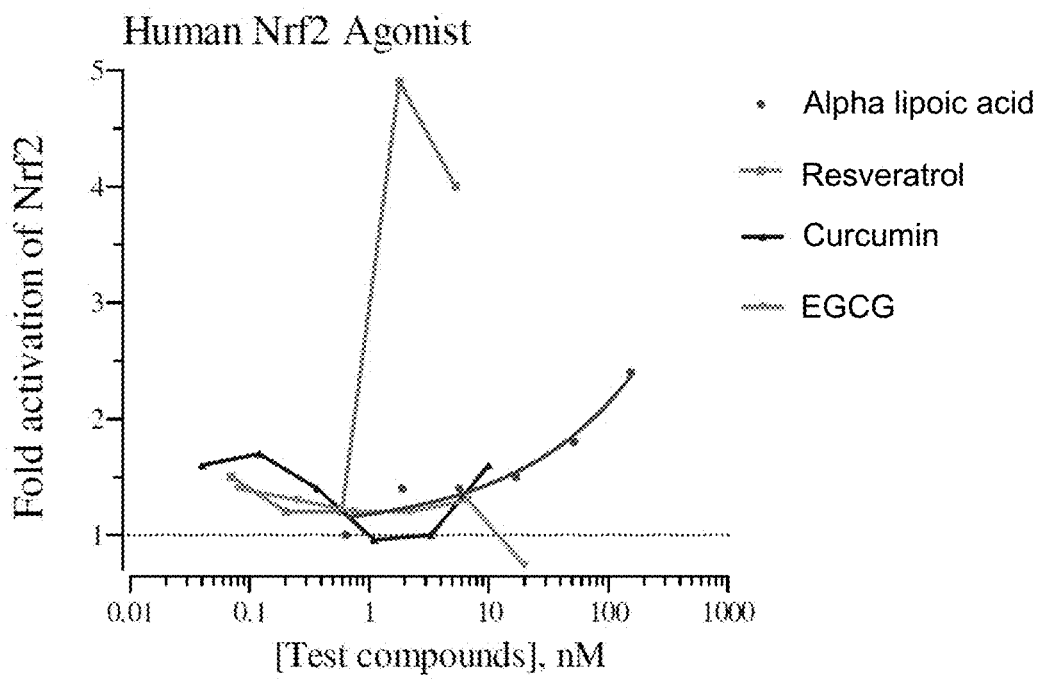
FIG. 17 illustrates fold-activation of Nrf2 for alpha lipoic acid, resveratrol, curcumin, and EGCG.
Figure 18:
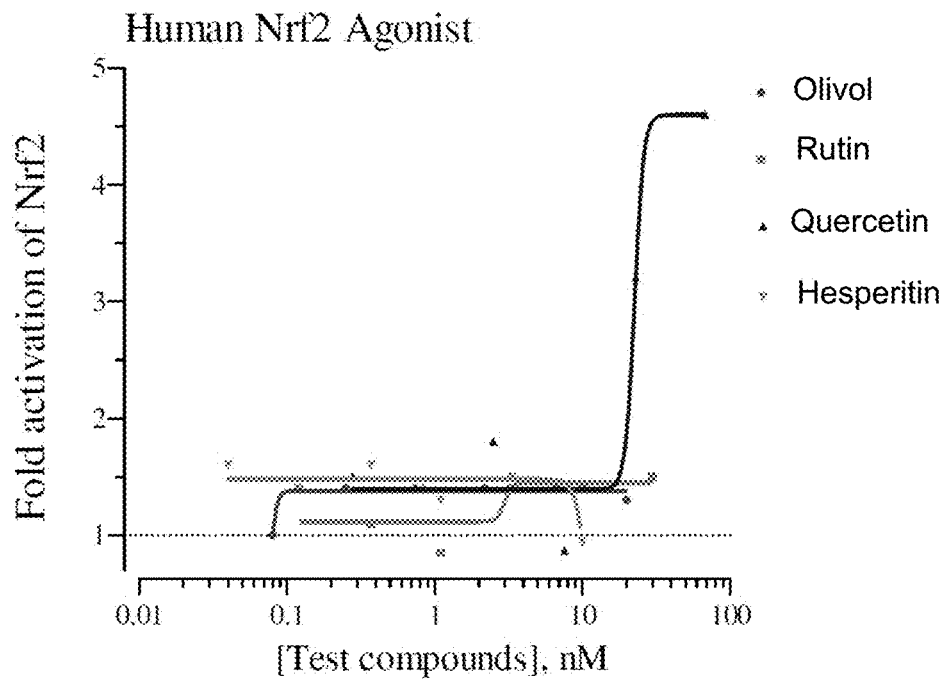
FIG. 18 illustrates fold-activation of Nrf2 for Olivol®, rutin, quercetin, and hesperetin.
Figure 19:
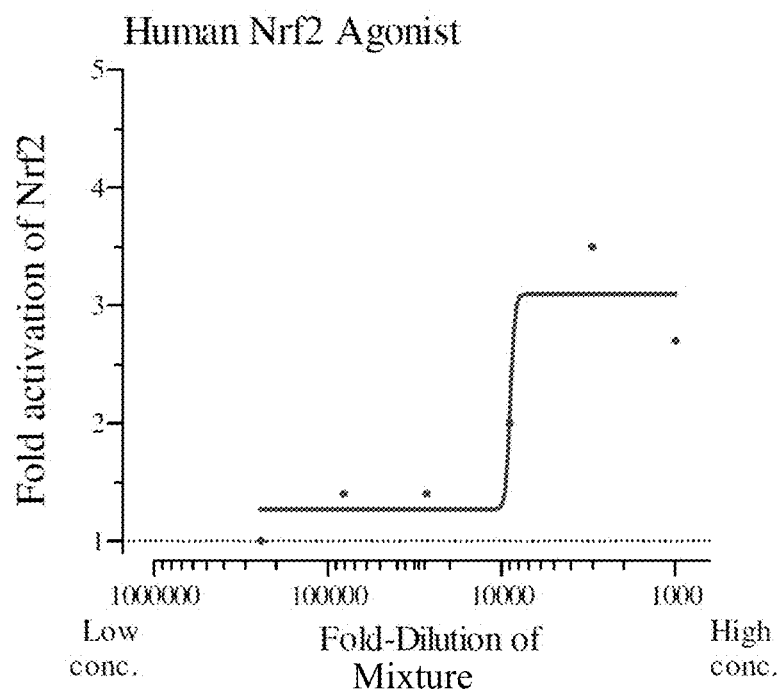
FIG. 19 illustrates fold-activation of Nrf2 for a mixture of alpha lipoic acid, resveratrol, curcumin, EGCG, Olivol®, rutin, quercetin, and hesperetin.
Figure 20:
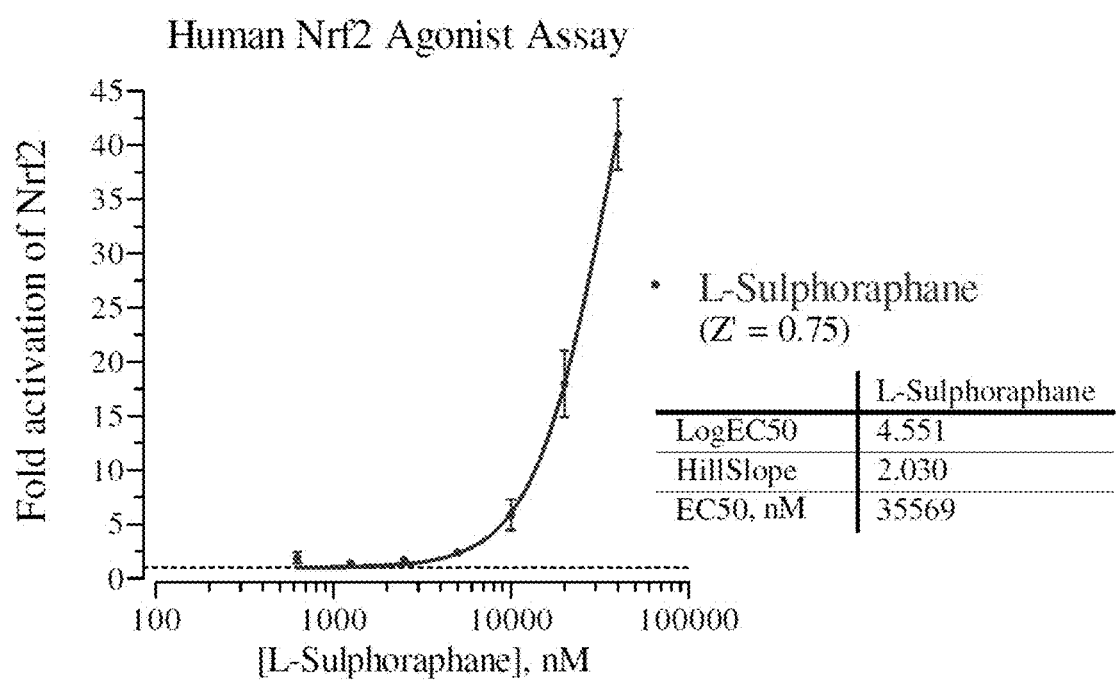
FIG. 20 illustrates fold-activation for a known Nrf2 agonist, L-sulphoraphane.

FIG. 17 shows the fold-activation of Nrf2 for alpha lipoic acid, resveratrol, curcumin, and EGCG. FIG. 18 shows the fold-activation of Nrf2 for Olivol®, rutin, quercetin, and Hesperetin. FIG. 19 shows the fold-activation of Nrf2 for the mixture. FIG. 20 shows the fold-activation for a known Nrf2 agonist, L-sulphoraphane.

Figure 21:
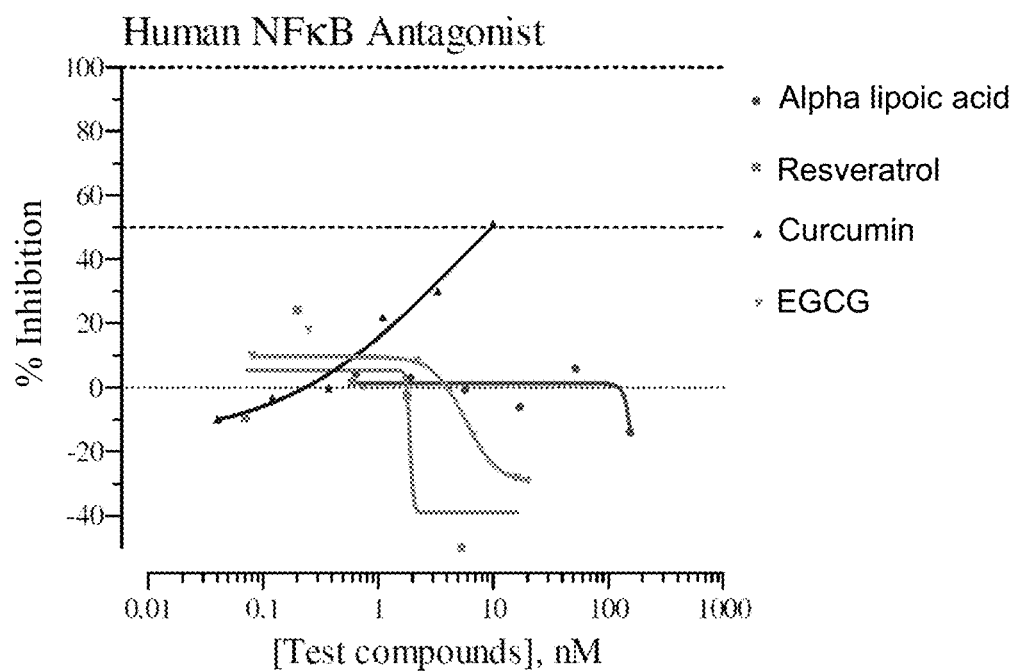
FIG. 21 illustrates percent inhibition of human NF-κB in antagonist mode form for alpha lipoic acid, resveratrol, curcumin, and EGCG.
Figure 22:
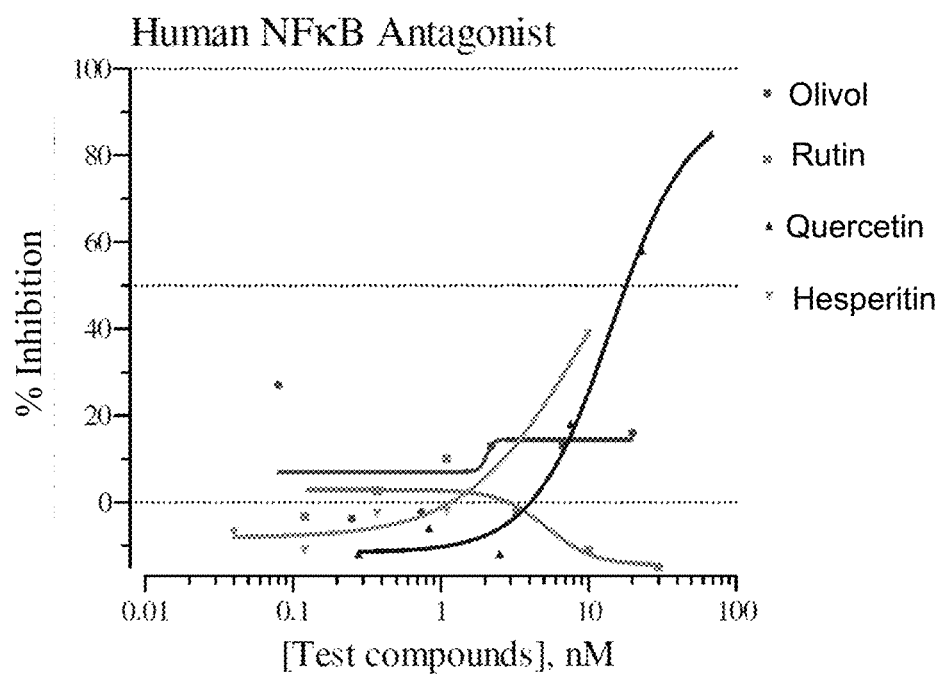
FIG. 22 illustrates percent inhibition of human NF-κB in antagonist mode form for Olivol®, rutin, quercetin, and hesperetin.
Figure 23:
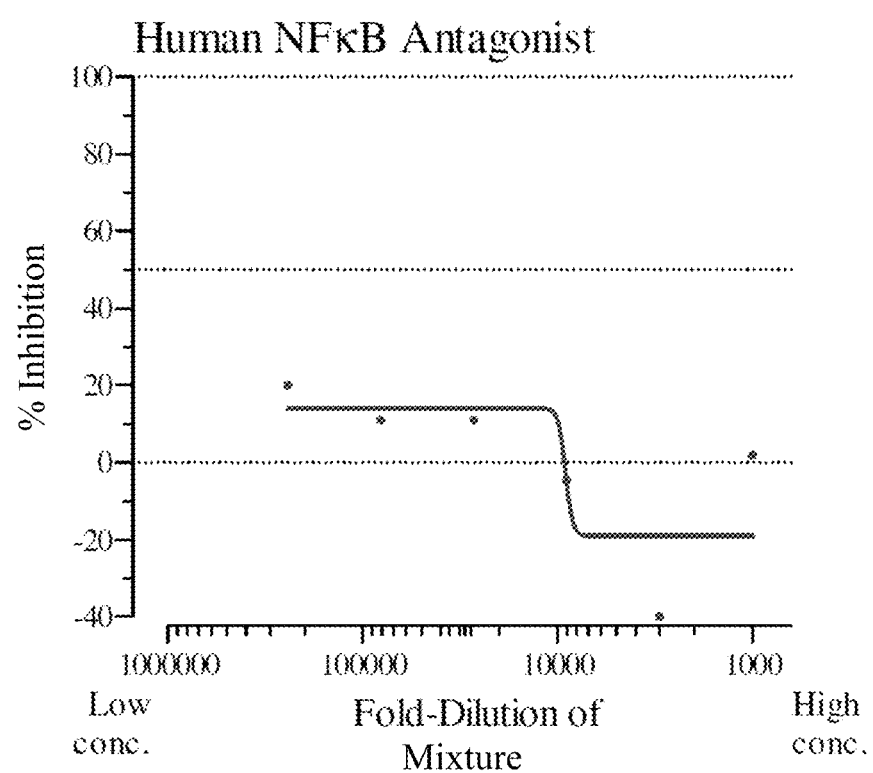
FIG. 23 illustrates percent inhibition of human NF-κB in antagonist mode form for a mixture of alpha lipoic acid, resveratrol, curcumin, EGCG, Olivol®, rutin, quercetin, and hesperetin.

FIG. 21 shows the percent inhibition of human NF-κB in antagonist mode form for alpha lipoic acid, resveratrol, curcumin, and EGCG. FIG. 22 shows the percent inhibition of human NF-κB in antagonist mode form for Olivol®, rutin, quercetin, and Hesperetin. FIG. 23 shows the percent inhibition of human NF-κB in antagonist mode form for the mixture.

An analysis of the data indicated that alpha lipoic acid exhibited very low-level agonist activity against human PPARα, PPARγ, and Nrf2 at the concentrations tested. The data also indicated that resveratrol exhibited very low-level agonist activity against human PPARδ and human Nrf2 and mid-level activity against human PPARγ at the concentrations tested. The data also indicated that curcumin exhibited very low-level antagonist activity against human NF-κB at the concentrations tested. The data also indicated that quercetin exhibited low-level agonist activity against human Nrf2 and very low-level antagonist activity against human NF-κB with some evidence of compounded-induced cytotoxicity at the concentrations tested. Importantly, the data also indicated that the mixture exhibited agonist activity against human PPARγ and human Nrf2 at a concentration much lower than when they were used alone.

Example 2

Phenotypic screening with a specialized strain of *C. elegans* worm was carried out using two test formulations of the disclosed nutritional supplement compositions to assess their effect on epigenetic anti-ageing activity. A first test formulation comprised the composition as described below in Table 9B and other inert ingredients and was labeled as "N356." A second test formulation comprised a combination of alpha lipoic acid, resveratrol, curcumin, EGCG, Olivol®, rutin, quercetin, and Hesperetin as described below in Table 9C and was labeled as "N357." Each test formulation was tested over a range of concentrations. Dilutions of the test formulations were applied to individual populations of *C. elegans* and the lifespan of each population was monitored. Any changes in the lifespan of an individual population compared to a control population were recorded and correlated to the respective test formulation (N356 or N357) and the respective dilution (0.1 mg/ml, 1 mg/ml, and 10 mg/ml).

TABLE 9B

| Active Ingredient: | mg: |
| --- | --- |
| Mixed Carotenoids (alpha, beta, gamma carotene and lycopene) | 0.10 |
| Beta carotene (2150 IU tab) | 1.29 |
| Retinyl Acetate (750 IU) | 0.26 |
| Vitamin C (Poly C, Ca, K, Mg and Zn Ascorbates) | 100.00 |
| Vitamin D3 (Cholecalciferol) [500 IU/tab] | 0.0125 |
| Vitamin E (d-alpha-tocopheryl succ. 50 IU) | 41.30 |
| Mixed Tocopherols | 20.00 |
| Vitamin K1 | 0.12 |
| Vitamin K2 (menaquinone, MK-7) | 0.02 |
| Vitamin B1 (thiamin HCL) | 7.50 |
| Vitamin B2 (riboflavin) | 7.50 |
| Niacin | 2.50 |
| Niacinamide | 7.50 |
| Vitamin B6 (pyridoxine HCL) | 8.00 |
| Folic Acid | 0.15 |
| Vitamin B12 (cyanocobalamin) | 0.05 |
| Biotin | 0.08 |
| Pantothenic Acid | 22.50 |
| Alpha Lipoic Acid | 25.00 |
| Resveratrol | 10.00 |
| Curcumin Phytosome Complex (containing 3.25 mg curcuminoids) | 18.06 |
| Green Tea Extract (standardized to EGCG) | 17.50 |
| Olivol ® (Olive Fruit Extract) | 7.50 |
| Rutin | 10.00 |
| Quercetin Dihydrate | 15.00 |
| Hesperetin | 10.00 |
| Inositol | 32.00 |
| Choline bitartrate | 62.50 |
| Coenzyme Q-10 | 3.00 |
| Lutein | 0.15 |
| Lycopene | 0.25 |

TABLE 9C

| Active Ingredient: | mg: |
| --- | --- |
| Alpha Lipoic Acid | 25.00 |
| Resveratrol | 10.00 |
| Curcumin Phytosome Complex (containing 3.25 mg curcuminoids) | 18.06 |
| Green Tea Extract (standardized to EGCG) | 17.50 |
| Olivol (Olive Fruit Extract) | 7.50 |
| Rutin | 10.00 |
| Quercetin Dihydrate | 15.00 |
| Hesperidin | 10.00 |

The N256 and N357 formulations were each prepared as individual 100 mg/ml stock solutions in dimethyl sulfoxide (DMSO). Serial dilutions of each stock solution were then prepared at 0.1 mg/ml, 1 mg/ml, and 10 mg/ml in DMSO. Control solutions of DMSO only were also prepared. Synchronous aged adult populations of *C. elegans* strain CB5586 worms were prepared. The CB5586 strain comprises a pharyngeal GFP (green fluorescent protein) tag and a mutation in the bus-5 gene. The pharyngeal GFP tag allows for fluorescent images of the worm populations to be taken. The mutation in the bus-5 gene causes the loss of normal cuticle antigens that permits the cuticle of the worms to become permeable to the test formulations and allow direct uptake of the test formulations to avoid interaction of the test formulations with protective mechanisms of the gut channel. Each serial dilution of each test formulation was added to a separate population of the prepared worms. The control solutions were also added to separate populations of the prepared worms. The populations of the prepared worms were then maintained on standard nematode growth media (NGM) agar plates at 20° C. with sufficient food (*Escherichia coli* strain OP-50).

Each worm population was then monitored by fluorescent imaging to determine the number of living and dead worms as a function of time. The fluorescent imaging was analyzed by software that recognized and counted worms based on their fluorescent intensity compared to background fluorescence. Living worms were automatically distinguished by the software from dead worms based on the degree of movement they exhibited between consecutive fluorescent images. The ability to distinguish between living and dead worms allowed the number of living worms and a cumulative number of dead worms to be monitored against time. Worm populations from a selection of fluorescent images were manually checked to verify that the software had accurately counted the number of living and dead worms.

Figure 24:
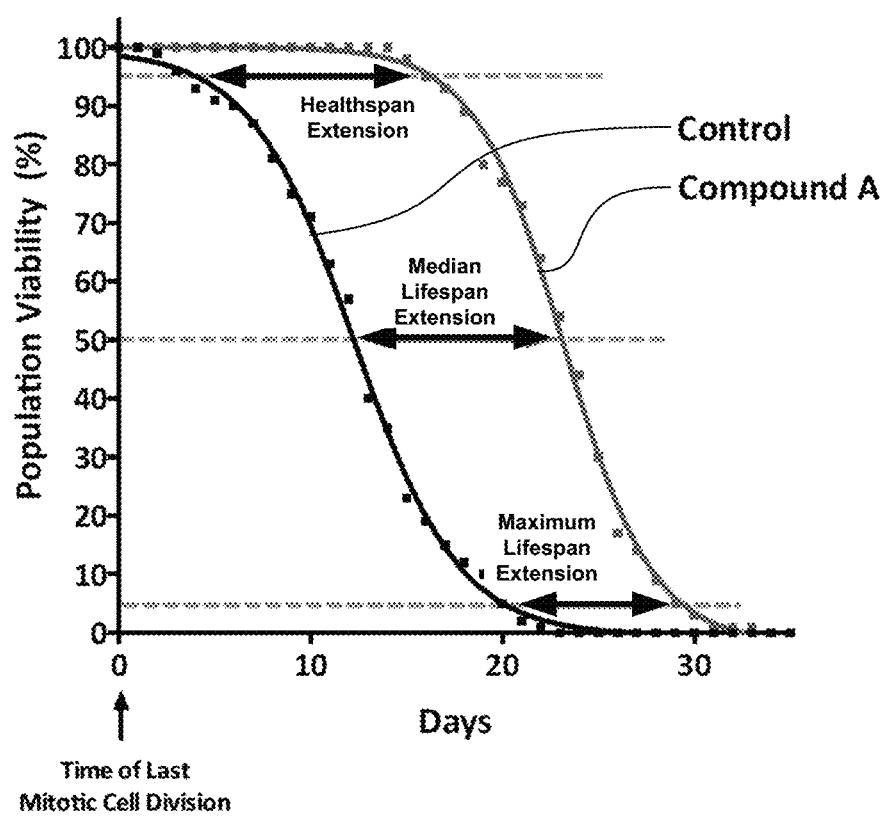
FIG. 24 illustrates an ideal Kaplan-Meier survival curve for a control population and a population exposed to an ideal test compound.

The counts of the living and dead worms as a function of time were then analyzed for each of the worm populations and used to prepare Kaplan-Meier survival curves and associated statistics for each of the worm populations. FIG. 24 shows an ideal Kaplan-Meier survival curve for a control population and a population exposed to an ideal test compound, "Compound A." The health span extension is shown as the length of time after the last mitotic division that 95% of the test population remains viable when compared to the control population. The median lifespan is shown as the length of time after the last mitotic division that 50% of the test population remains viable when compared to the control population. The maximum lifespan extension is shown as the length of time after the last mitotic division that 5% of the test population remains viable when compared to the control population.

Figure 25:
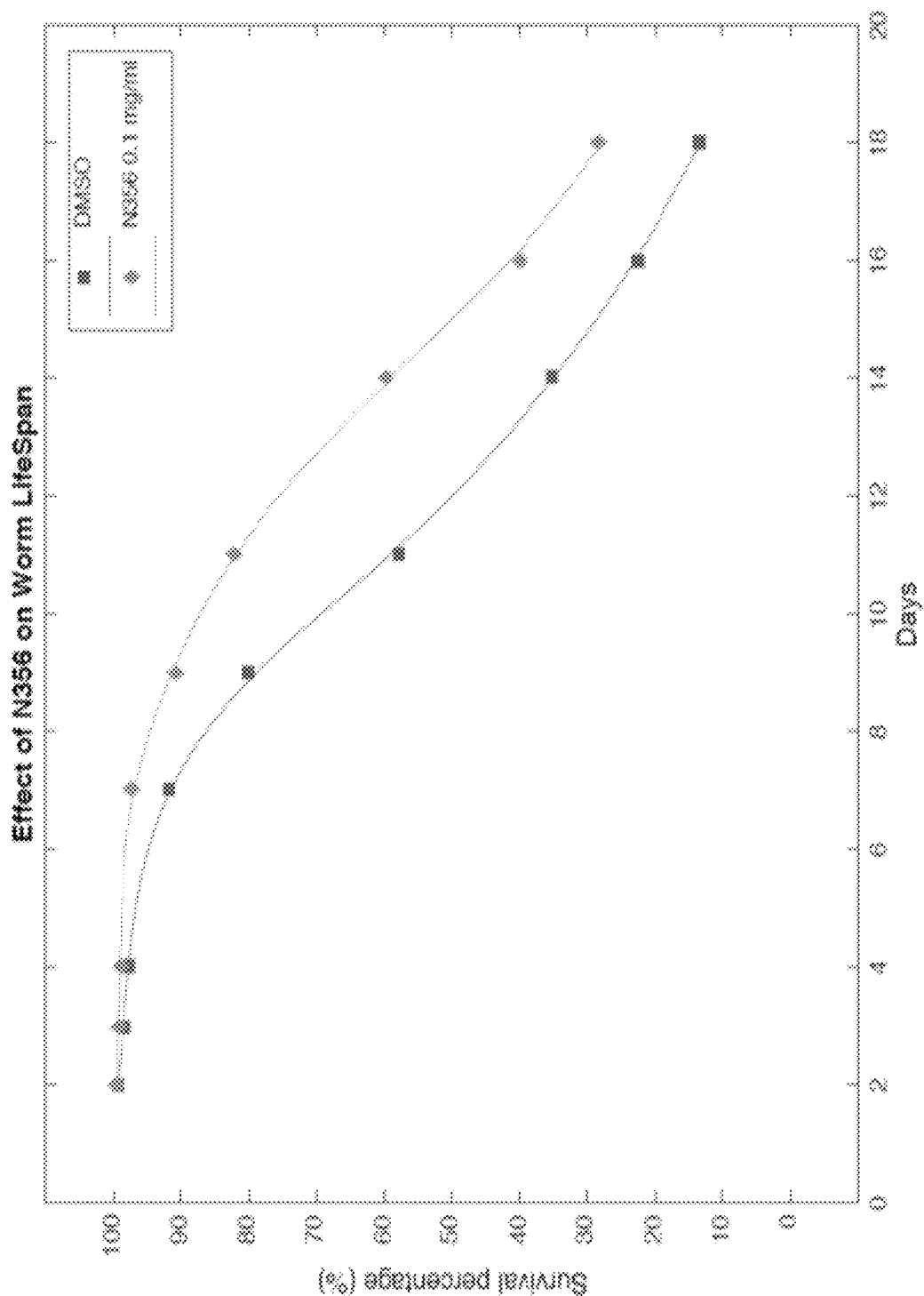
FIG. 25 illustrates a Kaplan-Meier survival curve for the worm population tested with N356 at 0.1 mg/ml concentration.
Figure 26:
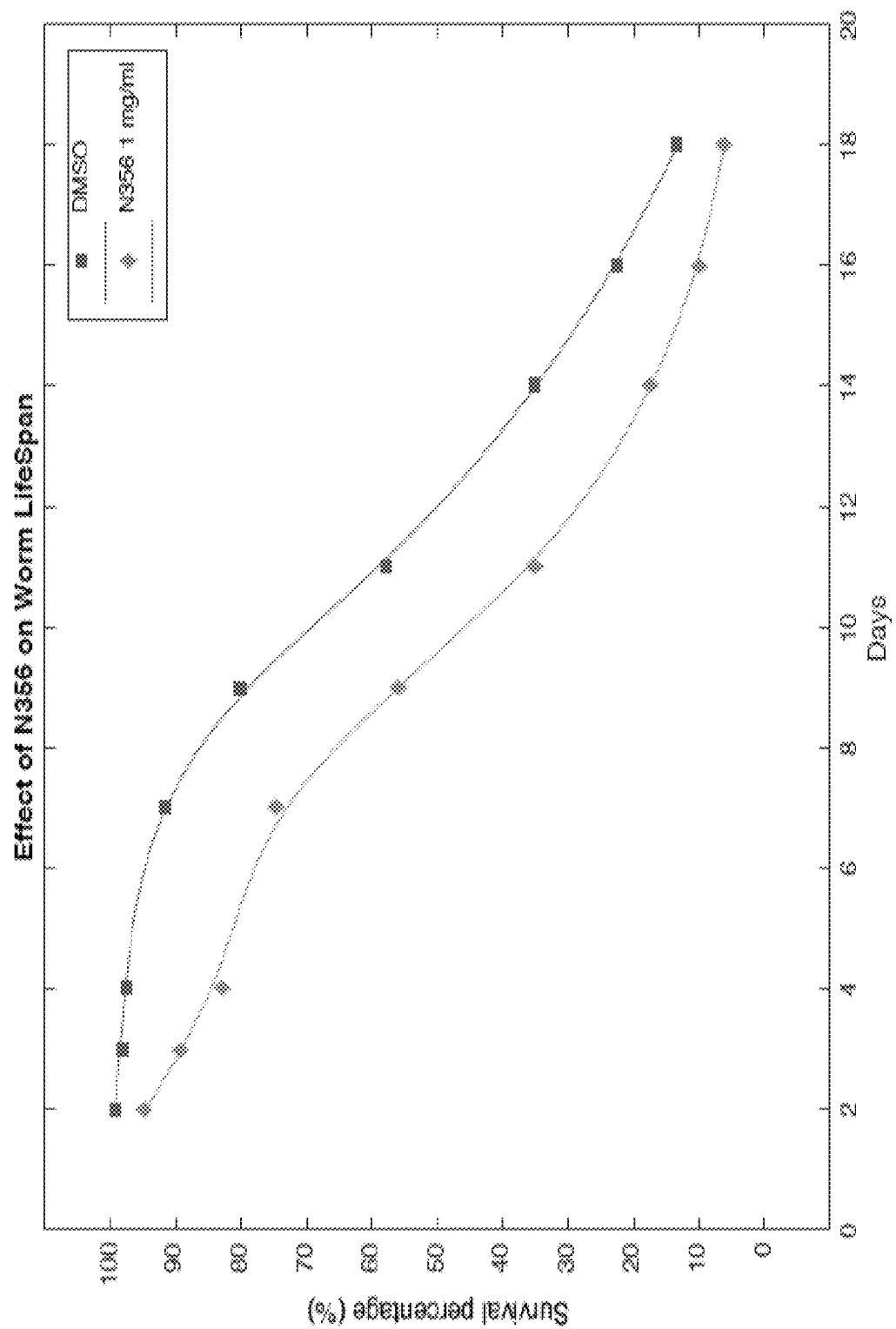
FIG. 26 illustrates a Kaplan-Meier survival curve for the worm population tested with N356 at 1.0 mg/ml concentration.
Figure 27:
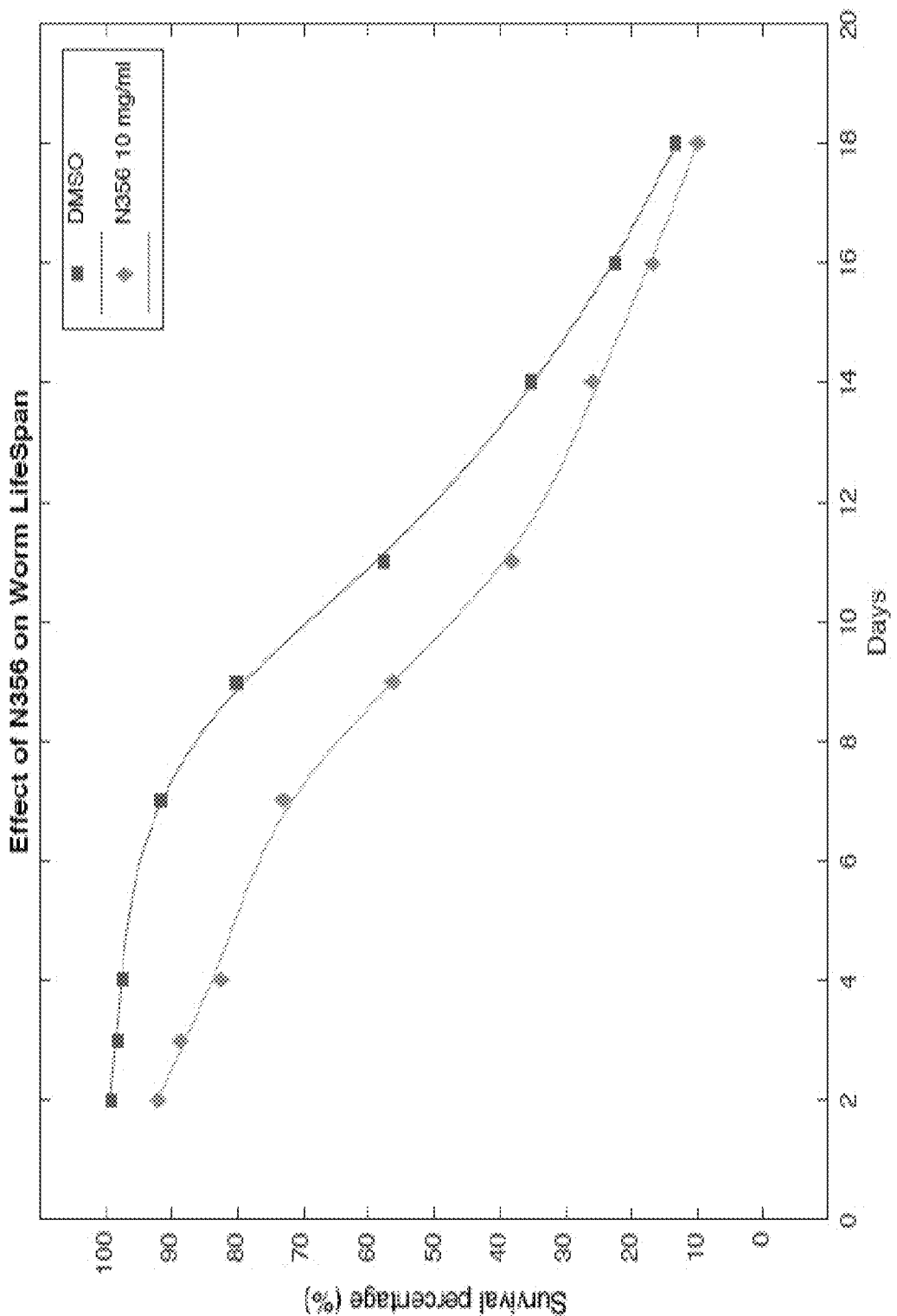
FIG. 27 illustrates a Kaplan-Meier survival curve for the worm population tested with N356 at 10 mg/ml concentration.
Figure 28:
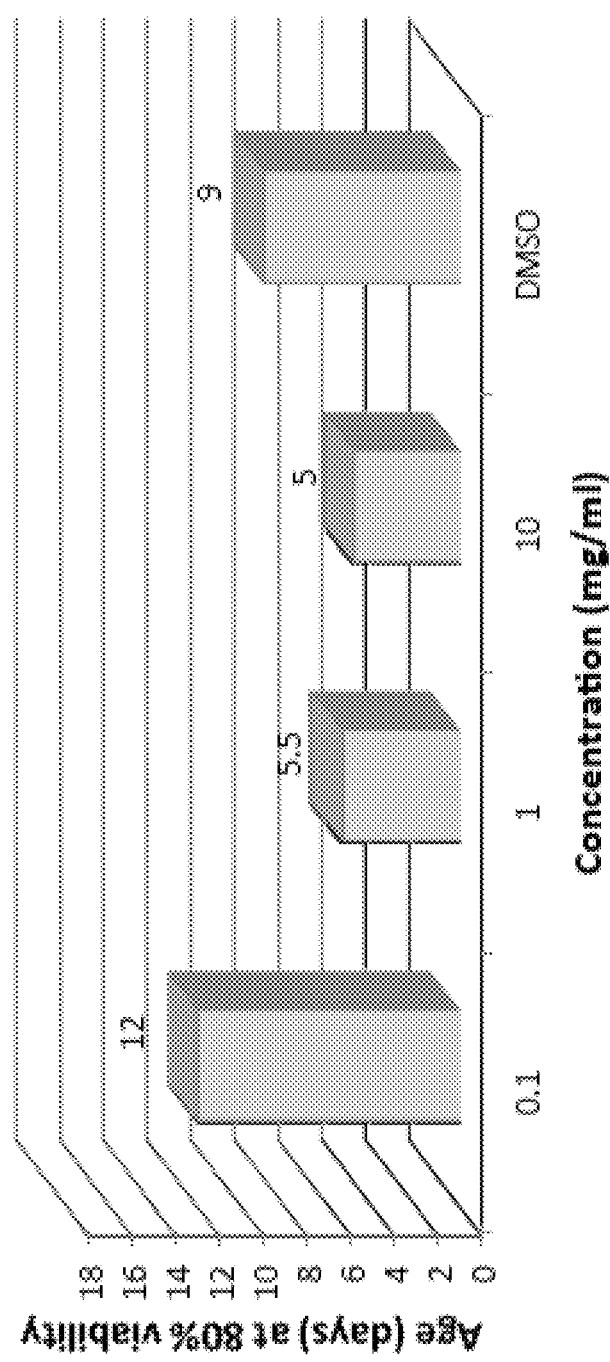
FIG. 28 illustrates a dose-dependent extension of lifespan for N356 at 0.1 mg/ml, 1.0 mg/ml, and 10 mg/ml compared to DMSO for health span measured as a function of age at 20% mortality.

FIG. 25 show a Kaplan-Meier survival curve for the worm population tested with N356 at the 0.1 mg/ml concentration. FIG. 26 show a Kaplan-Meier survival curve for the worm population tested with N356 at the 1.0 mg/ml concentration. FIG. 27 show a Kaplan-Meier survival curve for the worm population tested with N356 at the 10 mg/ml concentration. FIG. 28 shows a dose-dependent extension of lifespan for N356 at 0.1 mg/ml, 1.0 mg/ml, and 10 mg/ml compared to DMSO for health span measured as a function of age at 20% mortality.

Figure 29:
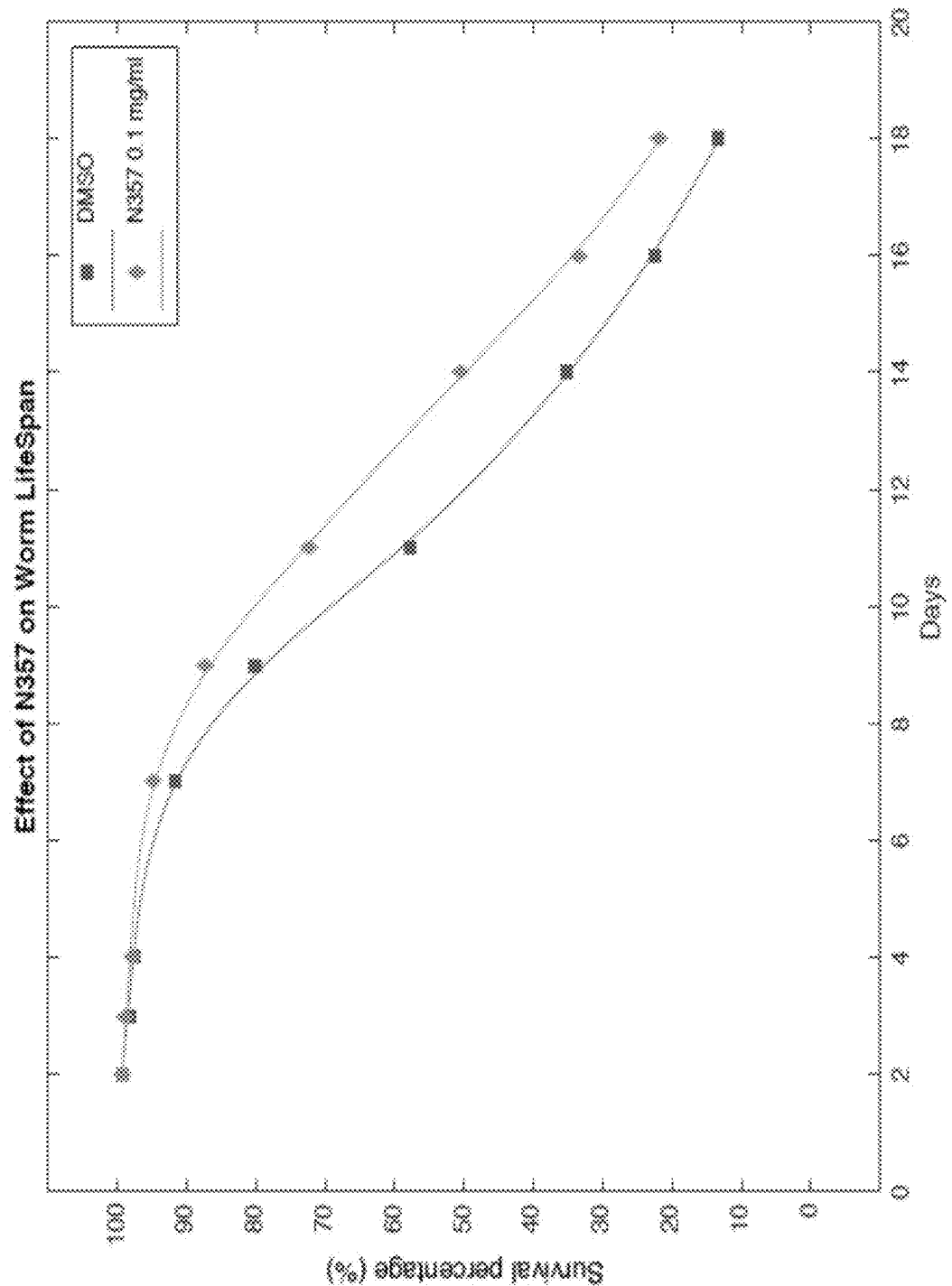
FIG. 29 illustrates a Kaplan-Meier survival curve for the worm population tested with N357 at the 0.1 mg/ml concentration.
Figure 30:
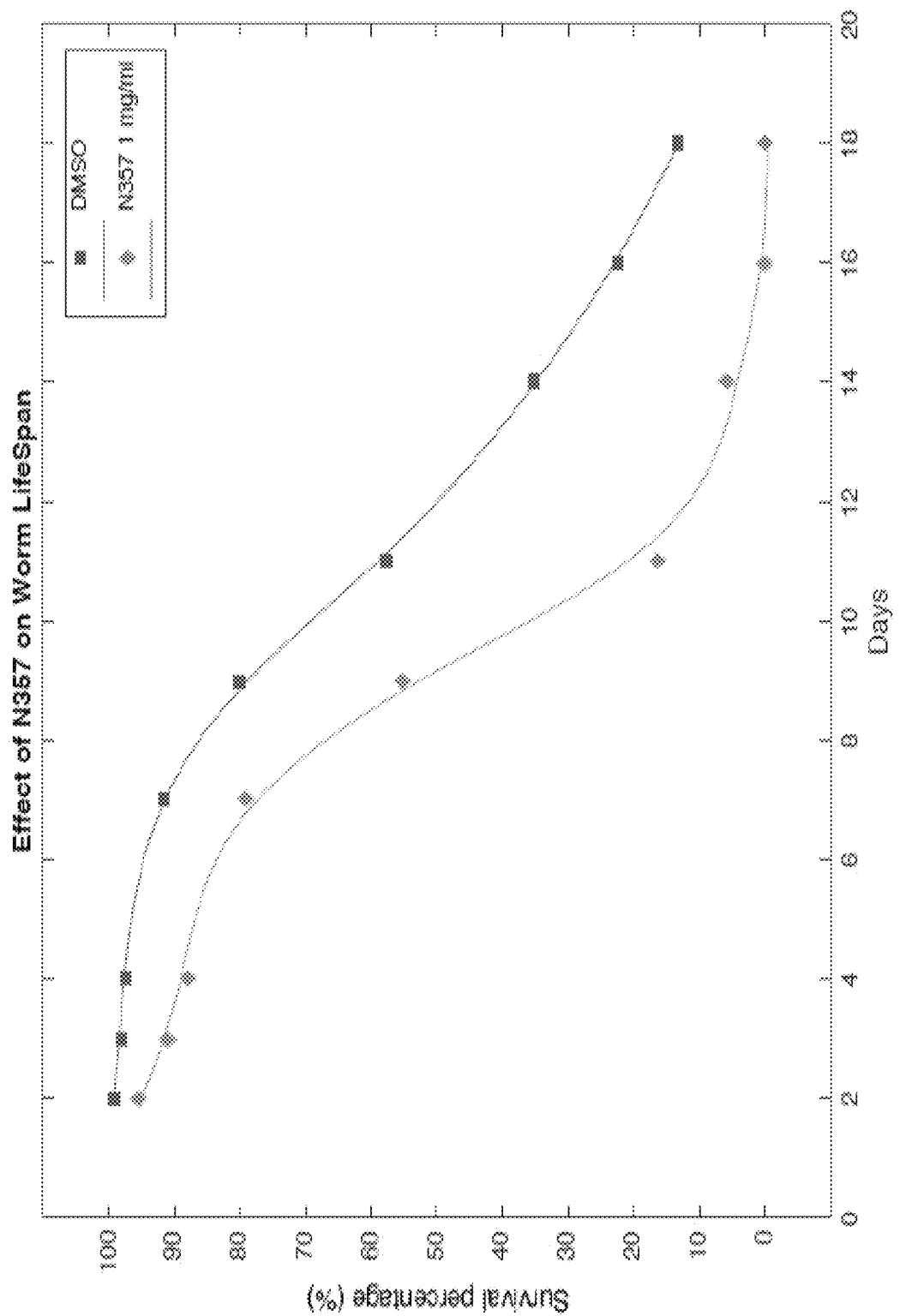
FIG. 30 illustrates a Kaplan-Meier survival curve for the worm population tested with N357 at the 1.0 mg/ml concentration.
Figure 31:
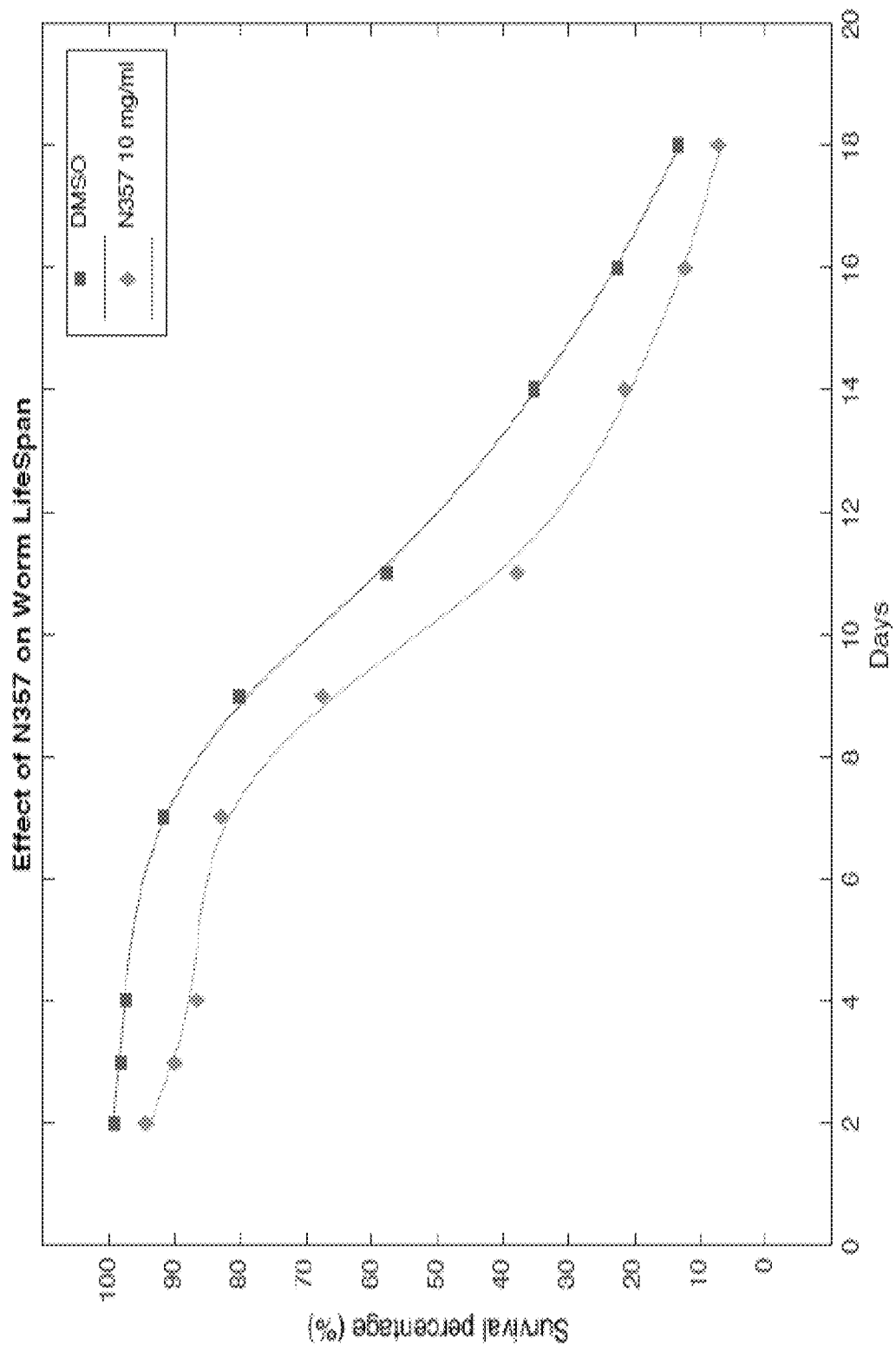
FIG. 31 illustrates a Kaplan-Meier survival curve for the worm population tested with N357 at the 10 mg/ml concentration.
Figure 32:
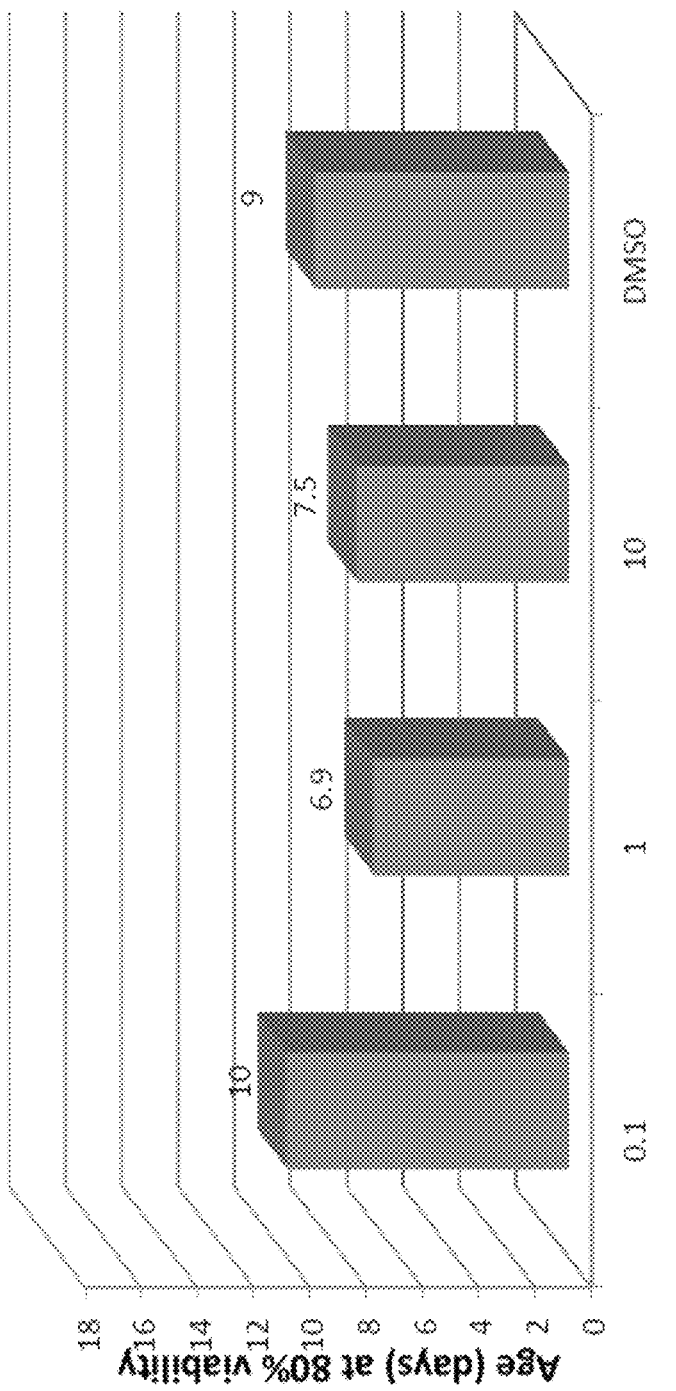
FIG. 32 illustrates a dose-dependent extension of lifespan for N357 at 0.1 mg/ml, 1.0 mg/ml, and 10 mg/ml compared to DMSO for health span measured as a function of age at 20% mortality.

FIG. 29 show a Kaplan-Meier survival curve for the worm population tested with N357 at the 0.1 mg/ml concentration. FIG. 30 show a Kaplan-Meier survival curve for the worm population tested with N357 at the 1.0 mg/ml concentration. FIG. 31 show a Kaplan-Meier survival curve for the worm population tested with N357 at the 10 mg/ml concentration. FIG. 32 shows a dose-dependent extension of lifespan for N357 at 0.1 mg/ml, 1.0 mg/ml, and 10 mg/ml compared to DMSO for health span measured as a function of age at 20% mortality.

The counts of the living and dead worms as a function of time and the Kaplan-Meier survival curves and the associated statistics were then analyzed for each of the worm populations. The analysis included determining mean and median lifespan. The analysis included a non-parametric test, the Log-Rank test, which compares two survival functions for the overall lifespan assay and provides a reliable p-value summarizing the whole experiment. The analysis also included Fisher's Exact Test that calculated the significance of survival function comparisons at multiple specific time points throughout the experiment, rather than for the overall lifespan. The results of the analysis are shown below in Tables 10-17. Table 10 shows the restricted mean lifespan for the N356 treated worm population compared to the DMSO control. Table 11 shows the restricted mean lifespan for the N357 treated worm population compared to the DMSO control. Table 12 shows the population age in days at given percent mortalities for the N356 treated worm population compared to the DMSO control. Table 13 shows the population age in days at given percent mortalities for the N357 treated worm population compared to the DMSO control. Table 14 shows the Log-Rank Test results for the N356 treated worm population compared to the DMSO control. Table 15 shows the Log-Rank Test results for the N356 treated worm population compared to the DMSO control. Table 16 shows the Fisher's Exact Test results for the N356 treated worm population compared to the DMSO control. Table 17 shows the Fisher's Exact Test results for the N357 treated worm population compared to the DMSO control.

TABLE 10

| Test Formulation | # of Days | Standard Error | 95% Confidence Interval |
|---|---|---|---|
| DMSO | 13.23 | 0.08 | 13.06~13.39 |
| N356 at 0.1 mg/ml | 15.18 | 0.14 | 14.90~15.45 |
| N356 at 1.0 mg/ml | 10.56 | 0.36 | 9.85~11.27 |
| N356 at 10 mg/ml | 10.87 | 0.24 | 10.40~11.34 |

TABLE 11

| Test Formulation | # of Days | Standard Error | 95% Confidence Interval |
|---|---|---|---|
| DMSO | 13.23 | 0.08 | 13.06~13.39 |
| N357 at 0.1 mg/ml | 14.40 | 0.15 | 14.11~14.70 |
| N357 at 1.0 mg/ml | 9.81 | 0.41 | 9.00~10.61 |
| N357 at 10 mg/ml | 11.26 | 0.26 | 10.77~11.76 |

TABLE 12

| Test Formulation | 25% | 50% | 75% | 90% | 100% |
|---|---|---|---|---|---|
| DMSO | 11 | 14 | 16 | — | — |
| N356 at 0.1 mg/ml | 14 | 16 | — | — | — |
| N356 at 1.0 mg/ml | 7 | 11 | 14 | 18 | — |
| N356 at 10 mg/ml | 7 | 11 | 16 | — | — |

TABLE 13

| Test Formulation | 25% | 50% | 75% | 90% | 100% |
|---|---|---|---|---|---|
| DMSO | 11 | 14 | 16 | — | — |
| N357 at 0.1 mg/ml | 11 | 16 | 18 | — | — |
| N357 at 1.0 mg/ml | 9 | 11 | 14 | 16 | 18 |
| N357 at 10 mg/ml | 9 | 11 | 14 | 18 | — |

TABLE 14

| Condition | $Chi^2$ | P-value | Bonferroni P-value |
|---|---|---|---|
| DMSO vs. N356 at 0.1 mg/ml | 105.81 | 0.0e+00 | 0.0e+00 |
| DMSO vs. N356 at 1.0 mg/ml | 47.47 | 0.0e+00 | 0.0e+00 |
| DMSO vs. N356 at 10 mg/ml | 51.94 | 0.0e+00 | 0.0e+00 |

TABLE 15

| Condition | $Chi^2$ | P-value | Bonferroni P-value |
|---|---|---|---|
| DMSO vs. N357 at 0.1 mg/ml | 45.16 | 0.0e+00 | 0.0e+00 |
| DMSO vs. N357 at 1.0 mg/ml | 67.03 | 0.0e+00 | 0.0e+00 |
| DMSO vs. N357 at 10 mg/ml | 45.17 | 0.0e+00 | 0.0e+00 |

TABLE 16

| Condition | P-value at 25% | P-value at 50% | P-value at 75% | P-value at 90% |
|---|---|---|---|---|
| DMSO vs. N356 at 0.1 mg/ml | 2.7e−12 | 2.5e−12 | 1.9e−12 | 1.5e−12 |
| DMSO vs. N356 at 1.0 mg/ml | 5.0e−08 | 5.0e−08 | 3.3e−06 | 0.0093 |
| DMSO vs. N356 at 10 mg/ml | 2.0e−12 | 3.5e−11 | 0.0001 | 0.0591 |

TABLE 17

| Condition | P-value at 25% | P-value at 50% | P-value at 75% | P-value at 90% |
|---|---|---|---|---|
| DMSO vs. N357 at 0.1 mg/ml | 6.6e−11 | 3.0e−11 | 2.2e−07 | 9.7e−07 |
| DMSO vs. N357 at 1.0 mg/ml | 1.3e−11 | 1.3e−11 | 5.2e−08 | 0.0001 |
| DMSO vs. N357 at 10 mg/ml | 9.8e−11 | 9.8e−11 | 1.2e−06 | 0.0012 |

The analysis of the phenotypic screen indicated that both N356 and N357 displayed anti-ageing activity. In particular, at the 0.1 mg/ml concentration, the worm population treated with N356 and the worm population treated with N357 both showed statistically significant increases in chronological lifespan. Treatment with N356 resulted in a statistically significant improvement in mean life span of about 9%, a maximum improvement in lifespan of about 14.3% at 50% mortality, and a maximum improvement in survival up to about 25% between days 11 and 14 (e.g., the mid-lifespan and the late-life span). Likewise, treatment with N357 resulted in a statistically significant improvement in mean lifespan of about 9%, a maximum improvement in lifespan of about 14.3% at 50% mortality, and a maximum improvement in survival up to about 16% between days 11 and 14 (mid-lifespan and late-lifespan). The maximum effect was seen in the combination formulation N356. Both treatments also demonstrated significant improvements to lifespan during the early stages of the population survival curve that lay between health span and median lifespan.

The analysis of the N356 populations indicated that of the 0.1 mg/ml, the 1.0 mg/ml, and the 10 mg/ml concentrations that the 0.1 mg/ml concentration appeared to be the optimum dose. The N356 0.1 mg/ml concentration treatment resulted in a statistically significant improvement in mean life span of 15%, a maximum improvement in lifespan of 27% at 25% mortality, and a maximum improvement in survival up to 25% between days 11 and 14. The Log-Rank test results and the Fisher's Exact test results showed significance overall for the length of the study and for each individual time point within the study for the N356 0.1 mg/ml concentration.

The analysis of the N357 populations indicated that of the 0.1 mg/ml, the 1.0 mg/ml, and the 10 mg/ml concentrations that the 0.1 mg/ml concentration appeared to be the optimum dose. The N357 0.1 mg/ml concentration treatment resulted in a statistically significant improvement in mean life span of 9%, a maximum improvement in lifespan of 14.3% at 50% mortality, and a maximum improvement in survival up to 16% between days 11 and 14. The Log-Ran test results and the Fisher's Exact test results showed significance overall for the length of the study and for each individual time point within the study for the N357 0.1 mg/ml concentration.

Both the N356 and the N357 treatments showed a dose-dependent effect as seen in FIGS. 28 and 32. The threshold for a positive effect on lifespan seemed to lie somewhere above 1.0 mg/ml and thus 0.1 mg/ml was accepted as the optimum dose of those concentrations that were tested. For both N356 and N357, when the concentration was increased to 1.0 mg/ml, the treatments caused a decrease in lifespan compared to a control. Similarly, at 10 mg/ml, a decrease in lifespan of the respective worm populations was seen for both N356 and N357. It is possible that treatments with concentrations of N356 and N357 below 0.1 mg/ml may also increase lifespan. This data indicate that the components of the formulation corresponding to antioxidants also increased lifespan above the effect produced by the herbal components of the formulation. The data indicate that there is a synergistic effect on lifespan from the administration of the antioxidant components and the herbal components. In some cases, there can be a complimentary effect on lifespan from the administration of the antioxidant components and the herbal components.

Example 3

Phenotypic screening was carried out as described in EXAMPLE 2 for various individual compounds of the N357 formulation. Individual compounds were assayed to determine any possible individual contribution that an individual compound may have to overall anti-ageing activity. Solutions of resveratrol, alpha lipoic acid, hesperidin (hesperetin), quercetin, and rutin hydrate were prepared at concentrations of 0.1 mg/ml and 10 mg/ml in DMSO. Resveratrol was sourced from Sigma Aldrich at ≥99% HPLC purity and was assigned a sample number of N108. Alpha lipoic acid was sourced from PureBulk™ USA as a racemic mix of R and S stereoisomers and was assigned a sample number of N198. Hesperidin was sourced from Sigma Aldrich at ≥80% purity and was assigned a sample number of N347. Quercetin was sourced from Tocris Bioscience at ≥98% HPLC purity and was assigned a sample number of N104. Rutin hydrate was sourced from Sigma Aldrich at ≥94% HPLC purity and was assigned a sample number of N346. The counts of the living and dead worms as a function of time were analyzed for each of the worm populations and used to prepare Kaplan-Meier survival curves and associated statistics for each of the worm populations as described above. Log-Rank test and Fisher's Exact test were also performed.

Figure 33:
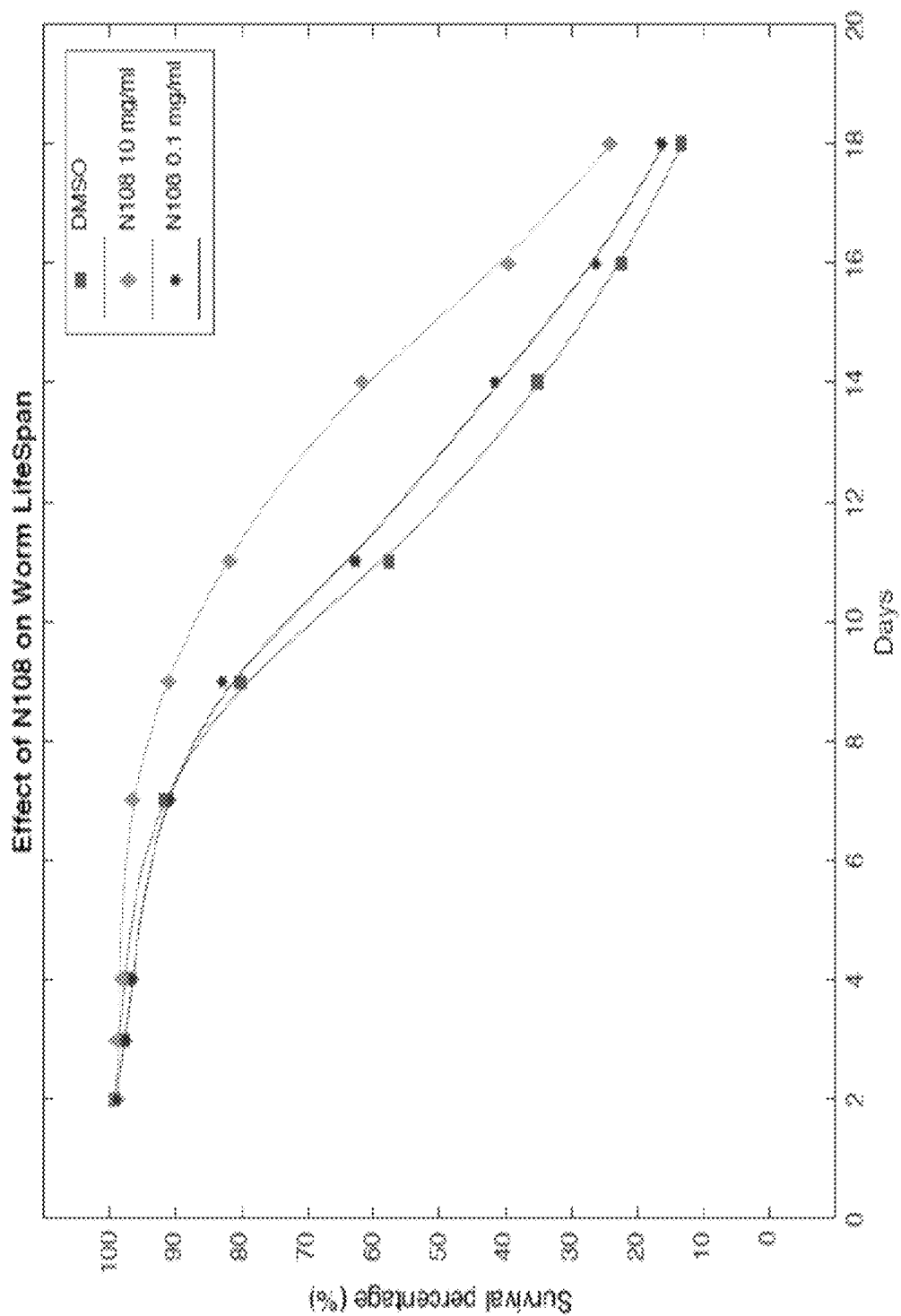
FIG. 33 illustrates a Kaplan-Meier survival curve for the worm population tested with N108 (resveratrol) at the 0.1 mg/ml and 10 mg/ml concentrations.
Figure 34:
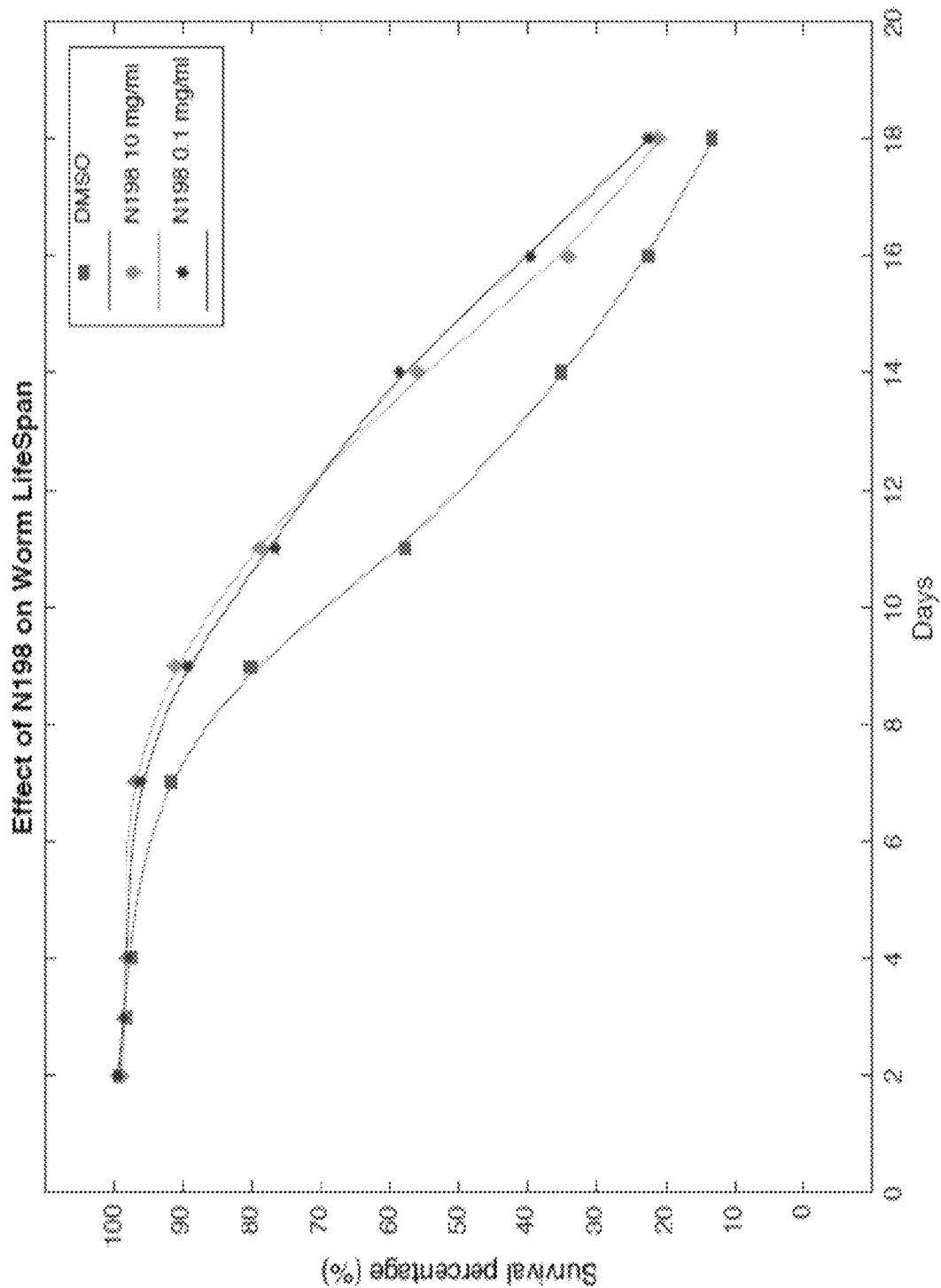
FIG. 34 illustrates a Kaplan-Meier survival curve for the worm population tested with N198 (alpha lipoic acid) at the 0.1 mg/ml and 10 mg/ml concentrations.
Figure 35:
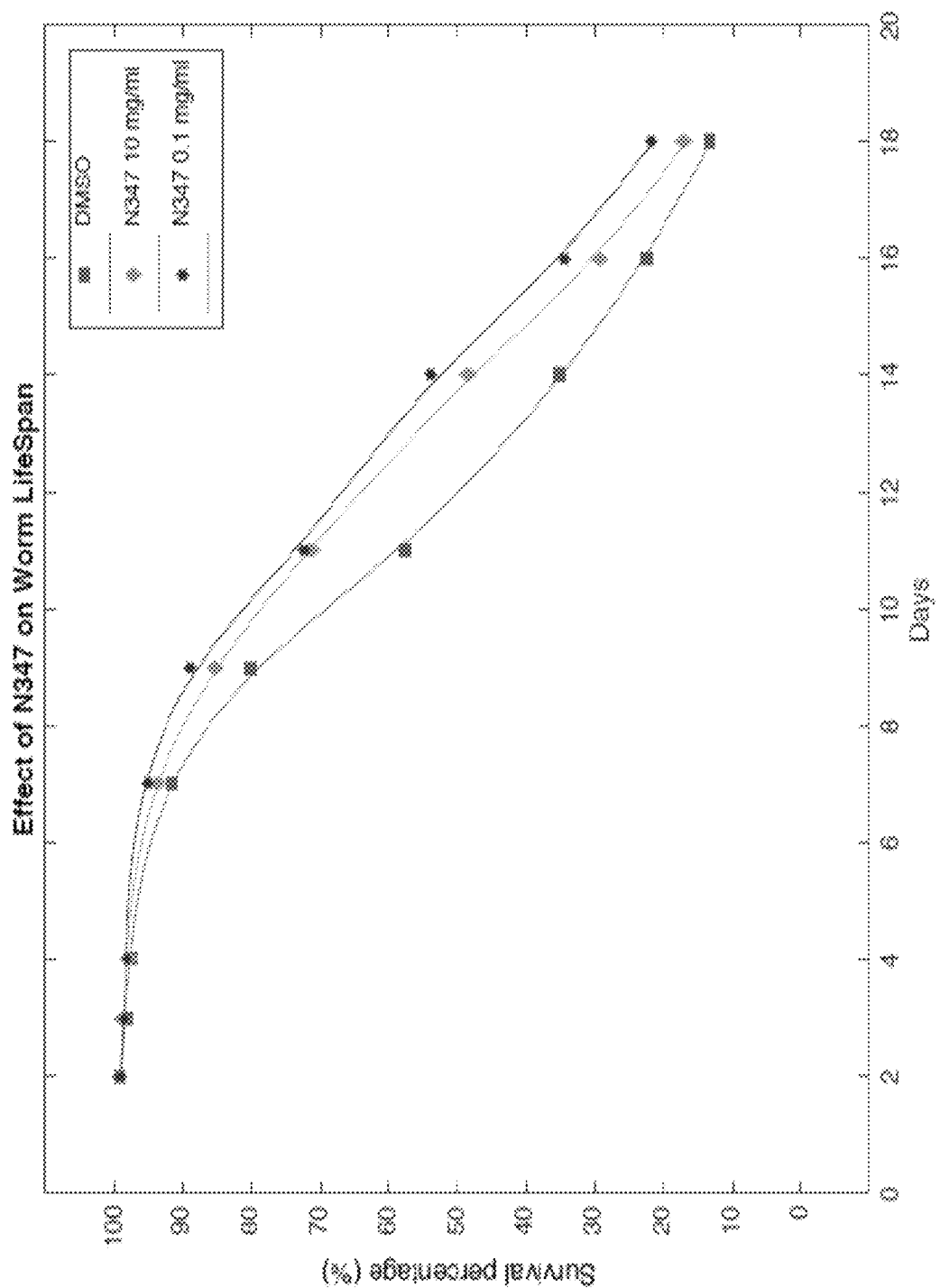
FIG. 35 illustrates a Kaplan-Meier survival curve for the worm population tested with N347 (hesperidin) at the 0.1 mg/ml and 10 mg/ml concentrations.
Figure 36:
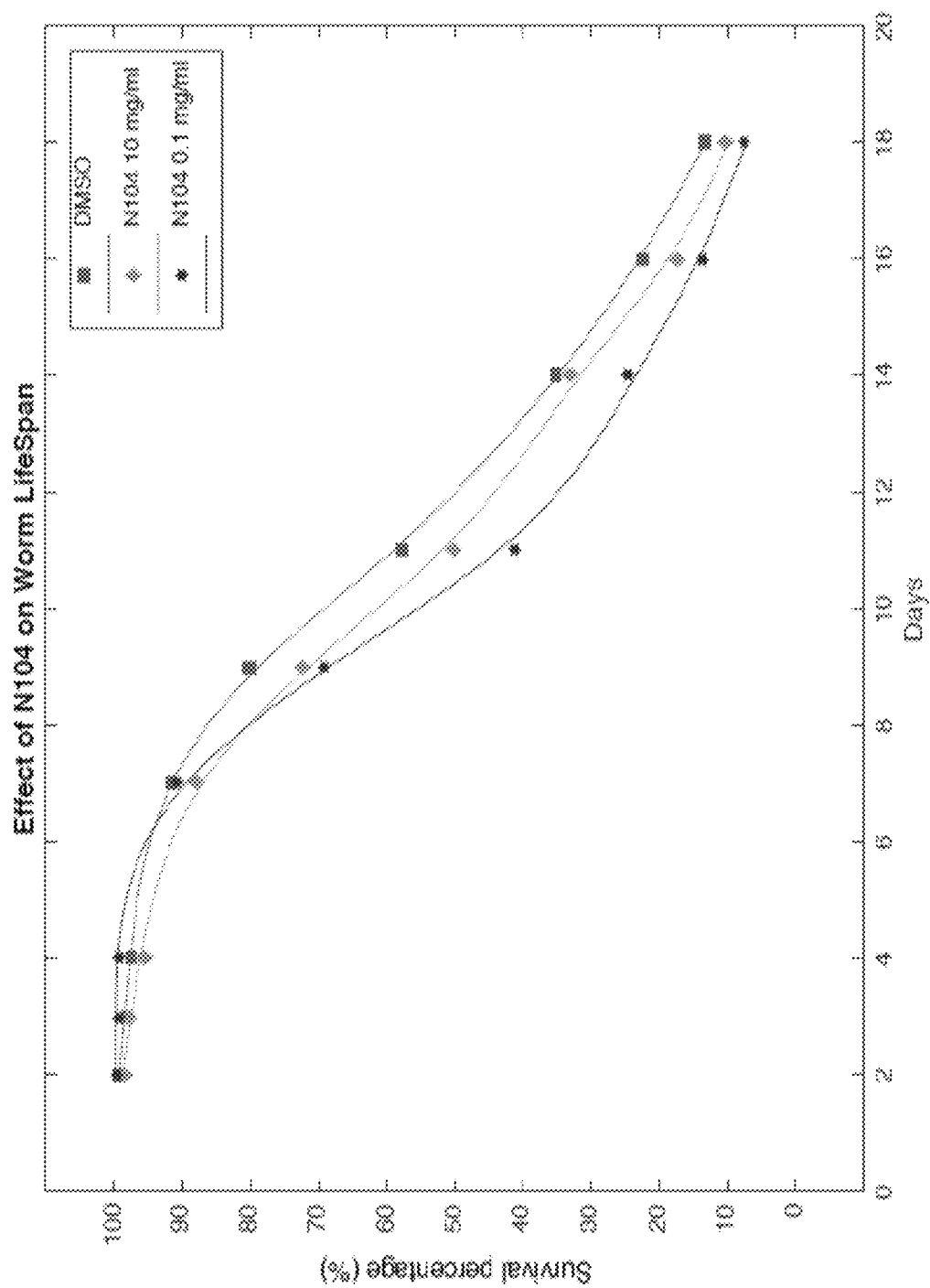
FIG. 36 illustrates a Kaplan-Meier survival curve for the worm population tested with N104 (quercetin) at the 0.1 mg/ml and 10 mg/ml concentrations.
Figure 37:
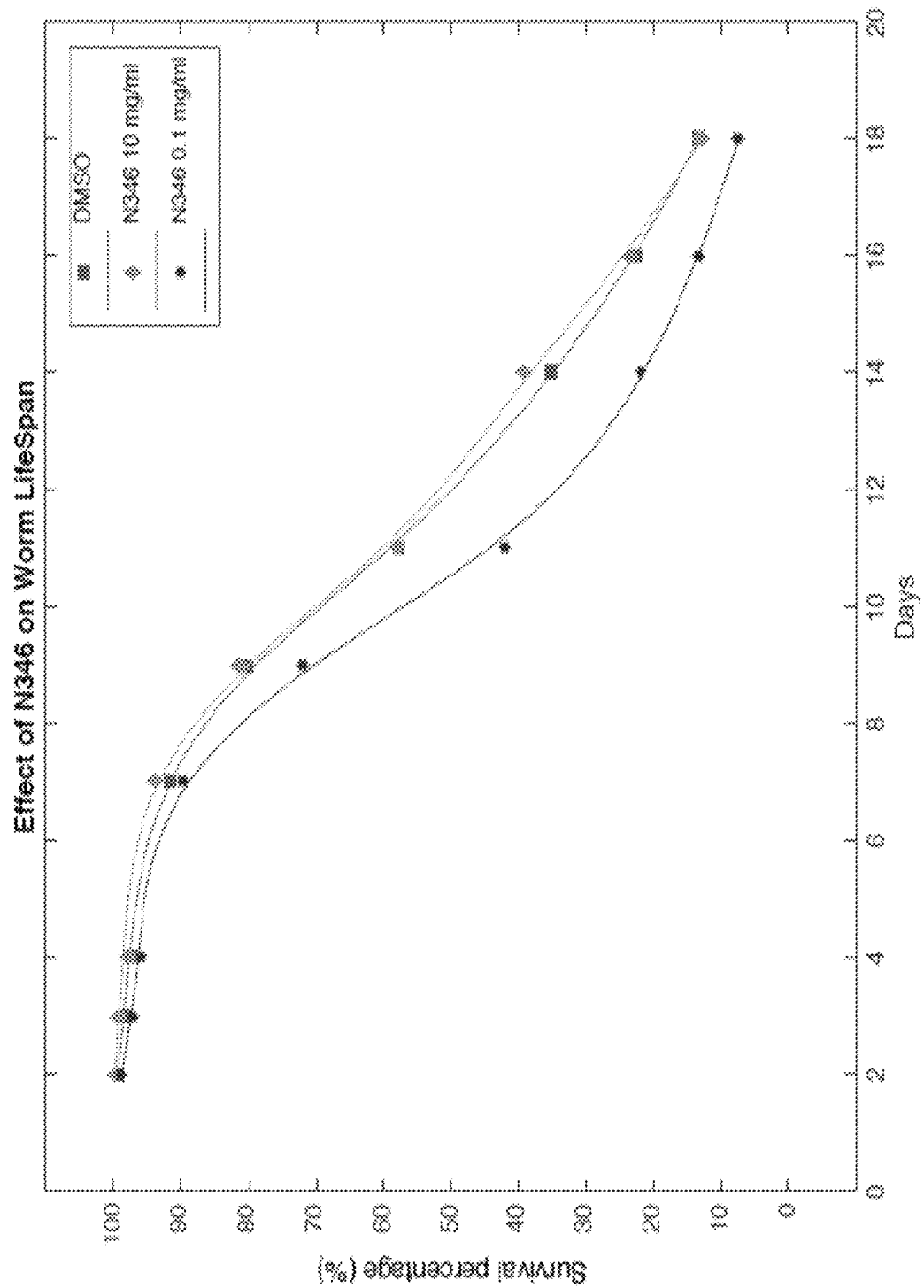
FIG. 37 illustrates a Kaplan-Meier survival curve for the worm population tested with N346 (rutin hydrate) at the 0.1 mg/ml and 10 mg/ml concentrations.

FIGS. 33 to 37 show Kaplan-Meier survival curves for the worm populations treated with resveratrol, alpha lipoic acid, hesperidin, quercetin, and rutin hydrate. FIG. 33 show a Kaplan-Meier survival curve for the worm population tested with N108 (resveratrol) at the 0.1 mg/ml and 10 mg/ml concentrations. FIG. 34 show a Kaplan-Meier survival curve for the worm population tested with N198 (alpha lipoic acid) at the 0.1 mg/ml and 10 mg/ml concentrations. FIG. 35 show a Kaplan-Meier survival curve for the worm population tested with N347 (hesperidin) at the 0.1 mg/ml and 10 mg/ml concentrations. FIG. 36 show a Kaplan-Meier survival curve for the worm population tested with N104 (quercetin) at the 0.1 mg/ml and 10 mg/ml concentrations. FIG. 37 show a Kaplan-Meier survival curve for the worm population tested with N346 (rutin hydrate) at the 0.1 mg/ml and 10 mg/ml concentrations.

The mean and median lifespan for each worm population treated with resveratrol, alpha lipoic acid, hesperidin, quercetin, and rutin hydrate are listed below in Table 18. The age in days at 25%, 50%, 75%, 90%, and 100% mortality are listed below in Table 19. The Log-Rank test results for each worm population compared to the DMSO control are shown below in Table 20. The Fisher's Exact Test results for each worm population compared to the DMSO control are shown below in Table 21.

TABLE 18

| Name | Days | Std. error | 95% C.I. |
|---|---|---|---|
| DMSO | 13.23 | 0.08 | 13.06~13.39 |
| N108 10 mg/ml (resveratrol) | 15.16 | 0.15 | 14.87~15.45 |
| N108 0.1 mg/ml (resveratrol) | 13.57 | 0.19 | 13.20~13.95 |
| N198 10 mg/ml (alpha lipoic acid) | 14.85 | 0.14 | 14.57~15.13 |
| N198 0.1 mg/ml (alpha lipoic acid) | 14.89 | 0.18 | 14.55~15.24 |
| N347 10 mg/ml (hesperidin) | 14.19 | 0.16 | 13.87~14.51 |
| N347 0.1 mg/ml (hesperidin) | 14.55 | 0.16 | 14.23~14.86 |
| N104 10 mg/ml (quercetin) | 12.54 | 0.27 | 12.02~13.07 |
| N104 0.1 mg/ml (quercetin) | 12.17 | 0.20 | 11.78~12.57 |
| N346 10 mg/ml (rutin hydrate) | 13.43 | 0.22 | 13.01~13.86 |
| N346 0.1 mg/ml (rutin hydrate) | 12.03 | 0.21 | 11.61~12.45 |

TABLE 19

| Name | 25% mortality | 50% mortality | 75% mortality | 90% mortality | 100% mortality |
|---|---|---|---|---|---|
| DMSO | 11 | 14 | 16 | — | — |
| N108 10 mg/ml (resveratrol) | 14 | 16 | 18 | — | — |
| N108 0.1 mg/ml (resveratrol) | 11 | 14 | 18 | — | — |
| N198 10 mg/ml (alpha lipoic acid) | 14 | 16 | 18 | — | — |
| N198 0.1 mg/ml (alpha lipoic acid) | 14 | 16 | 18 | — | — |
| N347 10 mg/ml (hesperidin) | 11 | 14 | 18 | — | — |
| N347 0.1 mg/ml (hesperidin) | 11 | 16 | 18 | — | — |
| N104 10 mg/ml (quercetin) | 9 | 14 | 16 | — | — |
| N104 0.1 mg/ml (quercetin) | 9 | 11 | 14 | 18 | — |
| N346 10 mg/ml (rutin hydrate) | 11 | 14 | 16 | — | — |
| N346 0.1 mg/ml (rutin hydrate) | 9 | 11 | 14 | 18 | — |

TABLE 20

| Condition | Chi$^2$ | P-value | Bonferroni P-value |
|---|---|---|---|
| DMSO vs. N108 at 10 mg/ml | 86.88 | 0.0e+00 | 0.0e+00 |
| DMSO vs. N108 at 0.1 mg/ml | 4.59 | 0.0321 | 0.0642 |
| DMSO vs. N198 at 10 mg/ml | 60.49 | 0.0e+00 | 0.0e+00 |
| DMSO vs. N198 at 0.1 mg/ml | 55.75 | 0.0e+00 | 0.0e+00 |
| DMSO vs. N347 at 10 mg/ml | 19.37 | 1.1e−05 | 2.2e−05 |
| DMSO vs. N347 at 0.1 mg/ml | 45.04 | 0.0e+00 | 0.0e+00 |
| DMSO vs. N104 at 10 mg/ml | 4.98 | 0.0256 | 0.0512 |
| DMSO vs. N104 at 0.1 mg/ml | 26.70 | 2.4e−07 | 4.7e−07 |
| DMSO vs. N346 at 10 mg/ml | 0.23 | 0.6322 | 1.0000 |
| DMSO vs. N346 at 0.1 mg/ml | 28.00 | 1.2e−07 | 2.4e−07 |

TABLE 21

| Condition | P-value at 25% | P-value at 50% | P-value at 75% | P-value at 90% |
|---|---|---|---|---|
| DMSO vs. N108 at 10 mg/ml | 3.1e−12 | 2.7e−12 | 2.9e−12 | 5.6e−09 |
| DMSO vs. N108 at 0.1 mg/ml | 0.0517 | 0.0108 | 0.1303 | 0.1226 |
| DMSO vs. N198 at 10 mg/ml | 3.2e−12 | 3.2e−12 | 9.1e−08 | 1.1e−05 |
| DMSO vs. N198 at 0.1 mg/ml | 2.7e−12 | 2.6e−12 | 2.6e−12 | 4.4e−06 |
| DMSO vs. N347 at 10 mg/ml | 2.6e−08 | 7.4e−08 | 0.0028 | 0.0313 |
| DMSO vs. N347 at 0.1 mg/ml | 1.1e−09 | 2.5e−12 | 2.1e−07 | 8.5e−06 |
| DMSO vs. N104 at 10 mg/ml | 0.0330 | 0.5557 | 0.0754 | 0.2111 |
| DMSO vs. N104 at 0.1 mg/ml | 9e−08 | 9.8e−08 | 0.0002 | 0.0031 |
| DMSO vs. N346 at 10 mg/ml | 0.8993 | 0.1912 | 0.7094 | 1.0000 |
| DMSO vs. N346 at 0.1 mg/ml | 2.7e−07 | 2.7e−07 | 2.7e−06 | 0.0031 |

The analysis indicated that resveratrol (N108), alpha lipoic acid (N198), and hesperidin (N347) all showed significant positive and dose-dependent increase of chronological lifespan. Quercetin (N104) and rutin (N346) appeared to show significant negative effect on chronological lifespan at certain tested concentrations. FIG. 33 shows that resveratrol appeared to extend lifespan by about 15% at 10 mg/ml. FIG. 34 shows that alpha lipoic acid appeared to extend lifespan by about 12.5% at both 0.1 mg/ml and 10 mg/ml. FIG. 35 shows that hesperidin appeared to extend lifespan by about 10% at 0.1 mg/ml. FIG. 36 shows that quercetin, at least at the concentrations tested and under the conditions tested, appeared to decrease lifespan by about 9% at 0.1 mg/ml. FIG. 37 shows that rutin hydrate, at least at the concentrations tested and under the conditions tested, appeared to decrease lifespan by about 9% at 0.1 mg/ml. The summary of results for the worm populations treated with resveratrol, alpha lipoic acid, hesperidin, quercetin, and rutin hydrate compared to DMSO control are summarized below in Table 22.

TABLE 22

| Compound | Statistically Significant Result | % Change in Mean Lifespan |
|---|---|---|
| 0.1 mg/ml (resveratrol) | No statistical difference | N/A |
| 10 mg/ml (resveratrol) | Statistically significant increase | +15% |
| 0.1 mg/ml (alpha lipoic acid) | Statistically significant increase | +12.5% |
| 10 mg/ml (alpha lipoic acid) | Statistically significant increase | +12.5% |
| 0.1 mg/ml (hesperidin) | Statistically significant increase | +10% |
| 10 mg/ml (hesperidin) | No statistical difference | N/A |
| 0.1 mg/ml (quercetin) | Statistically significant decrease | −9% |
| 10 mg/ml (quercetin) | No statistical difference | N/A |
| 0.1 mg/ml (rutin hydrate) | Statistically significant decrease | −8% |
| 10 mg/ml (rutin hydrate) | No statistical difference | N/A |

N/A = Not applicable

Example 4

In vitro assays of Nrf2 signaling activity were carried out for each of alpha lipoic acid, resveratrol, curcumin, EGCG, Olivol®, rutin, quercetin, and hesperetin. The assays were carried out with a fluorescent reporter assay that utilized a human retinal epithelial cell line. The assays also included validation by RT-PCR (reverse transcription polymerase chain reaction) of Nrf2 target genes. The human retinal epithelial cell line was purchased from ATCC (American Type Cell Culture, Manassas, Va.) and was configured to function as a fluorescent reporter assay. Test solutions of each of the alpha lipoic acid, resveratrol, curcumin, EGCG, Olivol®, rutin, quercetin, and hesperetin were prepared by serial dilution. Control solutions were also prepared. Positive control solutions of a known Nrf2 agonist, L-sulphoraphane was also prepared. Each test solution was then assayed for Nrf2 signaling activity using the fluorescent reporter assay and compared to control assays. The positive control solutions were also tested.

Figure 38:
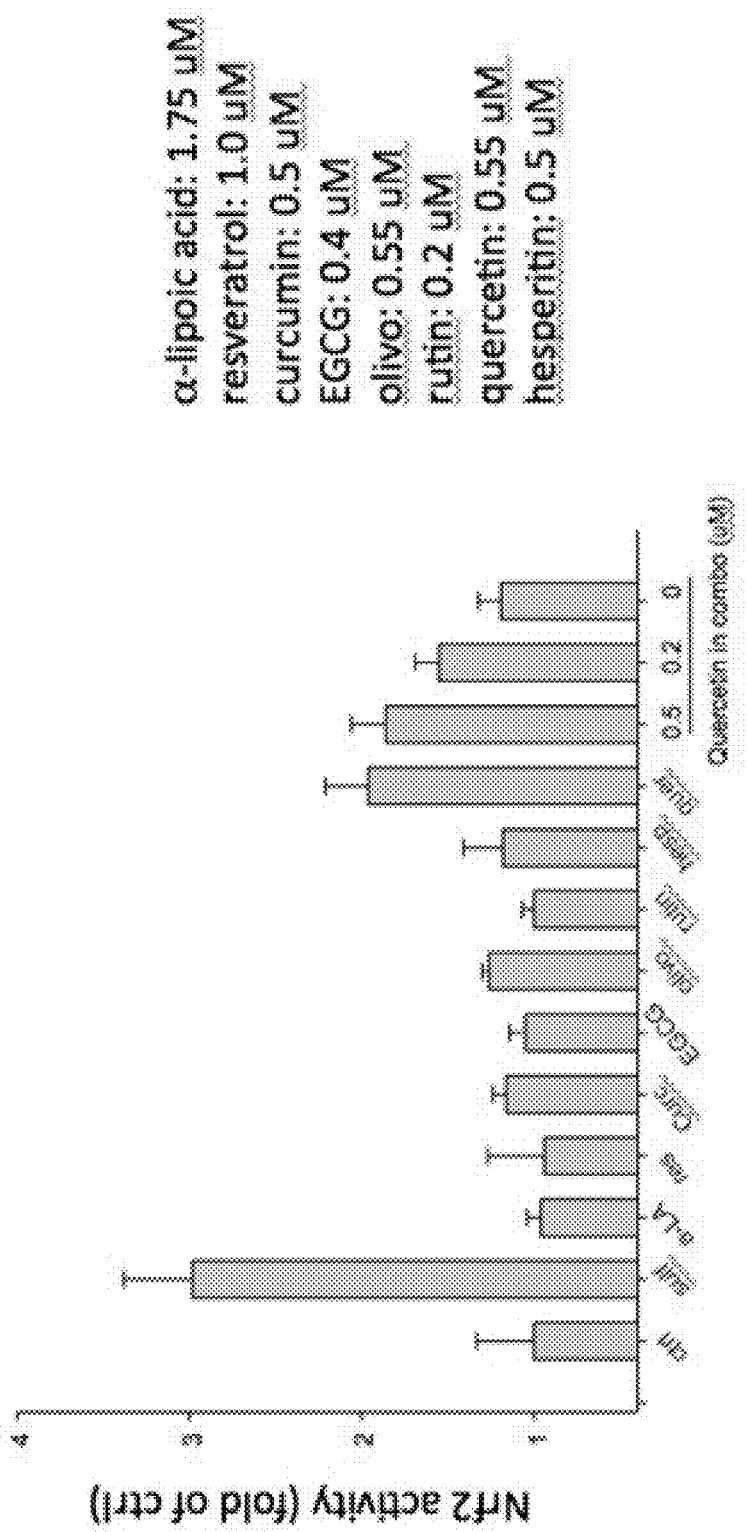
FIG. 38 illustrates fold-activation of Nrf2 by test solutions compared to control.
Figure 40:
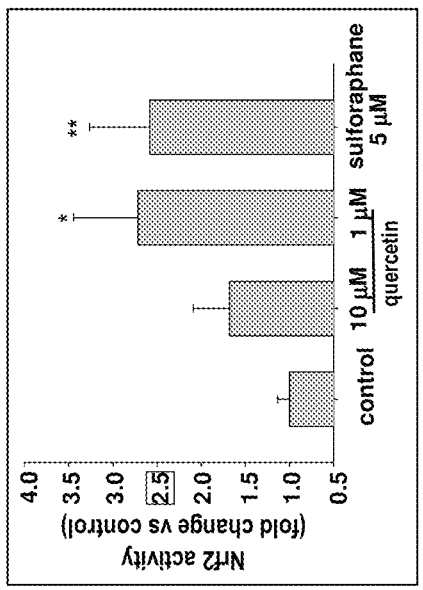
FIG. 40 illustrates fold-activation of Nrf2 by quercetin compared to control.
Figure 41:
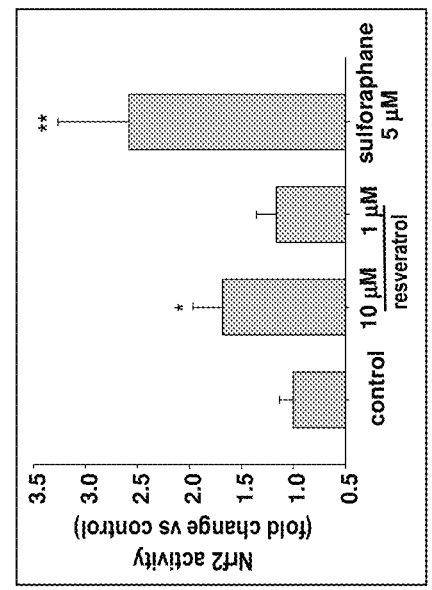
FIG. 41 illustrates fold-activation of Nrf2 by resveratrol compared to control.
Figure 39:
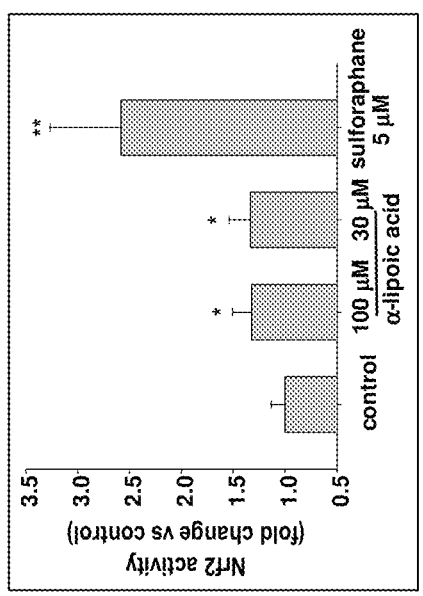
FIG. 39 illustrates fold-activation of Nrf2 by alpha lipoic acid compared to control.

FIG. 38 shows the fold-activation of Nrf2 by each test solution compared to the control. The minimum inducing concentrations of alpha lipoic acid was 1.75 of resveratrol was 1.0 and of quercetin was 0.55 µM. FIG. 39 shows the fold-activation of Nrf2 by alpha lipoic acid at 100 µM and 30 µM against a control. The fold activation of 5 µM sulforaphane, as a positive control is also shown. Alpha lipoic acid demonstrated activation of Nrf2 at both 100 and 30 µM. FIG. 40 shows the fold-activation of Nrf2 by quercetin at 10 µM and 1 against a control. The fold activation of 5 µM sulforaphane, as a positive control is also shown. Quercetin demonstrated activation of Nrf2 at both 10 µM and 1 with more activation at the 1 µM concentration. FIG. 41 shows the fold-activation of Nrf2 by resveratrol at 10 µM and 1 against a control. The fold activation of 5 µM sulforaphane, as a positive control is also shown. Resveratrol demonstrated activation of Nrf2 at both 10 µM and 1 with more activation at the 10 µM concentration.

Example 5: mTOR/Autophagy Pathway of Cellular Quality Control

Mitochondria perform many essential functions within the cell. However, the most notable and perhaps most important function is the production of ATP through oxidative phosphorylation. Unfortunately in the production of ATP, large amounts of reactive oxygen species are produced. While much of these damaging molecules are quenched as they are produced, some damage does occur. Even when mitochondria are functionally normal, 1-2% of the oxygen they consume is converted to superoxide and then to hydrogen peroxide. These directly damage the membrane of the mitochondria, reducing their efficiency. Damaged but still functional mitochondria might release up to tenfold more hydrogen peroxide, further damaging the mitochondria and other organelles within the cell. As such we have developed a process of mitochondrial turnover, a cellular quality control process. Removal of the damaged mitochondria, and recycling of the component parts is termed autophagy or mitophagy. Effective mitophagy removes the most damaged mitochondria producing the highest amounts of reactive oxygen species. As such, mitophagy will greatly reduce oxidative burden, thus linking mitophagy with the antioxidant theory of aging.

An accumulation of damaged mitochondria in cells due to a slowed-down rate of mitochondrial turnover and inadequate removal of damaged mitochondria, has been implicated as both cause and consequence of the aging process and a number of age-related pathologies. Further, the failure to maintain mitochondrial quality control through mitophagy may explain why the heart, brain, and components of the immune system are most vulnerable to dysfunction as organisms age. In addition, mitophagy is the only known process for mitochondrial turnover.

It has been known for years that calorie reduction in animal models increases longevity, though the exact mechanism is uncertain. More recently, it was discovered that one of the key processes that occurs during calorie restriction is an upregulation of mitophagy. This upregulation is thought to be the driving force in increased longevity.

Much research on autophagy and mitophagy has occurred over the past several decades, and several reviews are already available. The key mechanism in upregulation of autophagy is an inhibition of activity of the mammalian target of rapamycin (mTOR). A significant body of research by pharmaceutical companies has been centered on new mTOR inhibitors. In addition to Rapamycin, many other drugs that inhibit mTOR and upregulate mitophagy have been discovered. A large group of natural products, that also inhibit mTOR, however have been observed, but largely ignored by these same pharmaceutical researchers. So for example epigallocatechin gallate (EGCG), caffeine, curcumin, resveratrol and hydroxytyrosol have all been shown to inhibit mTOR, up-regulate mitophagy, and increase the rate of mitochondrial turnover.

As such, we propose to increase the amounts of these natural phytochemical antioxidants in the Essentials, so that we can more efficiently reduce oxidative burden through mitophagy."

The terms "a," "an," "the," and similar referents used in the context of describing the disclosure (especially in the context of the following claims) are to be construed to cover both the singular and the plural unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

It is contemplated that numerical values, as well as other values that are recited herein, are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or another multiple of the actual value indicated, and/or described in the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in or deleted from a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

In closing, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

We claim:

1. A nutritional supplement for an adult human for supporting endogenous systems associated with increasing life span, the nutritional supplement comprising:
    an antioxidant mixture that includes each of the following ingredients:
        between 24 mg and 26 mg of alpha lipoic acid;
        between 9 mg and 11 mg of resveratrol;
        between 17 mg and 19 mg of curcumin;
        between 16.5 mg and 18.5 mg of epigallocatechin gallate (EGCG);
        between 6.5 mg and 8.5 mg of olive fruit extract;
        between 9 mg and 11 mg of rutin;
        between 14 mg and 16 mg of quercetin; and
        10 mg of hesperidin.

2. The nutritional supplement of claim 1, wherein the antioxidant mixture includes:
    25 mg of alpha lipoic acid;
    10 mg of resveratrol;
    18.06 mg of curcumin;
    17.5 mg of EGCG;
    7.5 mg of olive fruit extract;
    10 mg of rutin;
    15 mg of quercetin;
    and 10 mg of hesperidin.

3. The nutritional supplement of claim 1, wherein the antioxidant mixture further includes each of the following ingredients:
    between 0.01 and 1 mg of mixed carotenoids;
    between 0.01 and 3 mg of beta carotene;
    between 0.01 and 1 mg of retinyl acetate;
    between 10 mg and 200 mg of vitamin C;
    between 0.001 and 1 mg of vitamin D3;
    between 10 and 100 mg of vitamin E;
    between 0.01 and 1 mg of vitamin K1;
    between 0.0001 and 1 mg of vitamin K2;
    between 1 and 20 mg of vitamin B1;
    between 1 and 20 mg of vitamin B2;
    between 1 and 20 mg of niacin;
    between 1 and 20 mg of niacinamide;
    between 1 and 20 mg of vitamin B6;
    between 0.01 and 2 mg of folic acid;
    between 0.001 and 2 mg of vitamin B12;
    between 0.001 and 2 mg of biotin;
    between 1 and 50 mg of pantothenic acid;
    between 1 and 50 mg of mixed tocopherols;
    between 1 and 100 mg of inositol;

between 1 and 200 mg of choline bitartrate;
between 0.1 and 20 mg of coenzyme Q10;
between 0.01 and 2 mg of lutein; and
between 0.01 and 2 mg of lycopene.

4. The nutritional supplement of claim 3, further comprising:
a mineral mixture that includes each of the following ingredients:
between 10 and 200 mg of calcium;
between 0.001 and 10 mg of iodine;
between 1 and 200 mg of magnesium;
between 0.1 and 50 mg of zinc;
between 0.001 and 2 mg of selenium;
between 0.01 and 10 mg of copper;
between 0.01 and 10 mg of manganese;
between 0.001 and 1 mg of chromium;
between 0.001 and 1 mg of molybdenum;
between 0.01 and 10 mg of boron;
between 0.1 and 10 mg of silicon;
between 0.001 and 1 mg of vanadium;
between 0.01 and 10 mg of ultra-trace minerals; and
between 1 and 100 mg of N-acetyl L-cysteine.

5. The nutritional supplement of claim 4, wherein the antioxidant mixture is contained in one or more first tablets and the mineral mixture is contained in one or more second tablets.

6. The nutritional supplement of claim 4, wherein the antioxidant mixture is contained in a single first tablet and the mineral mixture is contained in a single second tablet.

7. The nutritional supplement of claim 1, further comprising:
a mineral mixture that includes each of the following ingredients:
between 10 and 200 mg of calcium;
between 0.001 and 10 mg of iodine;
between 1 and 200 mg of magnesium;
between 0.1 and 50 mg of zinc;
between 0.001 and 2 mg of selenium;
between 0.01 and 10 mg of copper;
between 0.01 and 10 mg of manganese;
between 0.001 and 1 mg of chromium;
between 0.001 and 1 mg of molybdenum;
between 0.01 and 10 mg of boron;
between 0.1 and 10 mg of silicon;
between 0.001 and 1 mg of vanadium;
between 0.01 and 10 mg of ultra-trace minerals; and
between 1 and 100 mg of N-acetyl L-cysteine.

8. The nutritional supplement of claim 7, wherein the antioxidant mixture is contained in one or more first tablets and the mineral mixture is contained in one or more second tablets.

9. The nutritional supplement of claim 7, wherein the antioxidant mixture is contained in a single first tablet and the mineral mixture is contained in a single second tablet.

10. The nutritional supplement of claim 9, wherein the antioxidant mixture includes:
25 mg of alpha lipoic acid;
10 mg of resveratrol;
18.06 mg of curcumin;
17.5 mg of EGCG;
7.5 mg of olive fruit extract;
10 mg of rutin;
15 mg of quercetin;
and 10 mg of hesperidin.

11. The nutritional supplement of claim 1, wherein the antioxidant mixture is contained in a first tablet, the antioxidant mixture further including each of the following ingredients:
mixed carotenoids;
beta carotene;
retinyl acetate;
vitamin C;
vitamin D3;
vitamin E;
vitamin K1;
vitamin K2;
vitamin B1;
vitamin B2;
niacin;
vitamin B6;
folic acid;
vitamin B12;
biotin;
pantothenic acid;
mixed tocopherols;
inositol;
choline bitartrate;
coenzyme Q10;
lutein; and
lycopene;
the nutritional supplement further comprising a second tablet that contains a mineral mixture, the mineral mixture including each of the following ingredients:
calcium;
iodine;
magnesium;
zinc;
selenium;
copper;
manganese;
chromium;
molybdenum;
boron;
silicon;
vanadium;
ultra-trace minerals; and
N-acetyl L-cysteine.

12. A nutritional supplement for an adult human comprising:
a first tablet that includes an antioxidant mixture, the antioxidant mixture including each of the following ingredients:
between 24 mg and 26 mg of alpha lipoic acid;
between 9 mg and 11 mg of resveratrol;
between 17 mg and 19 mg of curcumin;
between 16.5 mg and 18.5 mg of EGCG;
between 6.5 mg and 8.5 mg of olive fruit extract;
between 9 mg and 11 mg of rutin;
between 14 mg and 16 mg of quercetin;
10 mg of hesperidin;
mixed carotenoids;
beta carotene;
retinyl acetate;
vitamin C;
vitamin D3;
vitamin E;
vitamin K1;
vitamin K2;
vitamin B1;
vitamin B2;
niacin;

niacinamide
vitamin B6;
folic acid;
vitamin B12;
biotin;
pantothenic acid;
mixed tocopherols;
inositol;
choline bitartrate;
coenzyme Q10;
lutein; and
lycopene; and
a second tablet that includes a mineral mixture, the mineral mixture including each of the following ingredients:
calcium;
iodine;
magnesium;
zinc;
selenium;
copper;
manganese;
chromium;
molybdenum;
boron;
silicon;
vanadium;
ultra-trace minerals; and
N-acetyl L-cysteine.

13. The nutritional supplement of claim 12, wherein the first tablet includes:
25 mg of alpha lipoic acid;
10 mg of resveratrol;
18.06 mg of curcumin;
17.5 mg of epigallocatechin gallate (EGCG);
7.5 mg of olive fruit extract;
10 mg of rutin;
15 mg of quercetin;
and 10 mg of hesperidin.

14. The nutritional supplement of claim 12, wherein the first tablet includes:
between 0.01 and 1 mg of mixed carotenoids;
between 0.01 and 3 mg of beta carotene;
between 0.01 and 1 mg of retinyl acetate;
between 10 mg and 200 mg of vitamin C;
between 0.001 and 1 mg of vitamin D3;
between 10 and 100 mg of vitamin E;
between 0.01 and 1 mg of vitamin K1;
between 0.0001 and 1 mg of vitamin K2;
between 1 and 20 mg of vitamin B1;
between 1 and 20 mg of vitamin B2;
between 1 and 20 mg of niacin;
between 1 and 20 mg of niacinamide;
between 1 and 20 mg of vitamin B6;
between 0.01 and 2 mg of folic acid;
between 0.001 and 2 mg of vitamin B12;
between 0.001 and 2 mg of biotin;
between 1 and 50 mg of pantothenic acid;
between 1 and 50 mg of mixed tocopherols;
between 1 and 100 mg of inositol;
between 1 and 200 mg of choline bitartrate;
between 0.1 and 20 mg of coenzyme Q10;
between 0.01 and 2 mg of lutein; and
between 0.01 and 2 mg of lycopene.

15. The nutritional supplement of claim 14, wherein the second tablet includes:
between 10 and 200 mg of calcium;
between 0.001 and 10 mg of iodine;
between 1 and 200 mg of magnesium;
between 0.1 and 50 mg of zinc;
between 0.001 and 2 mg of selenium;
between 0.01 and 10 mg of copper;
between 0.01 and 10 mg of manganese;
between 0.001 and 1 mg of chromium;
between 0.001 and 1 mg of molybdenum;
between 0.01 and 10 mg of boron;
between 0.1 and 10 mg of silicon;
between 0.001 and 1 mg of vanadium;
between 0.01 and 10 mg of ultra-trace minerals; and
between 1 and 100 mg of N-acetyl L-cysteine.

16. A nutritional supplement for an adult human for supporting endogenous systems associated with increasing life span, the nutritional supplement consisting essentially of:
an antioxidant mixture that includes each of the following ingredients:
25 mg of alpha lipoic acid;
10 mg of resveratrol;
18.06 mg of curcumin;
17.5 mg of EGCG;
7.5 mg of olive fruit extract;
10 mg of rutin;
15 mg of quercetin;
10 mg of hesperidin;
between 0.01 and 1 mg of mixed carotenoids;
between 0.01 and 3 mg of beta carotene;
between 0.01 and 1 mg of retinyl acetate;
between 10 mg and 200 mg of vitamin C;
between 0.001 and 1 mg of vitamin D3;
between 10 and 100 mg of vitamin E;
between 0.01 and 1 mg of vitamin K1;
between 0.0001 and 1 mg of vitamin K2;
between 1 and 20 mg of vitamin B1;
between 1 and 20 mg of vitamin B2;
between 1 and 20 mg of niacin;
between 1 and 20 mg of niacinamide;
between 1 and 20 mg of vitamin B6;
between 0.01 and 2 mg of folic acid;
between 0.001 and 2 mg of vitamin B12;
between 0.001 and 2 mg of biotin;
between 1 and 50 mg of pantothenic acid;
between 1 and 50 mg of mixed tocopherols;
between 1 and 100 mg of inositol;
between 1 and 200 mg of choline bitartrate;
between 0.1 and 20 mg of coenzyme Q10;
between 0.01 and 2 mg of lutein; and
between 0.01 and 2 mg of lycopene; and
a mineral mixture.

17. The nutritional supplement of claim 16, wherein the mineral mixture includes calcium, magnesium, potassium and zinc.

* * * * *